United States Patent
Semple et al.

(10) Patent No.: US 6,287,591 B1
(45) Date of Patent: Sep. 11, 2001

(54) CHARGED THERAPEUTIC AGENTS ENCAPSULATED IN LIPID PARTICLES CONTAINING FOUR LIPID COMPONENTS

(75) Inventors: Sean C. Semple, Vancouver; Sandra K. Klimuk, N. Vancouver; Troy Harasym, Vancouver; Michael J. Hope, Vancouver; Steven M. Ansell, Vancouver; Pieter Cullis, Vancouver; Peter Scherrer, Vancouver; Dan Debeyer, Vancouver, all of (CA)

(73) Assignee: Inex Pharmaceuticals Corp., Burnaby (CA)

( * ) Notice: Subject to any disclaimer, the term of this patent is extended or adjusted under 35 U.S.C. 154(b) by 0 days.

(21) Appl. No.: 09/078,954

(22) Filed: May 14, 1998

Related U.S. Application Data

(63) Continuation-in-part of application No. 08/856,374, filed on May 14, 1997, now abandoned.

(51) Int. Cl.[7] .......................... A61K 9/127; A61K 31/70; C12N 11/02; C12N 15/88; C07H 21/00
(52) U.S. Cl. ...................... 424/450; 428/402.2; 435/177; 435/458; 514/44; 536/22.1
(58) Field of Search .............................. 424/450; 435/174, 435/177, 458; 428/402.2; 514/44; 536/22.1, 23.1

(56) References Cited

U.S. PATENT DOCUMENTS

| | | | |
|---|---|---|---|
| 5,264,618 | 11/1993 | Felgner et al. | 560/224 |
| 5,552,155 | 9/1996 | Bailey et al. | 424/450 |
| 5,595,756 | 1/1997 | Bally et al. | 424/450 |
| 5,965,542 | * 10/1999 | Wasan et al. | 514/44 |

FOREIGN PATENT DOCUMENTS

WO 95/27478 A1  10/1995 (WO).

(List continued on next page.)

OTHER PUBLICATIONS

Needham et al., J. Liposome Res. 2: 411–430 (1992).*

(List continued on next page.)

Primary Examiner—David M. Naff
(74) Attorney, Agent, or Firm—Oppedahl & Larson LLP

(57) ABSTRACT

Lipid-therapeutic agent particles are prepared containing a charged therapeutic agent encapsulated in lipid portion containing at least two lipid components including a protonatable or deprotonatable lipid such as an amino lipid and a lipid that prevents particle aggregation during lipid-therapeutic agent particle formation such as a PEG-modified or polyamide oligomer-modified lipid. Other lipid components may also be present and these include a neutral lipid such as DSPC, POPC, DOPE or SM, and a sterol such as Chol. The therapeutic agent is encapsulated by combining a mixture of the lipids with a buffered aqueous solution of a charged therapeutic agent to form an intermediate mixture containing lipid-encapsulated therapeutic agent particles, and changing the pH of the intermediate mixture to neutralize at least some surface charges on the particles. The method permits high ratios of therapeutic agent to lipid and encapsulation efficiencies in excess of 50%. The method is particularly useful for preparing lipid-encapsulated nucleic acids such as an antisense polyanionic nucleic acid having exclusively phosphodiester linkages. The encapsulated nucleic acid can be contacted with a cell to introduce the nucleic acid into the cell such as for treatment or prevention of a disease characterized by aberrant expression of a gene. A pharmaceutical composition may be prepared containing the lipid-encapsulated therapeutic agent particles and a carrier.

72 Claims, 17 Drawing Sheets pH 4.0 INTERNAL
pH 4.0 EXTERNAL

COLUMN CHROMATOGRAPHY
1. EXCHANGE pH 4.0 CITRATE FOR pH 7.5 HBS
2. NEUTRALIZE SURFACE DODAP; ANTISENSE RELEASE
3. REMOVAL OF NON-ENCAPSULATED ANTISENSE

RELEASE OF SURFACE ANTISENSE pH 4.0 INTERNAL
pH 7.5 EXTERNAL

FOREIGN PATENT DOCUMENTS

| | | |
|---|---|---|
| WO 96/10390 | 4/1996 | (WO) . |
| WO 96/10391 | 4/1996 | (WO) . |
| WO 96/18372 A2 | 6/1996 | (WO) . |
| WO 96/40964 | 12/1996 | (WO) . |
| WO 97/07784 | 3/1997 | (WO) . |
| WO 97/46223 A1 | 12/1997 | (WO) . |
| WO 97/46671 | 12/1997 | (WO) . |

OTHER PUBLICATIONS

Li et al., J. Liposome Res. 7: 411–430 (1997).*

Zelphati, O. and Szoka, F.C., Jr., "Liposomes as a carrier for intracellular delivery of antisense oligonucleotides: a real or magic bullet?", Journal of controlled Release 41:99–119, 1996.

Tomita, N. et al. Transient Decrease in High Blood pressure by In Vivo Transfer of Antisense Oligodeoxynucleotides Against Rat Angiotensinogen', Hypertension 26(1): 131–136, Jul. 1995.

Litzinger, D.C., "Limitations of Cationic Liposomes for Antisense Oligonucleotide Delivery In Vivo", Journal of Liposome Research 7(1):51–61, 1997.

Wielbo, D., et al., "Inhibition of Hypertension by Peripheral Administration of Antisense Oligodeoxynucleotides", Hypertension 28(1): 147–151, Jul. 1996.

Thierry, A.R., et al., "Lipsomal Delivery as a New Approach to Transport Antisense Oligonucleotides", in Gene Regulation:Giology of Antisense RNA and DNA, ed. R.P. Erickson and J.G. Izant, Raven Press, Ltd. New York, pp. 147–161, 1992.

Akhtar, S. and R.L. Juliano, "Liposome delivery of antisense oligonucleotides: adsorption and efflux characteristics of phosphorothioate oligodeoxynucleotides", Journal of Controlled Release 22(1): 47–56, Sep. 1992.

Zelphati, O., et al., "Inhibition of HIV–1 Replication in Cultured Cells with Antisense Oligonucleotides Encapsulated in Immunoliposomes", Antisense Research and Development, 3:323–338, 1993.

* cited by examiner

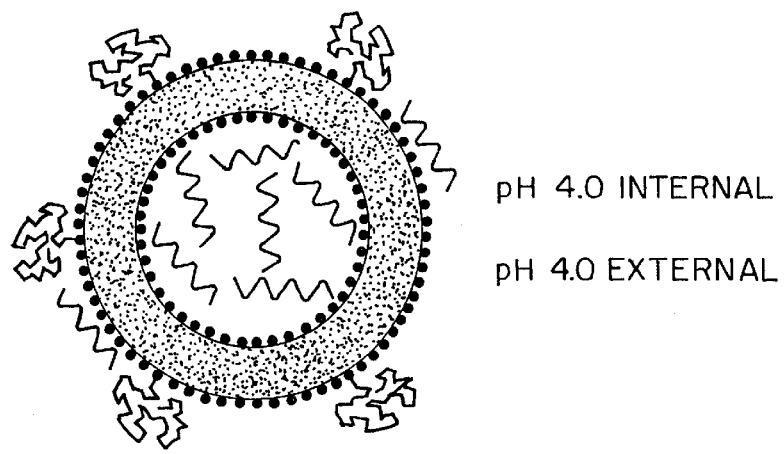
pH 4.0 INTERNAL
pH 4.0 EXTERNAL
COLUMN CHROMATOGRAPHY
1. EXCHANGE pH 4.0 CITRATE FOR pH 7.5 HBS
2. NEUTRALIZE SURFACE DODAP; ANTISENSE RELEASE
3. REMOVAL OF NON-ENCAPSULATED ANTISENSE
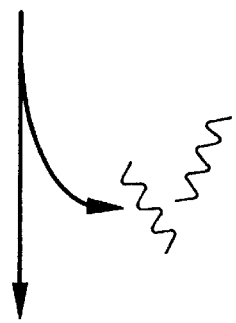
RELEASE OF SURFACE ANTISENSE
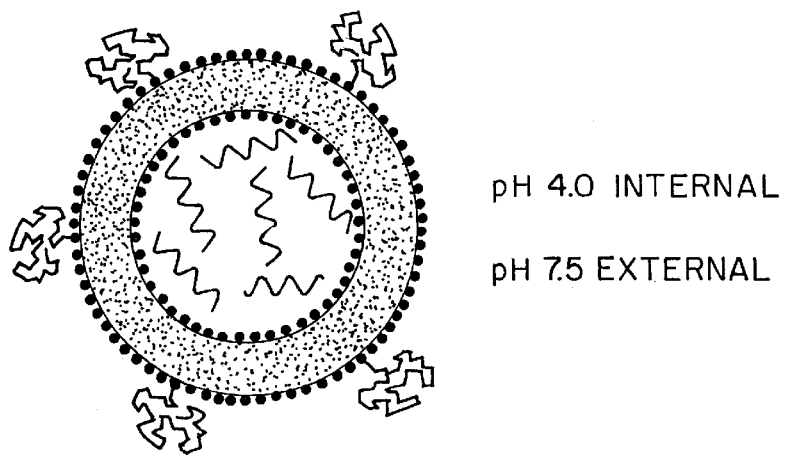
pH 4.0 INTERNAL
pH 7.5 EXTERNAL
FIG. 1

DODAP: AL-1
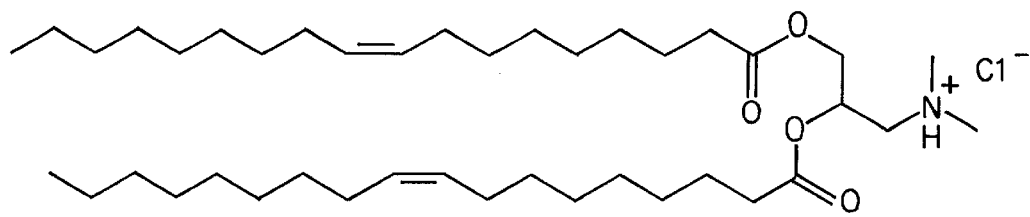
OTHER AMINO LIPIDS:
$R^1$ AND/OR $R^2$ ARE H,
ALKYL OR FATTY ALKYL GROUPS
$R^3$ IS H, LOWER ALKYL.
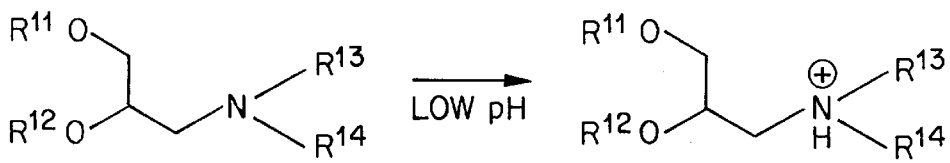
$R^{11}$ AND/OR $R^{12}$ ARE LOWER ALKYL/LOWER ACYL, FATTY ALKYL, FATTY ACYL.
(AT LEAST ONE OF $R^{11}$ OR $R^{12}$ IS A LONG CHAIN ALKYL OR ACYL GROUP)
$R^{13}$ AND $R^{14}$ ARE EACH H, LOWER ALKYL.
FIG. 2A

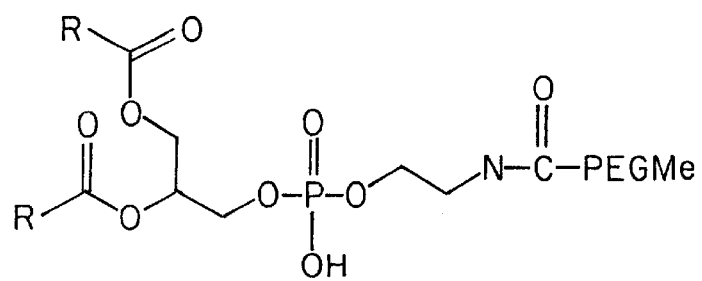
A
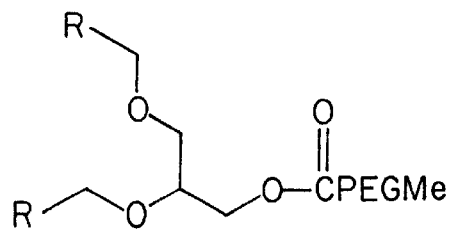
D
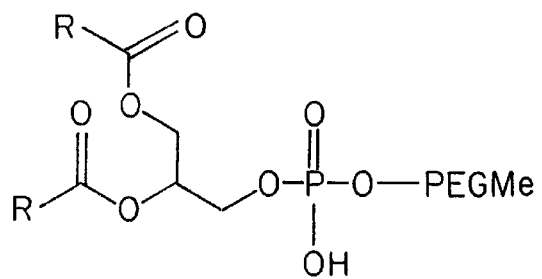
B
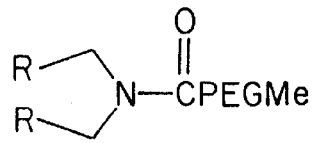
E
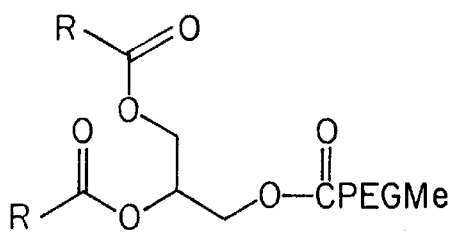
C
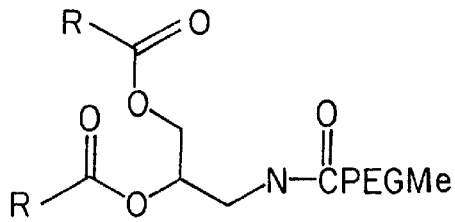
F
FIG. 2B

IMMEDIATELY AFTER REMOVAL OF FREE ANTISENSE

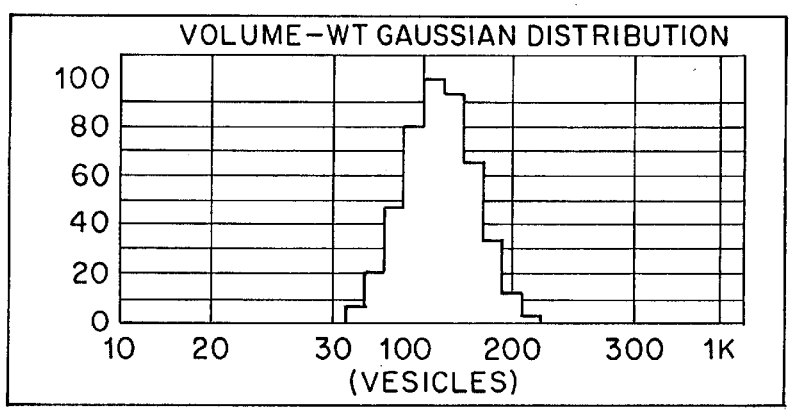

VOLUME WEIGHTING:
MEAN DIAMETER = 119.3 nm
STD DEVIATION = 32.2 nm (27.0 %)
CUMULATIVE RESULTS:
25 % OF DISTRIBUTION < 88.60 nm
50 % OF DISTRIBUTION < 106.74 nm
75 % OF DISTRIBUTION < 127.93 nm
90 % OF DISTRIBUTION < 151.04 nm
99 % OF DISTRIBUTION < 199.22 nm

AFTER 2 MONTH STORAGE AT 4°C

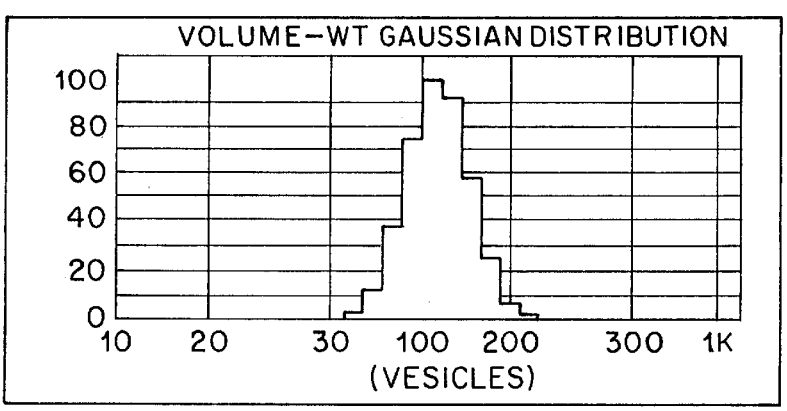

VOLUME WEIGHTING:
MEAN DIAMETER = 114.2 nm
STD DEVIATION = 27.8 nm (24.3%)
CUMULATIVE RESULTS:
25 % OF DISTRIBUTION < 86.96 nm
50 % OF DISTRIBUTION < 102.86 nm
75 % OF DISTRIBUTION < 121.31 nm
90 % OF DISTRIBUTION < 140.78 nm
99 % OF DISTRIBUTION < 183.74 nm

FIG. 7

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 20
      (B) TYPE: nucleic acid
      (C) STRANDEDNESS: single
      (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 1:

TGCATCCCCC AGGCCACCAT      20

(2) INFORMATION FOR SEQ ID NO: 2:

(i) SEQUENCE CHARACTERISTICS:

```
            (A) LENGTH: 20
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 2:

GCCCAAGCTG GCATCCGTCA                                                    20

(2) INFORMATION FOR SEQ ID NO: 3:

(i) SEQUENCE CHARACTERISTICS:
            (A) LENGTH: 15
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 3:

GGTGCTCACT GCGGC                                                         15

(2) INFORMATION FOR SEQ ID NO: 4:

(i) SEQUENCE CHARACTERISTICS:
            (A) LENGTH: 15
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 4:

AACGTTGAGG GGCAT                                                         15

(2) INFORMATION FOR SEQ ID NO: 5:

(i) SEQUENCE CHARACTERISTICS:
            (A) LENGTH: 16
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 5:

TAACGTTGAG GGGCAT                                                        16

(2) INFORMATION FOR SEQ ID NO: 6:

(i) SEQUENCE CHARACTERISTICS:
            (A) LENGTH: 24
            (B) TYPE: nucleic acid
            (C) STRANDEDNESS: single
```

(D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 6:

TATGCTGTGC CGGGGTCTTC GGGC                                             24

(2) INFORMATION FOR SEQ ID NO: 7:

(i) SEQUENCE CHARACTERISTICS:
          (A) LENGTH: 18
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 7:

GTGCCGGGGT CTTCGGGC                                                    18

(2) INFORMATION FOR SEQ ID NO: 8:

(i) SEQUENCE CHARACTERISTICS:
          (A) LENGTH: 18
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 8:

GGACCCTCCT CCGGAGCC                                                    18

(2) INFORMATION FOR SEQ ID NO: 9:

(i) SEQUENCE CHARACTERISTICS:
          (A) LENGTH: 18
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 9:

TCCTCCGGAG CCAGACTT                                                    18

(2) INFORMATION FOR SEQ ID NO: 10:

(i) SEQUENCE CHARACTERISTICS:
          (A) LENGTH: 15
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 10:

CCGTGGTCAT GCTCC                                                        15

(2) INFORMATION FOR SEQ ID NO: 11:

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 11:

CAGCCTGGCT CACCGCCTTG G                                                 21

(2) INFORMATION FOR SEQ ID NO: 12:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 12:

CAGCCATGGT TCCCCCCAAC                                                   20

(2) INFORMATION FOR SEQ ID NO: 13:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 13:

GTTCTCGCTG GTGAGTTTCA                                                   20

(2) INFORMATION FOR SEQ ID NO: 14:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: other nucleic acid (iii) HYPOTHETICAL: no

```
        (iv) ANTI-SENSE: yes (xi) SEQUENCE DESCRIPTION: SEQ ID NO: 14:

TCTCCCAGCG TGCGCCAT                                                   18

(2) INFORMATION FOR SEQ ID NO: 15:

(i) SEQUENCE CHARACTERISTICS:
          (A) LENGTH: 15
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 15:

GTGCTCCATT GATGC                                                      15

(2) INFORMATION FOR SEQ ID NO: 16:

(i) SEQUENCE CHARACTERISTICS:
          (A) LENGTH: 34
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 16:

GAGUUGCUGA UGAGGCCGAA AGGCCGAAAG UCUG                                  34

(2) INFORMATION FOR SEQ ID NO: 17:

(i) SEQUENCE CHARACTERISTICS:
          (A) LENGTH: 15
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (xi) SEQUENCE DESCRIPTION: SEQ ID NO: 17:

GAACGGAGAC GGTTT                                                      15
```

CHARGED THERAPEUTIC AGENTS ENCAPSULATED IN LIPID PARTICLES CONTAINING FOUR LIPID COMPONENTS

This application is a continuation-in-part of U.S. patent application Ser. No. 08/856,374 filed May 14, 1997, now abandoned, which is incorporated herein by reference.

FIELD OF THE INVENTION

This invention relates to compositions comprising a combination of a lipid and a therapeutic agent, particularly to lipid-nucleic acid compositions, for in vivo therapeutic use. In these compositions the therapeutic agent is encapsulated and protected from degradation and clearance in serum. Additionally, the invention provides methods of making the compositions, as well as methods of introducing the nucleic acids into cells using the compositions and treating disease conditions.

BACKGROUND OF THE INVENTION

Therapeutic oligonucleotides, such as antisense oligonucleotides or ribozymes, are short segments of DNA that have been designed to hybridize to a sequence on a specific mRNA. The resulting complex can down-regulate protein production by several mechanisms, including inhibition of mRNA translation into protein and/or by enhancement of RNase H degradation of the mRNA transcripts. Consequently, therapeutic oligonucleotides have tremendous potential for specificity of action (i.e. the down-regulation of a specific disease-related protein). To date, these compounds have shown promise in several in vitro and in vivo models, including models of inflammatory disease, cancer, and HIV (reviewed in Agrawal, *Trends in Biotech.* 14:376–387 (1996)). Antisense can also effect cellular activity by hybridizing specifically with chromosomal DNA. Advanced human clinical assessments of several antisense drugs are currently underway. Targets for these drugs include the genes or RNA products of c-myc, ICAM-1, and infectious disease organisms such as cytomegalovirus, and HIV-1.

One well known problem with the use of therapeutic oligonucleotides having a phosphodiester internucleotide linkage is its very short half-life in the presence of serum or within cells. (Zelphati, O et al. 1993. Inhibition of HIV-1 Replication in Cultured Cells with Antisense Oligonucleotides Encapsulated in Immunoliposomes. Antisense. Res. Dev. 3:323–338; and Thierry, AR et al. pp147–161 in Gene Regulation: Biology of Antisense RNA and DNA (Eds. Erickson, RP and Izant, JG) 1992. Raven Press, NY). No clinical assessment currently employs the basic phosphodiester chemistry found in natural nucleic acids, because of these and other known problems.

This problem has been partially overcome by chemical modifications which reduce serum or intracellular degradation. Modifications have been tested at the internucleotide phosphodiester bridge (i.e. using phosphorothioate, methylphosphonate or phosphoramidate linkages), at the nucleotide base (i.e.5-propynyl-pyrimidines), or at the sugar (i.e. 2'-modified sugars) (Uhlmann E., et al. 1997. Antisense: Chemical Modifications. Encyclopedia of Cancer Vol. X. pp 64–81 Academic Press Inc.). Others have attempted to improve stability using 2'–5' sugar linkages (see U.S. Pat. No. 5,532,130). Other changes have been attempted. However, none of these solutions have proven entirely satisfactory, and in vivo free antisense still has only limited efficacy. Problems remain, such as in the limited ability of some antisense to cross cellular membranes (see, Vlassov, et al., *Biochim. Biophys. Acta* 1197:95–1082 (1994)) and in the problems associated with systemic toxicity, such as complement-mediated anaphylaxis, altered coagulatory properties, and cytopenia (Galbraith, et al., *Antisense Nucl. Acid Drug Des.* 4:201–206 (1994)). Further, as disclosed in U.S. patent application Ser. No. 08/657,753 and counterpart patent application WO 97/46671, both incorporated herein by reference, modified antisense is still highly charged, and clearance from the circulation still takes place within minutes.

To attempt to improve efficacy, investigators have also employed lipid-based carrier systems to deliver chemically modified or unmodified antisense. In Zelphati, O and Szoka, F. C. (1996) J. Contr. Rel. 41:99–119, the authors refer to the use of anionic (conventional) liposomes, pH sensitive liposomes, immunoliposomes, fusogenic liposomes and cationic lipid/antisense aggregates.

None of these compositions successfully deliver phosphodiester antisense for in vivo therapy. In another paper, Zelphati & Szoka note that antisense phosphodiester oligonucleotides associated with cationic lipids have not been active in cell culture in vitro; and that only one study has reported the activity of phosphodiester antisense oligonucleotides complexed to cationic lipids. The authors argue that these findings " . . . necessitate[ ] the use [of -sic] backbone-modified oligonucleotides that are relatively resistant to both intracellular and extracellular nucleases even if a carrier is used to deliver the oligonucleotide into the target cell". (1997. J. Lip. Res. 7(1):31–49 at 34). This finding is corroborated by Bennett, C F. (1995. Intracellular Delivery of Oligonucleotides with Cationic Liposomes. Chp 14 CRC Press) who states at p. 224 that "In contrast, we have been unable to demonstrate inhibition of gene expression by uniform phosphodiester oligodeoxynucleotides directed towards a number of cellular targets in the presence of cationic lipids."

Prior art lipid formulations of modified antisense are also largely ineffective in vivo. They have poor encapsulation efficiency (15% or less for passive encapsulation systems), poor drug to lipid ratios (3% or less by weight), high susceptibility to serum nucleases and rapid clearance from circulation (particularly in the case of cationic lipid/antisense aggregates made from DOTMA, trade-name LIPOFECTIN™), and/or large sized particles (greater than 100 nm), which make them unsuitable for systemic delivery to target sites. No successful in vivo efficacy studies of lipid-encapsulated (nuclease-resistant) modified antisense are known in the prior art.

Two references to unique lipid-antisense compositions that may be significantly nuclease resistant bear consideration. Firstly, the anionic liposome (LPDII) composition of Li, S. and Huang, L (1997. J. Lip. Res. 7(1) 63–75), which encapsulates poly-lysine coated antisense, are said to have 60–70% encapsulation efficiency, but suffer from a large size of around 200 nm and a low drug to lipid ratio of 8% by weight. The effect of these particles in vivo is unknown. Secondly, the Minimal Volume Entrapment (MVE) technique for cardiolipin (anionic) liposomes results in the reasonably high encapsulation efficiency of 45–65% but again the drug:lipid ratio remains very small, approximately 6.5% by weight (see U.S. Pat. No. 5,665,710 to Rahman et al.; Thierry A R, and Takle, G B. 1995, Liposomes as a Delivery System for Antisense and Ribozyme Compounds. in *Delivery Strategies for Antisense Oligonucleotide Therapeutics,* S. Akhtar, ed, CRC Press, Boca Raton, Fla., pp. 199–221; Thierry, A R et al. pp147–161 in Gene Regulation: Biology of Antisense RNA and DNA (Eds. Erickson, R P and Izant, J G) 1992. Raven Press, NY). Note that U.S. Pat. No. 5,665,710 also discloses encapsulation efficiencies of 60–90% for tiny, medically useless amounts of antisense (0.1 ug), where the drug to lipid ratio must be very low.

It is an observation of the inventors that a wide variety of prior art lipid compositions used for conventional drugs could be tested for efficacy in the antisense field, but the improvement (over free antisense) for in vivo efficacy is not known. In this regard, it is noted that although lipid compositions assertedly for use as drug carriers were disclosed by Bailey and Cullis (U.S. Pat. No. 5,552,155; and (1994) Biochem. 33(42):12573–12580), they did not disclose formulations of any bioactive compounds with these lipids, and did not suggest their utility for high efficiency loading of polyanionic species.

What is needed in the art are improved lipid-therapeutic oligonucleotide compositions which are suitable for therapeutic use. Preferably these compositions would encapsulate nucleic acids with high-efficiency, have high drug:lipid ratios, be encapsulated and protected from degradation and clearance in serum, and/or be suitable for systemic delivery. The present invention provides such compositions, methods of making the compositions and methods of introducing nucleic acids into cells using the compositions and methods of treating diseases.

SUMMARY OF THE INVENTION

In accordance with the invention, charged therapeutic agents are packaged into lipid-encapsulated therapeutic agent particles using a method comprising the steps of:

(a) combining a mixture of lipids comprising at least a first lipid component and a second lipid component with a buffered aqueous solution of a charged therapeutic agent to form an intermediate mixture containing lipid-encapsulated therapeutic particles, and (b) changing the pH of the intermediate mixture to neutralize at least some exterior surface charges on said lipid-nucleic acid particles to provide at least partially-surface neutralized lipid-encapsulated therapeutic agent particles. The first lipid component is selected from among lipids containing a protonatable or deprotonatable group that has a pKa such that the lipid is in a charged form at a first pH and a neutral form at a second pH. The buffered solution has a pH such that the first lipid component is in its charged form when in the buffered solution, and the first lipid component is further selected such that the charged form is cationic when the therapeutic agent is anionic in the buffered solution and anionic when the therapeutic agent is cationic in the buffered solution. The second lipid component being selected from among lipids that prevent particle aggregation during lipid-nucleic acid particle formation. The method the invention is particularly useful for preparation of lipid-encapsulated nucleic acids, for example antisense nucleic acids or ribozyme.

BRIEF DESCRIPTION OF THE DRAWINGS

FIG. 1 illustrates a neutralization step which releases surface-bound antisense from the lipid-nucleic acid compositions according to the present invention.

FIGS. 2A and 2B illustrate certain lipid components which are useful in the present inventive methods. FIG. 2A illustrates several groups of amino lipids including the chemical structure of DODAP. FIG. 2B illustrates groups of PEG-modified lipids.

FIG. 7 illustrates the quasi-elastic light scattering analysis of encapsulated liposomal antisense. The size distribution of a liposomal preparation of antisense was determined by quasi-elastic light scattering (QELS) immediately after removal of the free antisense (A), and after storage of the preparation for 2 months at 4° C. (B), using a Nicomp Model 370 sub-micron particle sizer.

EPC:CHOL liposomes containing encapsulated antisense are included for comparison.

Figure 9:
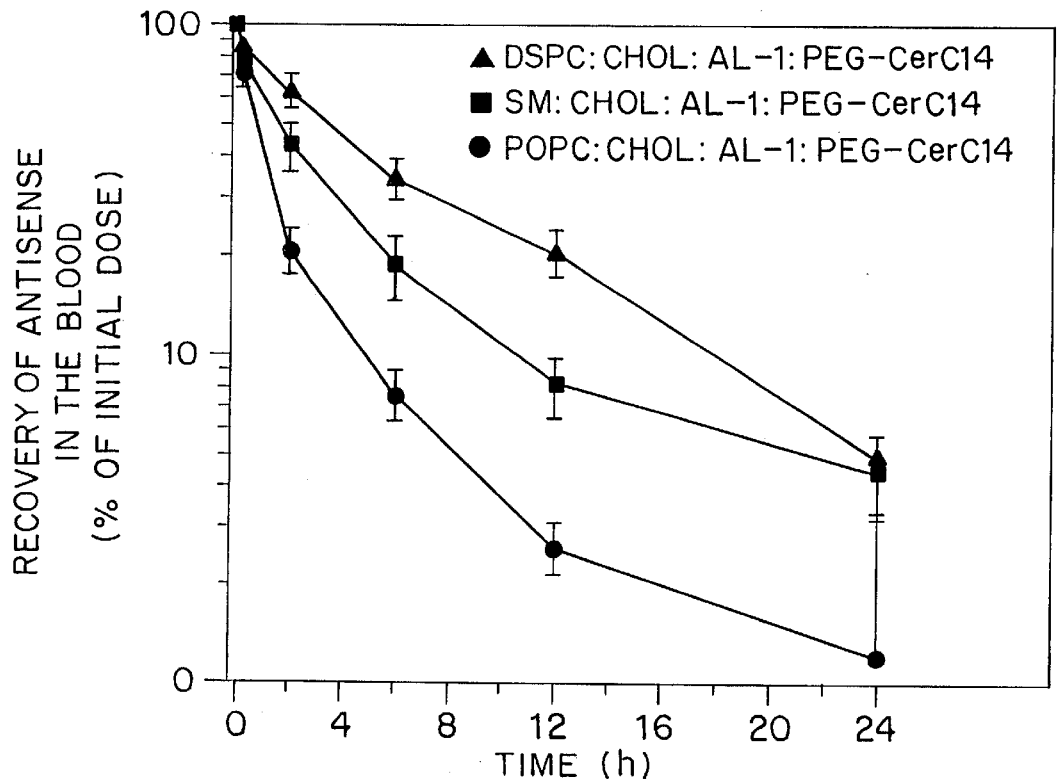

FIG. 9 illustrates the plasma clearance of encapsulated antisense. Encapsulated liposomal antisense was prepared using the ethanol-citrate procedure as described in "Material and Methods". Initial lipid and antisense concentrations were 9.9 and 2 mg/mL, respectively. Liposomal formulations were composed of X:CHOL:DODAP:PEG-CerC14 (25:45:20:10), where X represents either distearoylphosphatidylcholine (DSPC), sphingomyelin (SM), or palmitoyloleoylphosphatidylcholine (POPC). The formulations contained a lipid label ($[^{14}C]$-cholesterylhexadecylether) and $[^3H]$-antisense and were injected (200 μL) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques.

Figure 10:
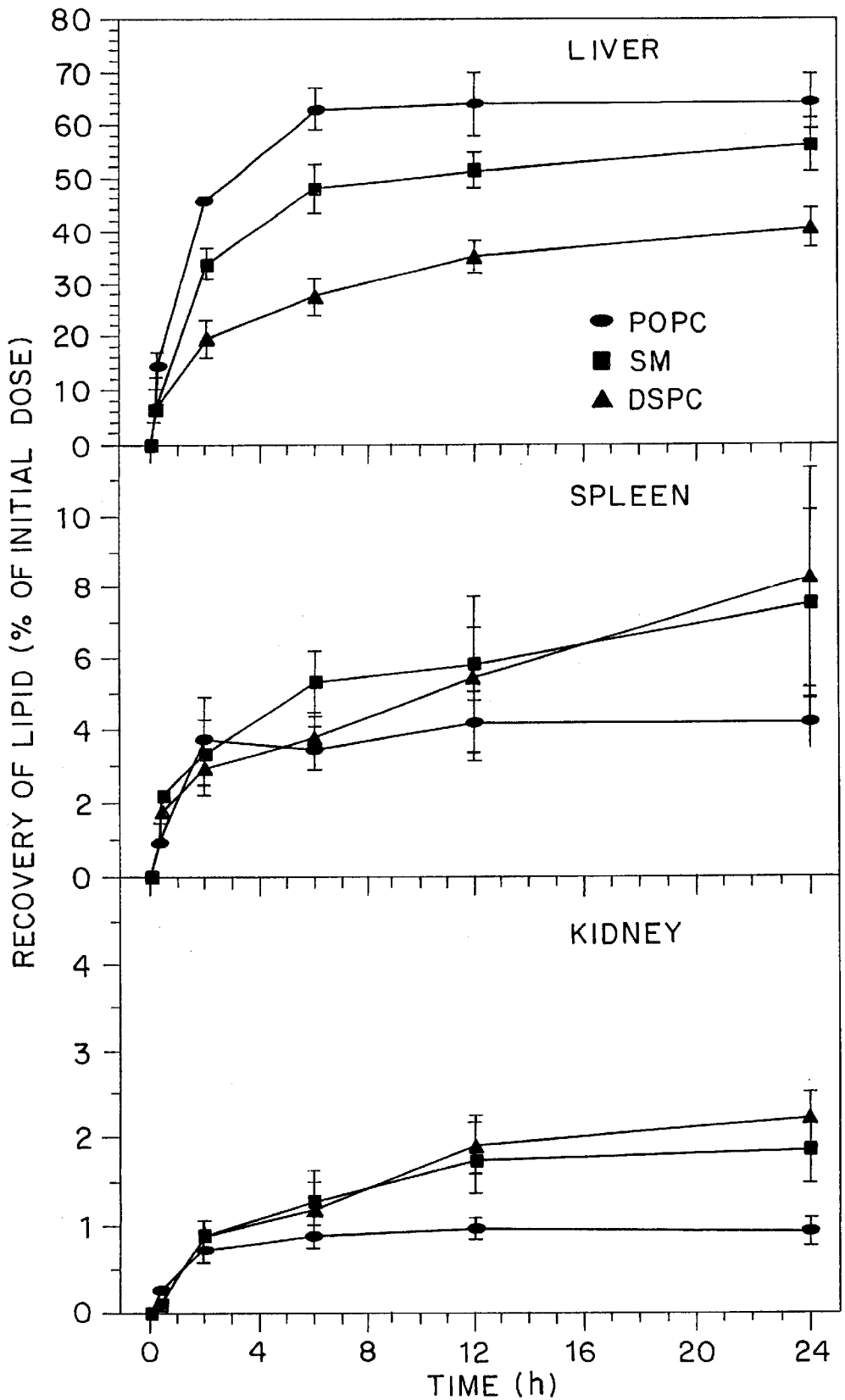

FIG. 10 illustrates the biodistribution of encapsulated antisense. Encapsulated liposomal antisense was prepared using the ethanol-citrate procedure as described in "Material and Methods". Initial lipid and antisense concentrations were 9.9 and 2 mg/mL, respectively. Liposomal formulations were composed of X:CHOL:DODAP:PEG-CerC14 (25:45:20:10), where X represents either distearoylphosphatidylcholine (DSPC), sphingomyelin (SM), or palmitoyloleoylphosphatidylcholine (POPC). The formulations contained a lipid label ($[^{14}C]$-cholesterylhexadecylether) and $[^3H]$-antisense and were injected (200 μL) intravenously via the lateral tail vein of female (20–25 g) ICR mice at a lipid dose of 120 mg/kg. Mice were terminated by cervical dislocation and the organs were recovered and processed as described in "Materials and Methods". Lipid and antisense recoveries were determined by standard scintillation counting techniques.

Figure 11:
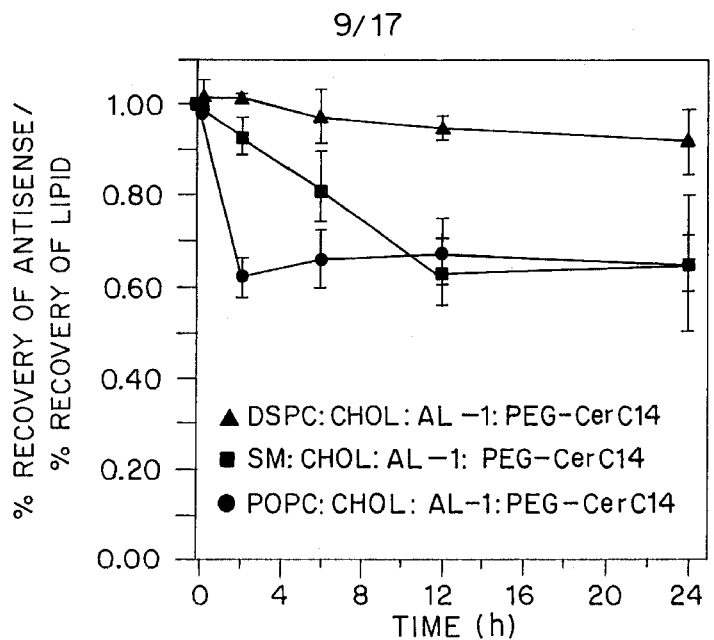

FIG. 11 illustrates the differential release rates of antisense in plasma. Encapsulated liposomal antisense was prepared using the ethanol-citrate procedure as described in "Material and Methods". Initial lipid and antisense concentrations were 9.9 and 2 mg/mL, respectively. Liposomal formulations were composed of X:CHOL:DODAP:PEG-CerC14 (25:45:20:10), where X represents either distearoylphosphatidylcholine (DSPC), sphingomyelin (SM), or palmitoyloleoylphosphatidylcholine (POPC). The formulations contained a lipid label ($[^{14}C]$-cholesterylhexadecylether) and $[^3H]$-antisense and were injected (200 μL) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques. Release rates were determined by measuring the [3H]/[14C] ratio over time.

Figure 12:
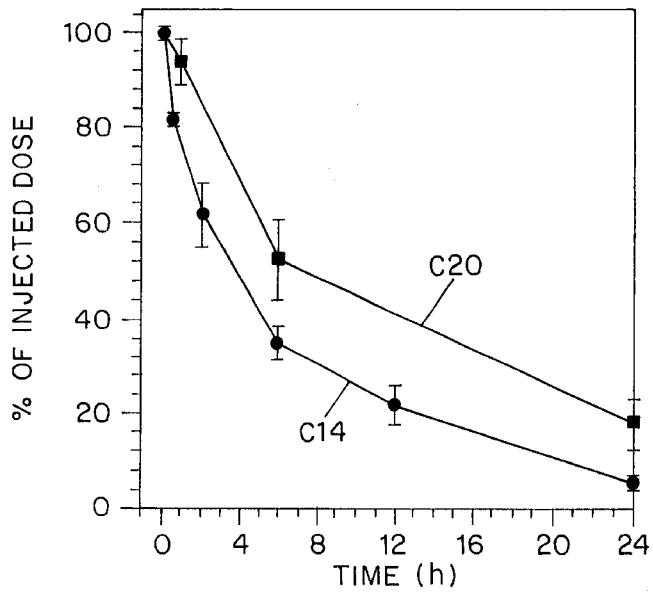

FIG. 12 illustrates the influence of PEG-acyl chain lengths on plasma clearance of encapsulated antisense. Encapsulated liposomal antisense was prepared using the ethanol-citrate procedure as described in "Material and Methods". Initial lipid and antisense concentrations were 9.9 and 2 mg/mL, respectively. Liposomal formulations were composed of DSPC:CHOL:DODAP:PEG-CerC14 or C20 (25:45:20:10). The formulation contained a lipid label ($[^{14}C]$-cholesterylhexadecylether) and $[^3H]$-antisense and were injected (200 μL) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques.

Figure 13:
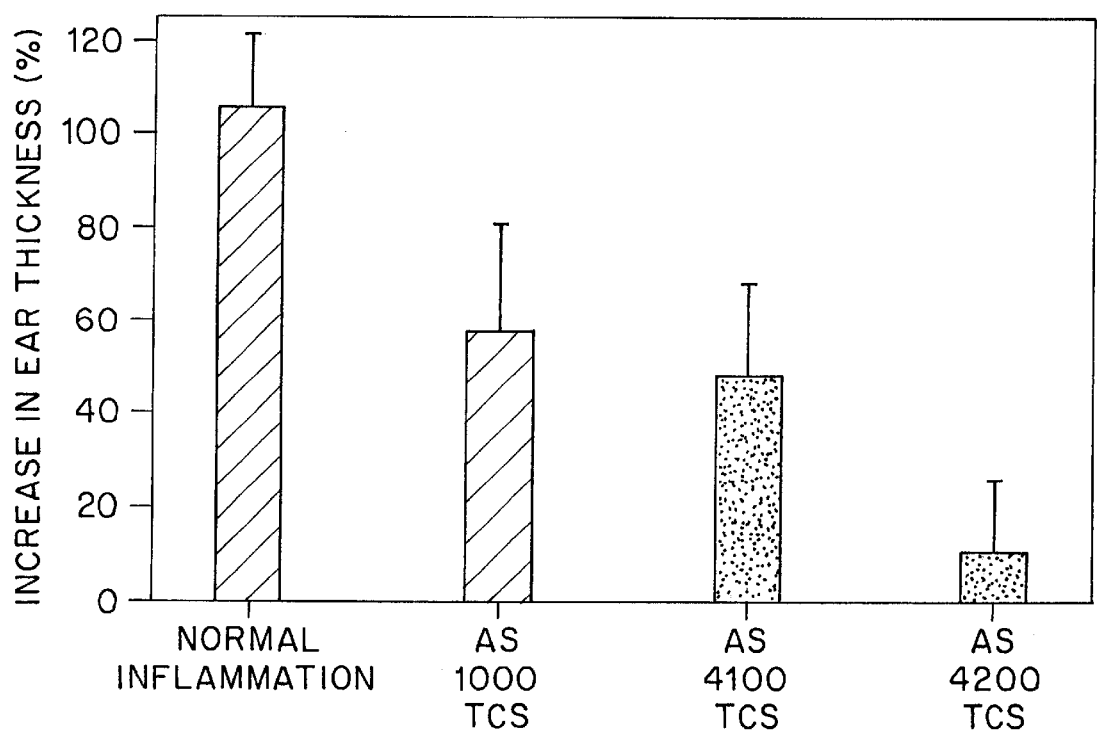

FIG. 13 illustrates the enhanced efficacy of liposomal antisense containing DODAP—ear swelling. Inflamed mice were treated at the time of ear challenge with a 30 mg/kg i.v. dose of either HBS (no oligo), EPC:CHOL liposomes with entrapped PS 3082 (identified as AS 1000), POPC:CHOL:DODAP:PEG-CerC14 with entrapped PS 3082 (identified as 4100), or DSPC:CHOL:DODAP:PEG-CerC14 with entrapped PS 3082 (identified as 4200). Ear swelling was measured at 24 hours after initiating inflammation using an engineer's micrometer.

Figure 14:
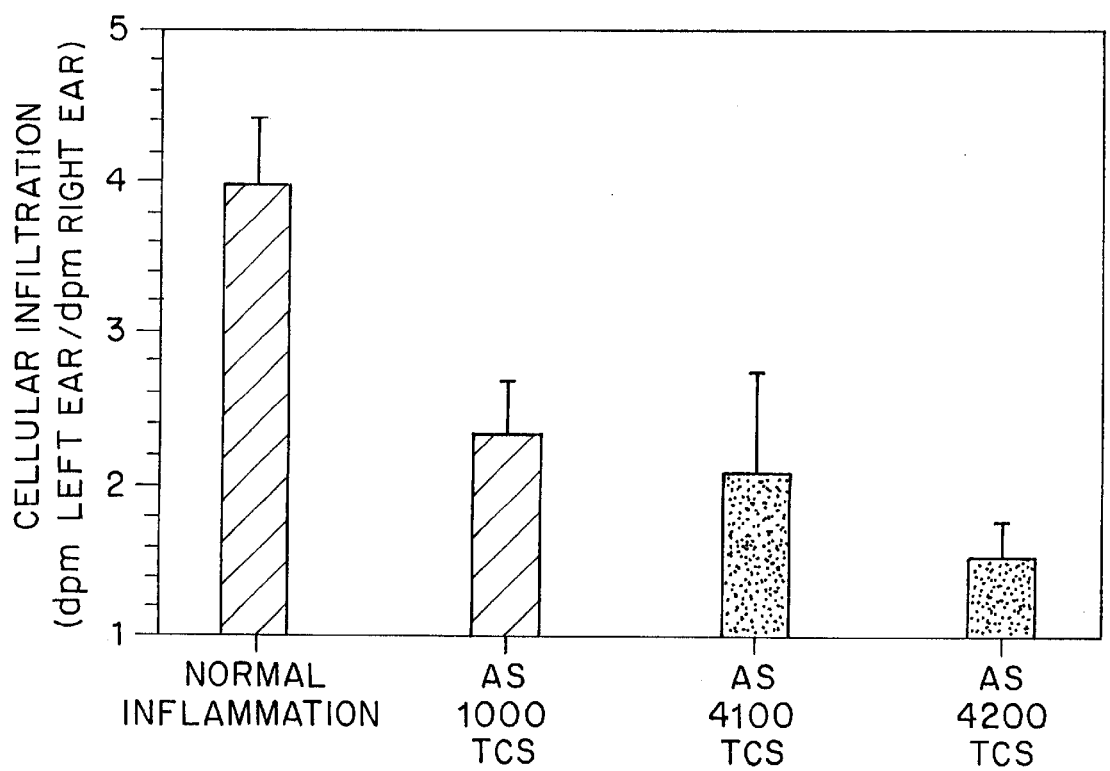

FIG. 14 illustrates the enhanced efficacy of liposomal antisense containing DODAP—cellular infiltration. Mice received 10 μCi of $[^3H]$-methylthymidine, i.p., 24 hours before initiating inflammation. Inflamed mice were treated at the time of ear challenge with a 30 mg/kg i.v. dose of either HBS (no oligo), EPC:CHOL liposomes with entrapped PS 3082 (identified as AS 1000), POPC:CHOL:DODAP:PEG-CerC14 with entrapped PS 3082 (identified as 4100), or DSPC:CHOL:DODAP:PEG-CerC14 with entrapped PS 3082 (identified as 4200). Cell infiltration was monitored by measuring the radioactivity in the "challenged ear" versus the non-treated ear. Results are expressed as the ratio of radioactivity in the left (challenged ear) versus right ear.

Figure 15:
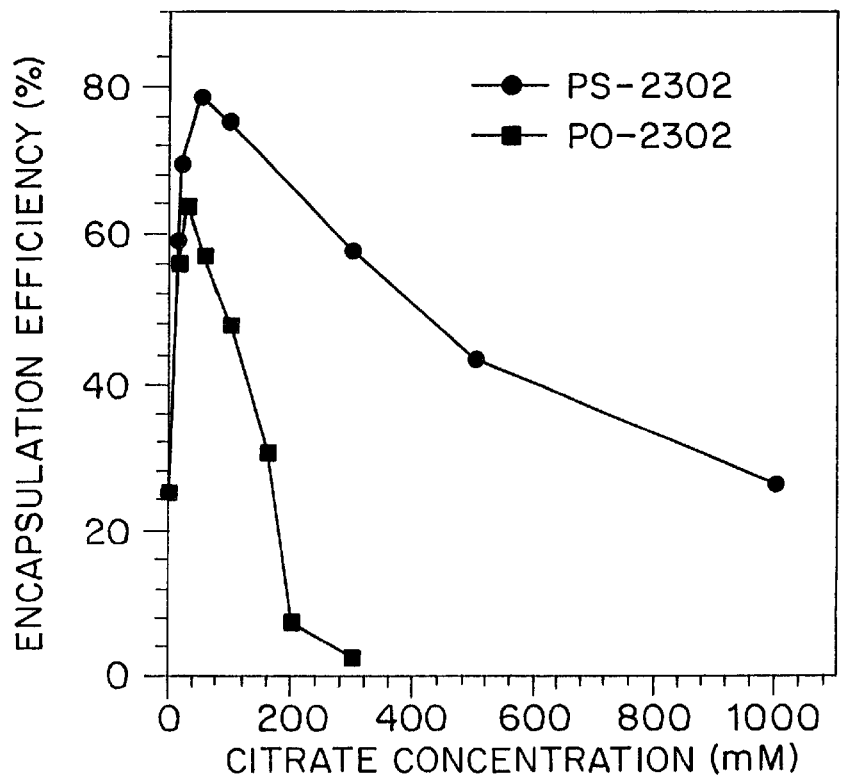

FIG. 15 shows asymmetric loading of lipid-encapsulated-nucleic acid particles in accordance with the invention.

Figure 16:
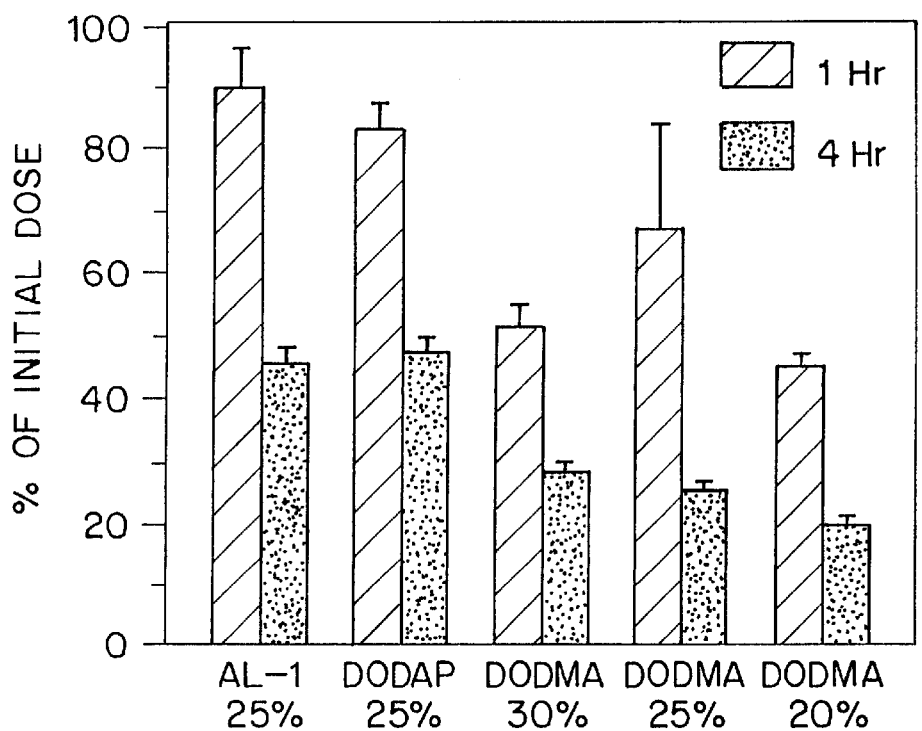

FIG. 16 shows clearance of lipid-encapsulated antisense particles formulated with several amino lipids at different levels.

Figure 17:
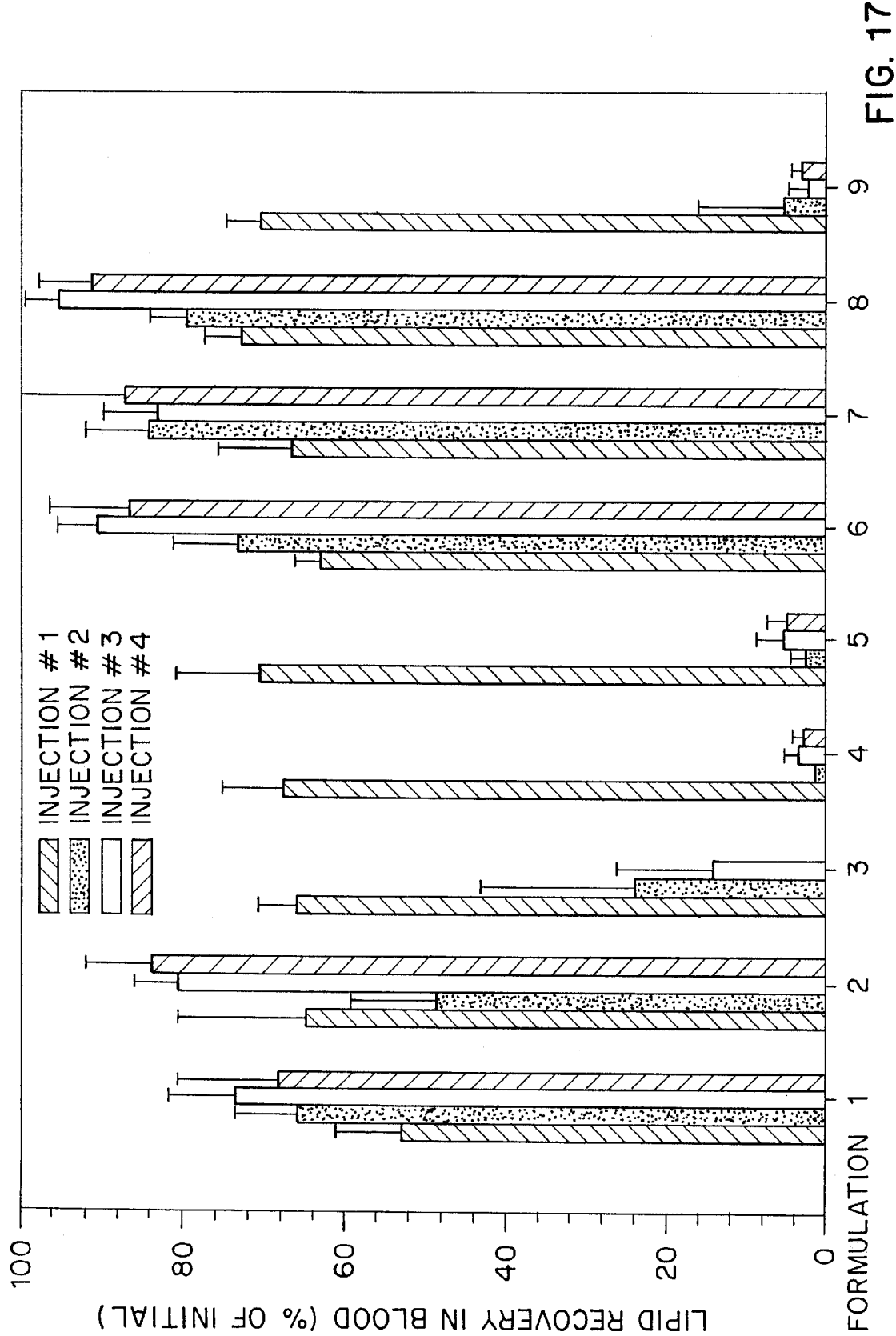

FIG. 17 shows blood levels of antisense-containing particles after repeat dosages.

Figure 18:
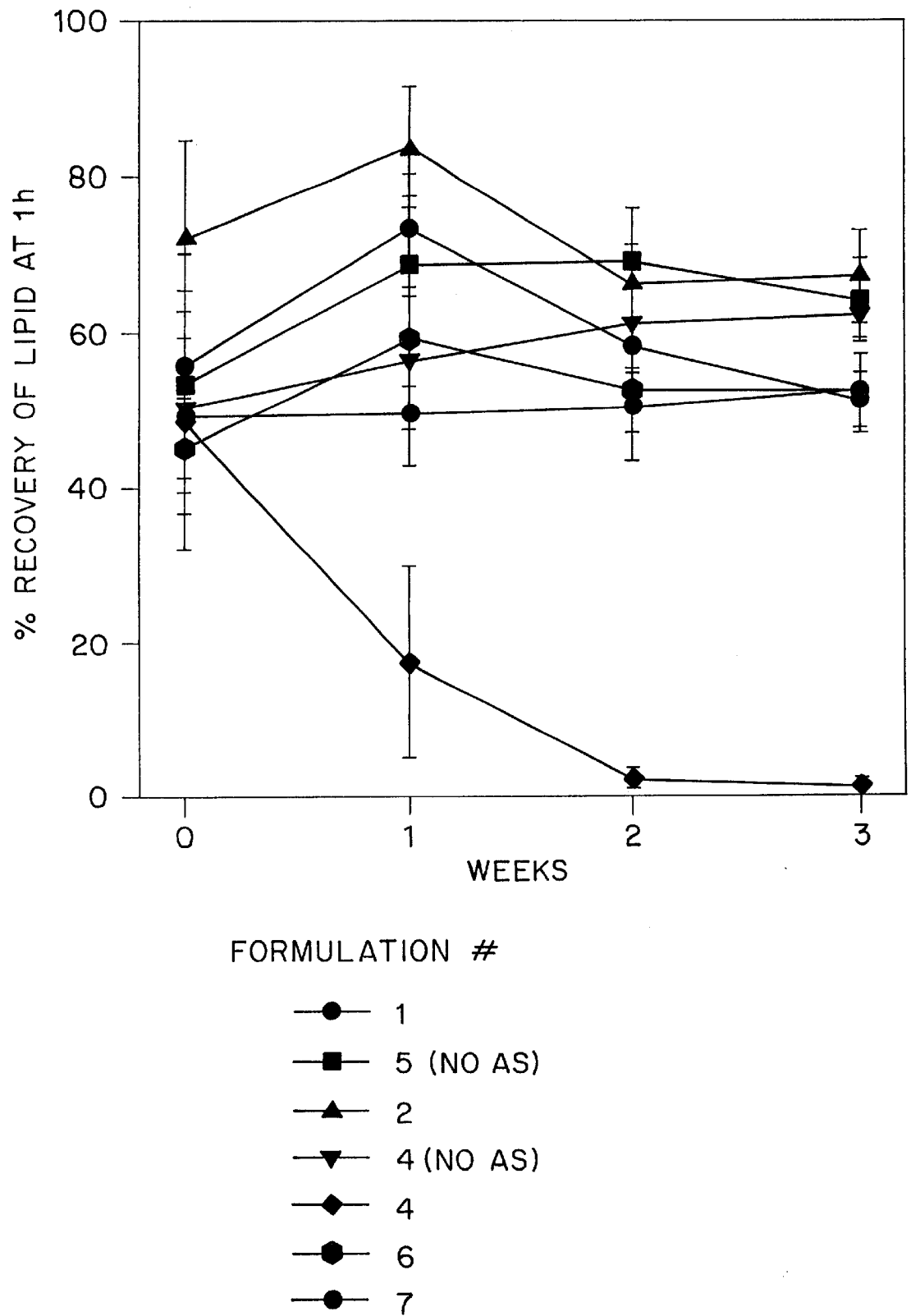

FIG. 18 shows blood levels of antisense-containing particles after repeat dosages.

Figure 19:
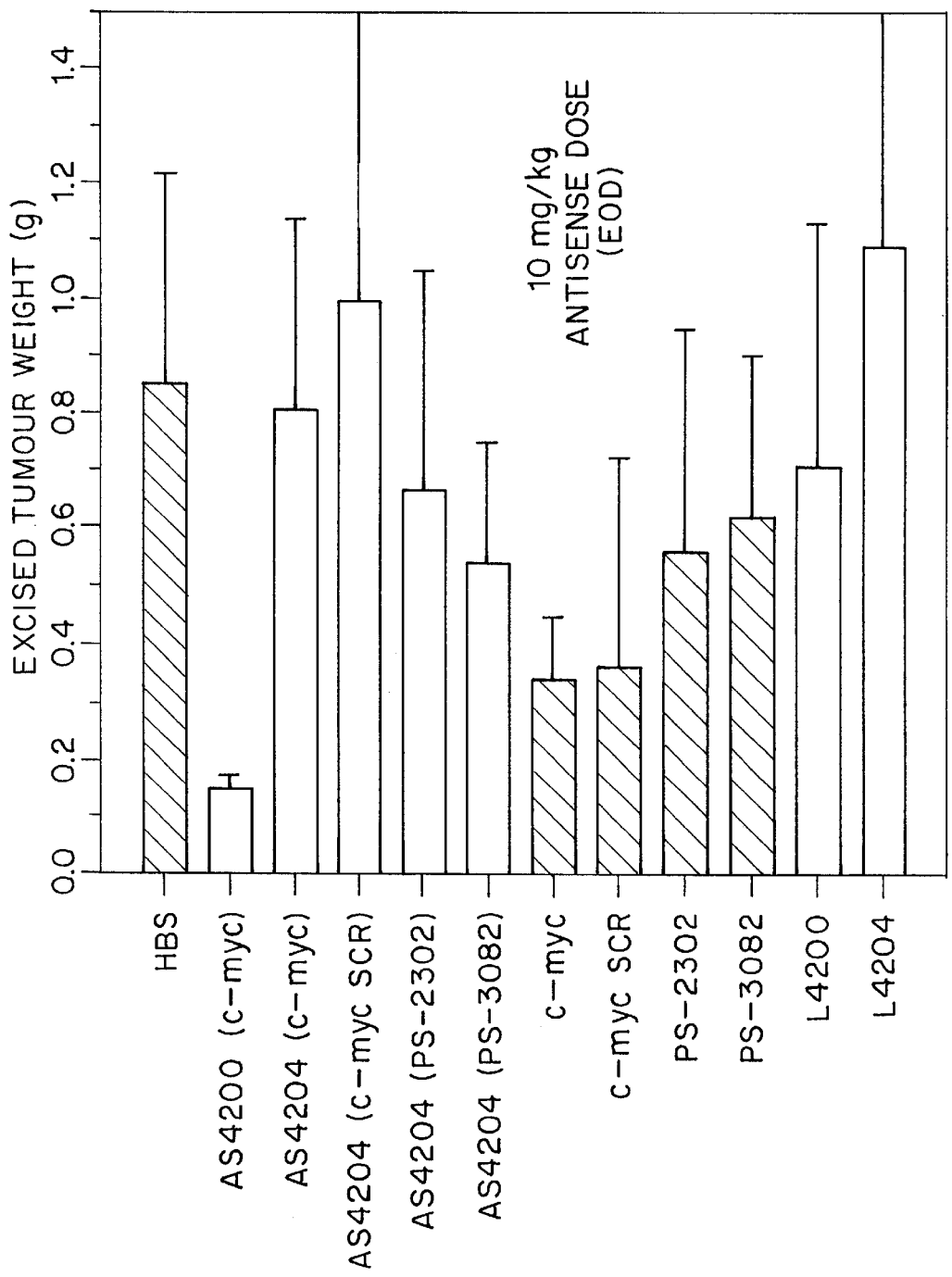

FIG. 19 illustrates results of a study on the in vivo efficacy of lipid-encapsulated antisense particles in accordance with the invention in a mouse tumor model.

Figure 20:
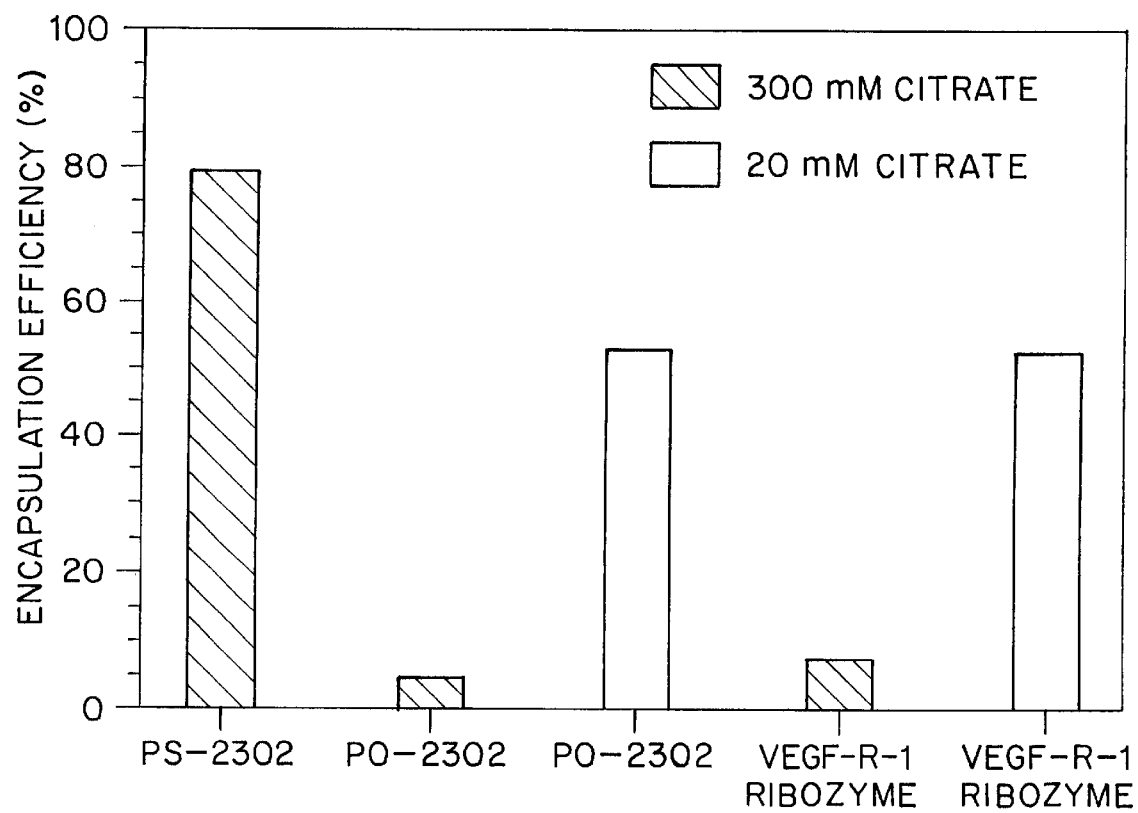

FIG. 20 shows encapsulation efficiency results for lipid-encapsulated therapeutic agent particles in accordance with the invention.

Figure 21:
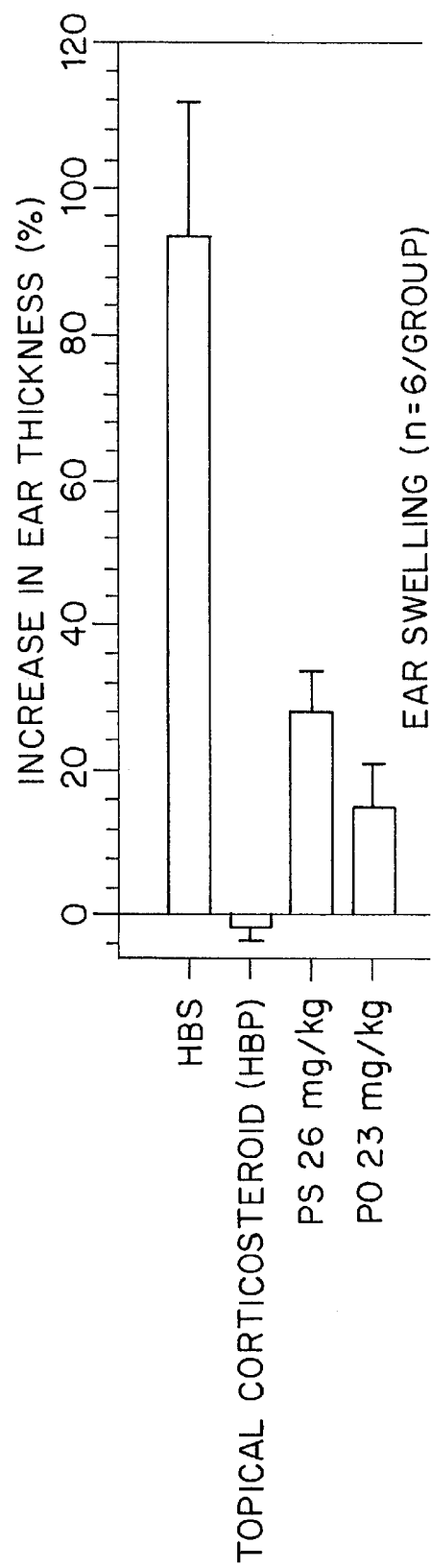

FIG. 21 shows results for studies on the use of murine ICAM1 in an ear inflammation model.

Figure 22:
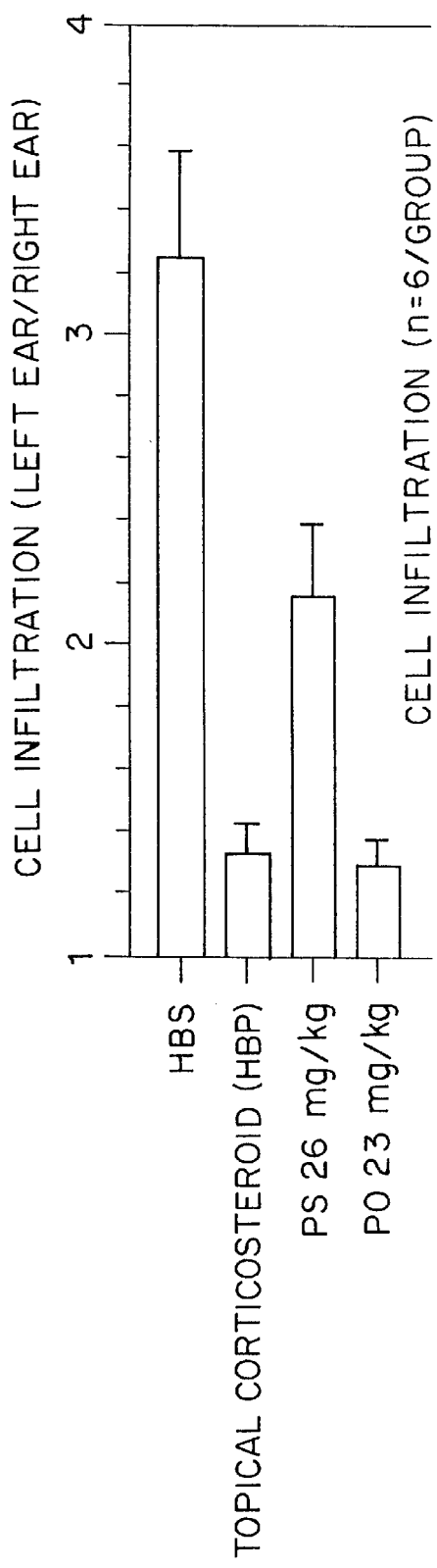

FIG. 22 shows results for studies on the use of murine ICAM1 in an ear inflammation model.

Figure 23:
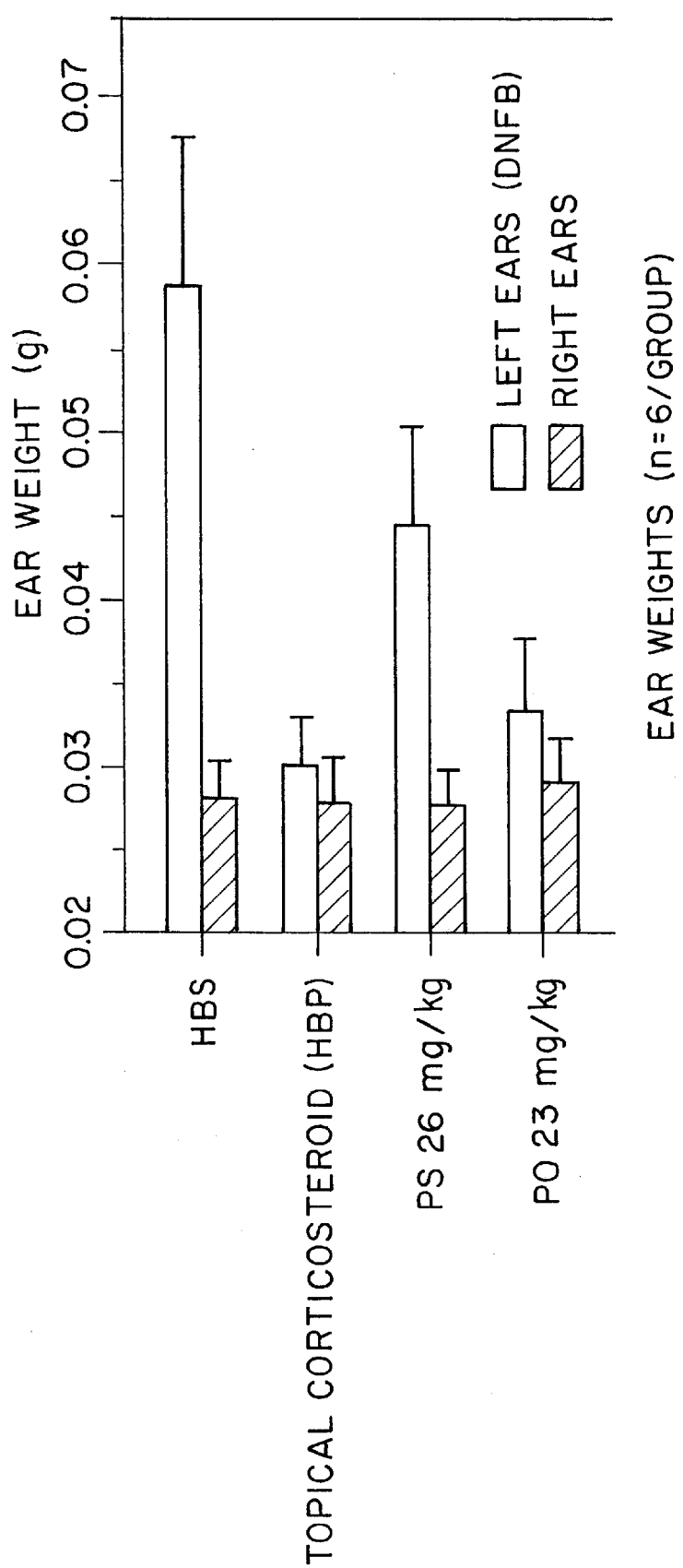

FIG. 23 shows results for studies on the use of murine ICAM1 in an ear inflammation model.

DETAILED DESCRIPTION OF THE INVENTION

Contents

I. Glossary
II. General
III. Methods of Preparing Liposome/Nucleic Acid Complexes
IV. Pharmaceutical Preparations
V. Methods of Introducing the Lipid-Encapsulated Therapeutic Agents Into Cells
VI. Examples
VII. Conclusion I. Glossary Abbreviations and Definitions The following abbreviations are used herein: ATTA, N-(ω-N'-acetoxy-octa(14'amino-3',6',9',12'- tetraoxatetradecanoyl)); CHE, cholesteryl-hexadecylether; CHOL, cholesterol; DODAP or AL-1, 1,2-dioleoyloxy-3-dimethylaminopropane (and its protonated ammonium form); DODMA, N-(1-(2,3-Dioleoyloxy) propyl)-N,N,-dimethyl ammonium chloride; DSPC, distearoylphosphatidylcholine; EPC, egg phosphatidylcholine; HBS, HEPES-buffered saline; HEPES, N-2-hydroxyethylpiperazine-N'-2-ethanesulphonic acid; MES, 2-(N-morpholino)ethane sulfonic acid; PS 3082, murine ICAM-1 phosphorothioate oligodeoxynucleotide having the sequence: TGCATC-CCCCAGGCCACCAT (SEQ ID No. 1); NaCl, sodium chloride; OLIGREEN™, a dye that becomes fluorescent when interacting with an oligonucleotide; PEG-CerC20, polyethylene glycol coupled to a ceramide derivative with 20 carbon acyl chain; POPC, palmitoyloleoylphophatidylcholine; SM, sphingomyelin; DOPE, 1,2-dioleoyl-sn-3-phosphoethanolamine.

"Lipid-therapeutic agent particle" means a particle comprising lipids and a charged (cationic or anionic) therapeutic agent. "Lipid-therapeutic nucleic acid particle" means a particle comprising a lipid and a therapeutic nucleic acid.

"Lipid-encapsulated therapeutic agent (nucleic acid) particle" means a lipid-therapeutic agent particle wherein less than 50% and preferably less than 10% of the therapeutic agent (nucleic acid) is detectable on the external surface of the particle or in the buffer external to the particle. In the case of nucleic acids, the amount of encapsulated versus unencapsulated nucleic acid can be assayed by fluorescence assays or nuclease assays as described herein. Comparable assays can be used for other types of therapeutic agents.

"Therapeutically effective amount" means an amount which provides a therapeutic benefit. For antisense oligonucleotide this means generally 0.5 to 50 mg/kg of body weight, but when delivered in a lipid particle formulation, a below-toxic amount of lipid must be used.

"Lipid exchange out of particle" and the rate of this exchange is fully explained in U.S. patent application Ser. No. 08/486,214, filed Jun. 7, 1995, now U.S. Pat. No. 5,820,873, and U.S. patent application Ser. No. 08/485,608, filed Jun. 7, 1995, now U.S. Pat. No. 5,885,613, and PCT Patent publications WO 96/10391 and WO 96/10392, which are all incorporated herein by reference. Lipid exchange into the surrounding medium is possible for lipids which are reversibly associated with the lipid particle membrane. Each lipid has a characteristic rate at which it will exchange put of a particle which depends on a variety of factors including acyl chain length, saturation, head group size, buffer composition and membrane composition.

"Disease site" is the site in an organism which demonstrates or is the source of a pathology. The disease site may be focused, as in a site of neoplasm or inflammation, or may be diffuse as in the case of a non-solid tumor. "Administration at a site which is distal to the disease site" means that delivery to the disease site will require some kind of systemic delivery, either by blood or lymph circulation, or other fluid movement inside the organism.

The term "transfection" as used herein, refers to the introduction of polyanionic materials, particularly nucleic acids, into cells. The polyanionic materials can be in the form of DNA or RNA which is linked to expression vectors to facilitate gene expression after entry into the cell. Thus the polyanionic material or nucleic acids used in the present invention is meant to include DNA having coding sequences for structural proteins, receptors and hormones, as well as transcriptional and translational regulatory elements (i.e., promoters, enhancers, terminators and signal sequences) and vector sequences. Methods of incorporating particular nucleic acids into expression vectors are well known to those of skill in the art, but are described in detail in, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

The term "physiological pH" refers to pH levels conventionally encountered in serum or blood. In general, this will be in the range of pH 7.2 to 7.5. Preferred protonatable or deprotonatable lipids have a pKa such that they are substantially neutral at this pH, i.e., a pKa of about 4 to 7 in the case of an amino lipid.

II. General

The present invention relates to methods and compositions for producing lipid-encapsulated therapeutic agent particles in which charged therapeutic agents are encapsulated within a lipid layer. The invention is applicable to both anionic and cationic therapeutic agents, including polyanionic nucleic acids, polyanionic proteins or peptides, cytokines and heparin, and cationic proteins and peptides. The invention is principally demonstrated herein with reference to polyanionic nucleic acids as the therapeutic agent, which is a preferred embodiment, but the same principles can be readily extended to other polyanionic or to cationic therapeutic agents.

To evaluate the quality of a lipid/nucleic acid formulation the following criteria, among others, may be employed:
  drug to lipid ratio;
  encapsulation efficiency;
  nuclease resistance/serum stability; and
  particle size.

High drug to lipid rations, high encapsulation efficiency, good nuclease resistance and serum stability and controllable particle size, generally less than 200 nm in diameter are desirable In addition, the nature of the nucleic acid polymer is of significance, since the modification of nucleic acids in an effort to impart nuclease resistance adds to the cost of therapeutics while in many cases providing only limited resistance. The present invention provides lipid-nucleic acid particles and methods for preparing lipid-nucleic acid formulations which are far superior to the art according to these criteria.

Unless stated otherwise, these criteria are calculated in this specification as follows:

drug to lipid ratio: The amount of drug (therapeutic agent) in a defined volume of preparation divided by the amount of lipid in the same volume. This may be on a mole per mole basis or on a weight per weight basis, or on a weight per mole basis. For final, administration-ready formulations, the drug:lipid ratio is calculated after dialysis, chromatography and/or enzyme (e.g., nuclease) digestion has been employed to remove as much of the external therapeutic agent (e.g., nucleic acid) as possible. Drug:lipid ratio is a measure of potency of the formulation, although the highest possible drug:lipid ratio is not always the most potent formulation;

encapsulation efficiency: the drug to lipid ratio of the starting mixture divided by the drug to lipid ratio of the final, administration competent formulation. This is a measure of relative efficiency. For a measure of absolute efficiency, the total amount of therapeutic agent (nucleic acid) added to the starting mixture that ends up in the administration competent formulation, can also be calculated. The amount of lipid lost during the formulation process may also be calculated. Efficiency is a measure of the wastage and expense of the formulation;

nuclease resistance/serum stability: the ability of the formulation to protect the nucleic acid therapeutic agents from nuclease digestion either in an in vitro assay, or in circulation. Several standard assays are detailed in this specification. Encapsulated particles have much greater nuclease resistance and serum stability than lipid-antisense aggregates such as DOTMA/DOPE (LIPOFECTIN™) formulations; and size: the size of the particles formed. Size distribution may be determined using quasi-elastic light scattering (QELS) on a Nicomp Model 370 sub-micron particle sizer. Particles under 200 mn are preferred for distribution to neo-vascularized (leaky) tissues, such as neoplasms and sites of inflammation.

The methods and composition of the invention make use of certain lipids which can be present in both a charged and an uncharged form. For example, amino lipids which are charged at a pH below the $pK_a$ of the amino group and substantially neutral at a pH above the $pk_a$ can be used in a two-step process. First, lipid vesicles can be formed at the lower pH with (cationic) amino lipids and other vesicle components in the presence of nucleic acids. In this manner the vesicles will encapsulate and entrap the nucleic acids. Second, the surface charge of the newly formed vesicles can be neutralized by increasing the pH of the medium to a level above the $pK_a$ of the amino lipids present, i.e., to physiological pH or higher. Particularly advantageous aspects of this process include both the facile removal of any surface adsorbed nucleic acid and a resultant nucleic acid delivery vehicle which has a neutral surface. Liposomes or lipid particles having a neutral surface are expected to avoid rapid clearance from circulation and to avoid certain toxicities which are associated with cationic liposome preparations.

It is further noted that the vesicles formed in this manner provide formulations of uniform vesicle size with high content of nucleic acids. Additionally, the vesicles are not aggregate complexes, but rather are large unilamellar vesicles having a size range of from about 70 to about 200 nm, more preferably about 90 to about 130 nm.

Without intending to be bound by any particular theory, it is believed that the very high efficiency of nucleic acid encapsulation is a result of electrostatic interaction at low pH. FIG. 1 provides an illustration of the processes described herein. More particularly, this figure illustrates a lipid-nucleic acid composition of amino lipids and PEG-modified lipids having encapsulated antisense nucleic acid and surface-bound antisense nucleic acid. At acidic pH (shown as pH 4.0), the surface is charged and binds a portion of the antisense through electrostatic interactions. When the external acidic buffer is exchanged for a more neutral (pH 7.5, HBS) buffer, the surface of the lipid particle or liposome is neutralized, resulting in release of the antisense nucleic acid.

Encapsulation efficiency results in FIG. 15 show a further unexpected benefit of the invention. As shown in the figure, for both phosphorothioate (PS-2302) and phosphodiester (PO-2302) formulations it is possible to obtain encapsulation efficiencies—i.e., the amount of nucleic acid that ends up on the inside of the particle—that are greater than 50%. Phosphodiesters achieve well over 60%, and phosphorothioates can be at least up to 80% encapsulated. The asymmetry of loading is surprising, given that in the simplest model of loading large unilamellar vesicles (LUV's) the therapeutic agent (nucleic acid) would be equally likely to associate with cationic charges on the inside and outside of the particle. A 1:1 distribution (inside to outside) would suggest that the 50% on the outside should be removed upon neutralization of the outside surface charges, such that 50% efficiency would be the theoretical upper limit. Through some unclear mechanism, however, the invention surprisingly provides an active process whereby the majority of the therapeutic agent (nucleic acid) ends up protected on the inside of the particles.

III. Methods of Preparing Lipid/Therapeutic Agent (Nucleic Acid) Formulations

In view of the above, the present invention provides methods of preparing lipid/nucleic acid formulations. In the methods described herein, a mixture of lipids is combined with a buffered aqueous solution of nucleic acid to produce an intermediate mixture containing nucleic acid encapsulated in lipid particles wherein the encapsulated nucleic acids are present in a nucleic acid/lipid ratio of about 10 wt % to about 20 wt %. The intermediate mixture may optionally be sized to obtain lipid-encapsulated nucleic acid particles wherein the lipid portions are large unilamellar vesicles, preferably having a diameter of 70 to 200 nm, more preferably about 90 to 130 nm. The pH is then raised to neutralize at least a portion of the surface charges on the lipid-nucleic acid particles, thus providing an at least partially surface-neutralized lipid-encapsulated nucleic acid composition.

The mixture of lipids includes at least two lipid components: a first lipid component that is selected from among lipids which have a pKa such that the lipid is cationic at pH below the pKa and neutral at pH above the pKa, and a second lipid component that is selected from among lipids that prevent particle aggregation during lipid-nucleic acid particle formation.

The first lipid component of is a lipid (or a mixture of lipid species with similar properties) which has at least one protonatable or deprotonatable group, such that the lipid is charged at a first pH (cationic or anionic, depending on the nature and pKa of the protonatable or deprotonatable group), and neutral at a second pH, preferably at physiological pH. It will of course be understood that the addition or removal of protons as a function of pH is an equilibrium process, and that the reference to a charged or a neutral lipid refers to the nature of the predominant species and does not require that all of the lipid be present in the charged or neutral form. Lipids which have more than one protonatable or deprotonatable group, or which are zwitterrionic are not excluded from use in the invention. Protonatable lipids are particularly useful as the first lipid component of the invention when the pKa of the protonatable group is in the range of about 4 to about 11. Most preferred is pKa of about 4 to about 7, because these lipids will be cationic at the lower pH formulation stage, while particles will be largely (though not completely) surface neutralized at physiological pH around pH 7.5. One of the benefits of this pKa is that at least some antisense stuck to the outside surface of the particle will lose its electrostatic interaction at physiological pH and be removed by simple dialysis; thus greatly reducing the particle's susceptibility to clearance.

Preferred lipids with a protonatable group for use as the first lipid component of the lipid mixture are amino lipids. As used herein, the term "amino lipid" is meant to include those lipids having one or two fatty acid or fatty alkyl chains and an amino head group (including an alkylamino or dialkylamino group) which is protonated to form a cationic lipid at physiological pH (see FIG. 2A). In one group of embodiments, the amino lipid is a primary, secondary or tertiary amine represented by the formula:

in which $R^1$ is a $C_{12}$ to $C_{24}$ alkyl group which is branched or unbranched, and saturated or unsaturated. $R^2$ is hydrogen or a $C_1$ to $C_{24}$ alkyl group which is also branched or unbranched, and saturated or unsaturated (when three or more carbons are present). $R^3$ is hydrogen or a $C_1$ to $C_6$ alkyl group. Examples of these amino lipids include, for example, stearylamine, oleylamine, dioleylamine, N-methyl-N,N-dioleylamine, and N,N-dimethyloleylamine.

In another group of embodiments, the amino lipid is a lipid in which the amino head group is attached to one or more fatty acid or fatty alkyl groups by a scaffold such as, for example, a glycerol or propanediol moiety. Illustrative of these amine lipids is the formula:

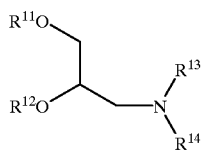

wherein at least one and preferably both of $R^{11}$ and $R^{12}$ is a $C_{12}$ to $C_{24}$ alkyl or acyl group which is branched or unbranched, saturated or unsaturated. In those embodiments in which only one of $R^{11}$ or $R^{12}$ is a long chain alkyl or acyl group, the other of $R^{11}$ or $R^{12}$ will be a hydrogen or lower alkyl or acyl group having from one to six carbon atoms. The remaining groups, $R^{13}$ and $R^{14}$ are typically hydrogen or $C_1$ to $C_4$ alkyl. In this group of embodiments, the amino lipid can be viewed as a derivative of 3-monoalkyl or dialkylamino-1,2-propanediol. An example of a suitable amino lipid is DODAP (1,2-dioleoyloxy-3-dimethylaminopropane, see FIG. 2A). Other amino lipids would include those having alternative fatty acid groups and other dialkylamino groups, including those in which the alkyl substituents are different (e.g., N-ethyl-N-methylamino-, N-propyl-N-ethylamino- and the like). For those embodiments in which $R^{11}$ and $R^{12}$ are both long chain alkyl or acyl groups, they can be the same or different. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ are particularly preferred. Other scaffolds can also be used to separate the amino group and the fatty acid or fatty alkyl portion of the amino lipid. Suitable scaffolds are known to those of skill in the art.

Compounds that are related to DODAP that may be useful with this invention include: 1-oleoyl-2-hydroxy-3-N,N-dimethylamino propane; 1,2-diacyl-3-N,N-dimethylamino propane; and 1,2-didecanoyl-1-N,N-dimethylamino propane. Further, it is proposed that various modifications of the DODAP or DODMA headgroup, or any compound of the general formula: can be modified to obtain a suitable pKa. Suitable headgroup modifications that are useful in the instant invention include:

|    | $R^1$ | $R^2$ |
|----|-------|-------|
| 1  | H | H |
| 2  | H | $CH_3$ |
| 3  | $CH_3$ | $CH_3$ |
| 4  | H | $CH_2CH_3$ |
| 5  | $CH_3$ | $CH_2CH_3$ |
| 6  | $CH_2CH_3$ | $CH_2CH_3$ |
| 7  | H | $CH_2CH_2OH$ |
| 8  | $CH_3$ | $CH_2CH_2OH$ |
| 9  | $CH_2CH_3$ | $CH_2CH_2OH$ |
| 10 | $CH_2CH_2OH$ | $CH_2CH_2OH$ |
| 11* | H | $CH_2CH_2NH_2$ |
| 12* | $CH_3$ | $CH_2CH_2NH_2$ |
| 13* | $CH_2CH_3$ | $CH_2CH_2NH_2$ |
| 14* | $CH_2CH_2OH$ | $CH_2CH_2NH_2$ |
| 15* | $CH_2CH_2NH_2$ | $CH_2CH_2NH_2$ |

In other embodiments, the amino lipid can be a derivative of a naturally occurring amino lipid, for example, sphingosine. Suitable derivatives of sphingosine would include those having additional fatty acid chains attached to either of the pendent hydroxyl groups, as well as alkyl groups, preferably lower alkyl groups, attached to the amino functional group.

Other lipids which may be used as the first lipid component of the invention include phosphine lipids (although toxicity issues may limit their utility), and carboxylic acid lipid derivative. These generally have a pKa of about 5 and are therefore useful with cationic therapeutic agents.

The second lipid component is selected to improve the formulation process by reducing aggregation of the lipid particles during formation. This may result from steric stabilization of particles which prevents charge-induced aggregation during formation. Examples of suitable lipids for this purpose include polyethylene glycol (PEG)-modified lipids, monosialoganglioside Gm1, and polyamide oligomers ("PAO") such as ATTA (disclosed in U.S. patent application Ser. No. 60/073,852 assigned to the assignee of the instant invention and incorporated herein by reference). Other compounds with uncharged, hydrophilic, steric-barrier moieties, that prevent aggregation during formulation, like PEG, Gm1 or ATTA, can also be coupled to lipids for use as the second lipid component in the methods and compositions of the invention. Typically, the concentration of the second lipid component is about 1 to 15% (by mole percent of lipids).

Specific examples of PEG-modified lipids (or lipid-polyoxyethylene conjugates) that are useful in the present invention can have a variety of "anchoring" lipid portions to secure the PEG portion to the surface of the lipid vesicle. Examples of suitable PEG-modified lipids include PEG-modified phosphatidylethanolamine and phosphatidic acid (see FIG. 2B, structures A and B), PEG-modified diacylglycerols and dialkylglycerols (see FIG. 2B, structures C and D), PEG-modified dialkylamines (FIG. 2B, structure E) and PEG-modified 1,2-diacyloxypropan-3-amines (FIG. 2B, structure F). Particularly preferred are PEG-ceramide conjugates (e.g., PEG-CerC14 or PEG-CerC20) which are described in co-pending U.S. Ser. No. 08/486,214, incorporated herein by reference.

In embodiments where a sterically-large moiety such as PEG or ATTA are conjugated to a lipid anchor, the selection of the lipid anchor depends on what type of association the conjugate is to have with the lipid particle. It is well known that mePEG(mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a $T_{1/2}$ less than 60 mins. in some assays. As illustrated in U.S. patent application Ser. No. 08/486,214 at least three characteristics influence the rate of exchange: length of acyl chain, saturation of acyl chain, and size of the steric-barrier head group. Compounds having suitable variations of these features may be useful for the invention.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a patient.

In addition to the first and second lipid components, the lipid mixture may contain additional lipid species. These additional lipids may be, for example, neutral lipids or sterols.

Neutral lipids, when present in the lipid mixture, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, cephalin, and cerebrosides. The selection of neutral lipids for use in the complexes herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the present invention are DOPE, DSPC, POPC, or any related phosphatidylcholine. The neutral lipids useful in the present invention may also be composed of sphingomyelin or phospholipids with other head groups, such as serine and inositol.

The sterol component of the lipid mixture, when present, can be any of those sterols conventionally used in the field of liposome, lipid vesicle or lipid particle preparation. A preferred sterol is cholesterol.

The mixture of lipids is typically a solution of lipids in an alcoholic solvent. Hydrophilic, low molecular weight water miscible alcohols with less than 10 carbon atoms, preferably less than 6 carbon atoms are preferred. Typical alcohols used in this invention are ethanol, methanol, propanol, butanol, pentanol and ethylene glycol and propylene glycol. Particularly preferred is ethanol. In most embodiments, the alcohol is used in the form in which it is commercially available. For example, ethanol can be used as absolute ethanol (100%), or as 95% ethanol, the remainder being water.

In one exemplary embodiment, the mixture of lipids is a mixture of amino lipids, neutral lipids (other than an amino lipid), a sterol (e.g., cholesterol) and a PEG-modified lipid (e.g., a PEG-ceramide) in an alcohol solvent. In preferred embodiments, the lipid mixture consists essentially of an amino lipid, a neutral lipid, cholesterol and a PEG-ceramide in alcohol, more preferably ethanol. In further preferred embodiments, the first solution consists of the above lipid mixture in molar ratios of about 10–35% amino lipid:25–45% neutral lipid:35–55% cholesterol:0.5–15% PEG-ceramnide. In still further preferred embodiments, the first solution consists essentially of DODAP, DSPC, Chol and PEG-CerC14, more preferably in a molar ratio of about 10–35% DODAP:25–45% DSPC:35–55% Chol:0.5–15% PEG-CerC14. In another group of preferred embodiments, the neutral lipid in these compositions is replaced with POPC or SM.

In accordance with the invention, the lipid mixture is combined with a buffered aqueous solution of charged therapeutic agent, preferably nucleic acids. The buffered aqueous solution of therapeutic agents (nucleic acids) which is combined with the lipid mixture is typically a solution in which the buffer has a pH of less than the $pK_a$ of the protonatable lipid in the lipid mixture. As used herein, the term "nucleic acid" is meant to include any oligonucleotide or polynucleotide having from 10 to 100,000 nucleotide residues. Antisense and ribozyme oligonucleotides are particularly preferred. The term "antisense oligonucleotide" or simply "antisense" is meant to include oligonucleotides which are complementary to a targeted nucleic acid and which contain from about 10 to about 50 nucleotides, more preferably about 15 to about 30 nucleotides. The term also encompasses antisense sequences which may not be exactly complementary to the desired target gene. Thus, the invention can be utilized in instances where non-target specific-activities are found with antisense, or where an antisense sequence containing one or more mismatches with the target sequence is the most preferred for a particular use.

The nucleic acid that is used in a lipid-nucleic acid particle according to this invention includes any form of nucleic acid that is known. Thus, the nucleic acid may be a modified nucleic acid of the type used previously to enhance nuclease resistance and serum stability. Surprisingly, however, acceptable therapeutic products can also be prepared using the method of the invention to formulate lipid-nucleic acid particles from nucleic acids which have no modification to the phosphodiester linkages of natural nucleic acid polymers, and the use of unmodified phosphodiester nucleic acids (i.e., nucleic acids in which all of the linkages are phosphodiester linkages) is a preferred embodiment of the invention. Still other nucleic acids which are useful in the present invention include, synthetic or pre-formed poly-RNA such as poly(IC) IC.

The nucleic acids used herein can be single-stranded DNA or RNA, or double-stranded DNA or DNA-RNA hybrids. Examples of double-stranded DNA include structural genes, genes including control and termination regions, and self-replicating systems such as plasmid DNA. Single-stranded nucleic acids include antisense oligonucleotides (discussed above and complementary to DNA and RNA), ribozymes and triplex-forming oligonucleotides.

In order to increase stability, some single-stranded nucleic acids may have some or all of the nucleotide linkages substituted with stable, non-phosphodiester linkages, including, for example, phosphorothioate, phosphorodithioate, phosphoroselenate, boranophosphate, methylphosphonate, or O-alkyl phosphotriester linkages. Phosphorothioate nucleic acids (PS-oligos) are those oligonucleotides or polynucleotides in which one of the non-bridged oxygens of the internucleotide linkage has been replaced with sulfur. These PS-oligos are resistant to nuclease degradation, yet retain sequence-specific activity. Similarly, phosphorodithioate nucleic acids are those oligonucleotides or polynucleotides in which each of the non-bridged oxygens of the internucleotide linkage have been replaced by a sulfur atom. These phosphorodithioate-oligos have also proven to be more nuclease resistant than the natural phosphodiester-linked form. Other useful nucleic acids derivatives include those nucleic acids molecules in which the bridging oxygen atoms (those forming the phosphoester linkages) have been replaced with —S—, —NH—, —CH$_2$— and the like. Preferably, the alterations to the antisense or other nucleic acids used will not completely affect the negative charges associated with the nucleic acids. Thus, the present invention contemplates the use of antisense and other nucleic acids in which a portion of the linkages are replaced with, for example, the neutral methyl any chemistry, will also be efficacious. Encapsulated particles may also have a broader range of in vivo utilities, showing efficacy in conditions and models not known to be otherwise responsive to antisense therapy. Those skilled in the art know that applying this invention they may find old models which now respond to antisense therapy. Further, they may revisit discarded antisense sequences or chemistries and find efficacy by employing the invention.

Therapeutic antisense sequences (putatively target specific) known to work with this invention include the following:

| Trivial Name: | Gene Target, Chemistry and Sequence | |
|---|---|---|
| PS-3082 | murine ICAM-1 (Intracellular Adhesion Molecule-1) (phosphorothioate) | |
| | TGCATCCCCCAGGCCACCAT | (SEQ ID. No 1) |
| PO-3082 | murine ICAM-1 (phosphodiester) | |
| | TGCATCCCCCAGGCCACCAT | (SEQ ID. No 1) |
| PS-2302 | human ICAM-1 (phosphorothiote) | |
| | GCCCAAGCTGGCATCCGTCA | (SEQ ID. No 2) |
| PO-2302 | human ICAM-1 (phosphodiester) | |
| | GCCCAAGCTGGCATCCGTCA | (SEQ ID. No 2) |
| PS-8997 | human ICAM-1 (phosphorothioate) | |
| | GCCCAAGCTGGCATCCGTCA | (SEQ ID. No 2) |
| US3 | human erb-B-2 gene (phosphodiester or phosphorothioate) | |
| | GGT GCT CAC TGC GGC | (SEQ ID. No 3) |
| LR-3280 | human c-myc gene (phosphorothioate) | |
| | AACC GTT GAG GGG CAT | (SEQ ID. No 4) |
| Inx-6298 | human c-myc gene (phosphodiester) | |
| | AAC GTT GAG GGG CAT | (SEQ ID. No 4) |
| Inx-6295 | human c-myc gene (phosphodiester or phosphorothioate) | |
| | T AAC GTT GAG GGG CAT | (SEQ ID. No 5) |
| LR-3001 | human c-myb gene (phosphodiester or phosphorothioate) | |
| | TAT GCT GTG CCG GGG TCT TCG GGC | (SEQ ID. No 6) |
| c-myb | human c-myb gene (phosphodiester or phosphorothioate) | |
| | GTG CCG GGG TCT TCG GGC | (SEQ ID. No 7) |
| IGF-1R | human IGF-1R (Insulin Growth Factor 1 - Receptor (phosphodiester or phosphorothioate) | |
| | GGA CCC TCC TCC GGA GCC | (SEQ ID. No 8) |
| LR-42 | human IGF-1R (phosphodiester or phosphorothioate) | |
| | TCC TCC GGA GCC AGA CTT | (SEQ ID. No 9) |
| EGFR | human EGFR (Epidermal Growth Factor Receptor) (phosphodiester or phosphorothioate) | |
| | CCG TGG TCA TGC TCC | (SEQ ID. No 10) |
| VEGF | human VEGF (Vascular Endothelial Growth Factor) gene (phosphodiester or phosphorothioate) | |
| | CAG CCT GGC TCA CCG CCT TGG | (SEQ ID. No 11) |
| PS-4189 | murine PKC-alpha (Phosphokinase C - alpha) gene (phosphodiester or phosphorothioate) | |
| | CAG CCA TGG TTC CCC CCA AC | (SEQ ID. No 12) |
| PS-3521 | human PKC-alpha (phosphodiester or phosphorothioate) | |
| | GTT CTC GCT GGT GAG TTT CA | (SEQ ID. No 13) |
| Bcl-2 | human bcl-2 gene (phosphodiester or phosphorothioate) | |
| | TCT CCC AgC gTg CgC CAT | (SEQ ID. No 14) |
| ATG-AS | human c-*raf*-1 protein kinase (phosphodiester or phosphorothioate) | |
| | GTG CTC CAT TGA TGC | (SEQ ID. No 15) |
| VEGF-R1 | human VEGF-1 (Vascular Endothelial Growth Factor Receptor 1) ribozyme | |
| | GAG UU CUG AUG AGG CCG AAA GGC CGA AAG UCU G | (SEQ ID. No 16) | phosphonate or phosphoramidate linkages. When neutral linkages are used, preferably less than 80% of the nucleic acid linkages are so substituted, more preferably less than 50%.

Those skilled in the art will realize that for in vivo utility, such as therapeutic efficacy, a reasonable rule of thumb is that if a thioated version of the sequence works in the free form, that encapsulated particles of the same sequence, of Using these sequences, the invention provides a method for the treatment of a diseases, including tumors, characterized by aberrant expression of a gene in a mammalian subject. The method comprises the steps of preparing a lipid-encapsulated therapeutic nucleic acid particle according to the methods as described herein, where the therapeutic nucleic acid component hybridizes specifically with the aberrantly expressed gene; and administering a therapeutically effective amount of the resulting particle to the mammalian subject. These sequences are, of course, only representative of the possible therapeutic oligonucleotide compounds that can be delivered using the invention. It is well known that, depending on the target gene, antisense that hybridizes to any part of the target gene, such as coding regions, introns, the 5' untranslated region (5'UTR), start of translation, or 3'UTR may have therapeutic utility. Therefore, the sequences listed above are only exemplary of antisense. Furthermore, all the alternative chemistries that have been proposed (i.e. see Background) can be tested with the invention to determine efficacy along with all types of ribozymes. In short, the compounds listed above represent the broad class of therapeutic 5–50 mer oligonucleotides of various chemistries which are useful with this invention. Other oligonucleotides which are useful include all those which have previously demonstrated efficacy in the free form.

While the invention is generally described and exemplified with regard to antisense oligonucleotides, other nucleic acids can be formulated and administered to a subject for the purpose of repairing or enhancing the expression of a cellular protein. Accordingly, the nucleic acid can be an expression vector, cloning vector or the like which is often a plasmid designed to be able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in $E.$ $coli$ for cloning and construction, and in a mammalian cell for expression.

Additionally, the nucleic acid can carry a label (e.g., radioactive label, fluorescent label or colorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, mRNA or oligonucleotides containing nucleic acid analogs, for example, the antisense derivatives described in a review by Stein, et al., $Science$ 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art. As with the modifications to the phosphodiester linkages discussed above, any modifications to the sugar or the base moieties should also act to preserve at least a portion of the negative charge normally associated with the nucleic acid. In particular, modifications will preferably result in retention of at least 10% of the overall negative charge, more preferably over 50% of the negative charge and still more preferably over 80% of the negative charge associated with the nucleic acid.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., $Tetrahedron$ $Lett.$, 22:1859–1862 (1981); Matteucci, et al., $J.$ $Am.$ $Chem.$ $Soc.$, 103:3185–3191 (1981); Caruthers, et al., $Genetic$ $Engineering$, 4:1–17 (1982); Jones, chapter 2, Atkinson, et al., chapter 3, and Sproat, et al., chapter 4, in $Oligonucleotide$ $Synthesis:$ $A$ $Practical$ $Approach,$ Gait (ed.), IRL Press, Washington D.C. (1984); Froehler, et al., $Tetrahedron$ $Lett.$, 27:469–472 (1986); Froehier, et al., $Nucleic$ $Acids$ $Res.$, 14:5399–5407 (1986); Sinha, et al. $Tetrahedron$ $Lett.$, 24:5843–5846 (1983); and Sinha, et al., $Nucl.$ $Acids$ $Res.$, 12:4539–4557 (1984) which are incorporated herein by reference.

As noted above, the solution of therapeutic agent (nucleic acids) comprises an aqueous buffer. Preferred buffers (in the case of anionic therapeutic agents) are those which provide a pH of less than the $pK_a$ of the first lipid component. Examples of suitable buffers include citrate, phosphate, acetate, and MES. A particularly preferred buffer is citrate buffer. Preferred buffers will be in the range of 1–1000 mM of the anion, depending on the chemistry of the oligonucleotide being encapsulated, and optimization of buffer concentration may be significant to achieving high loading levels (See. FIGS. 15 and 20). Alternatively, pure water acidified to pH 5–6 with chloride, sulfate or the like may be useful. In this case, it may be suitable to add 5% glucose, or another non-ionic solute which will balance the osmotic potential across the particle membrane when the particles are dialyzed to remove ethanol, increase the pH, or mixed with a pharmaceutically acceptable carrier such as normal saline. The amount of therapeutic agent (nucleic acid) in buffer can vary, but will typically be from about 0.01 mg/mL to about 200 mg/mL, more preferably from about 0.5 mg/mL to about 50 mg/mL.

The mixture of lipids and the buffered aqueous solution of therapeutic agent (nucleic acids) is combined to provide an intermediate mixture. The intermediate mixture is typically a mixture of lipid particles having encapsulated therapeutic agent (nucleic acids). Additionally, the intermediate mixture may also contain some portion of therapeutic agent (nucleic acids) which are attached to the surface of the lipid particles (liposomes or lipid vesicles) due to the ionic attraction of the negatively-charged nucleic acids and positively-charged lipids on the lipid particle surface (the amino lipids or other lipid making up the protonatable first lipid component are positively charged in a buffer having a pH of less than the $pK_a$ of the protonatable group on the lipid). In one group of preferred embodiments, the mixture of lipids is an alcohol solution of lipids and the volumes of each of the solutions is adjusted so that upon combination, the resulting alcohol content is from about 20% by volume to about 45% by volume. The method of combining the mixtures can include any of a variety of processes, often depending upon the scale of formulation produced. For example, when the total volume is about 10–20 mL or less, the solutions can be combined in a test tube and stirred together using a vortex mixer. Large-scale processes can be carried out in suitable production scale glassware.

Optionally, the lipid-encapsulated therapeutic agent (nucleic acid) complexes which are produced by combining the lipid mixture and the buffered aqueous solution of therapeutic agents (nucleic acids) can be sized to achieve a desired size range and relatively narrow distribution of lipid particle sizes. Preferably, the compositions provided herein will be sized to a mean diameter of from about 70 to about 200 nm, more preferably about 90 to about 130 nm. Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size determination. For the methods herein, extrusion is used to obtain a uniform vesicle size.

Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing.

The present invention further comprises a step of neutralizing at least some of the surface charges on the lipid portions of the lipid-nucleic acid compositions. By at least partially neutralizing the surface charges, unencapsulated antisense or other nucleic acid is freed from the lipid particle surface and can be removed from the composition using conventional techniques. Preferably, unencapsulated and surface adsorbed nucleic acids is removed from the resulting compositions through exchange of buffer solutions. For example, replacement of a citrate buffer (pH about 4.0, used for forming the compositions) with a HEPES-buffered saline (HBS pH about 7.5) solution, results in the neutralization of liposome surface and antisense release from the surface. The released antisense can then be removed via chromatography using standard methods, and then switched into a buffer with a pH above the pKa of the lipid used.

In other aspects, the present invention provides lipid-encapsulated nucleic acid compositions, preferably prepared by the methods recited above. Accordingly, preferred compositions are those having the lipid ratios and nucleic acid preferences noted above.

In still other aspects, the present invention contemplates reversed-charge methods in which the lipid portion of the complex contains certain anionic lipids and the component which is encapsulated is a positively charged therapeutic agent. One example of a positively charged agent is a positively charged peptide or protein. In essentially an identical manner, liposome-encapsulated protein is formed at a pH above the pKa of the anionic lipid, then the surface is neutralized by exchanging the buffer with a buffer of lower pH (which would also release surface-bound peptide or protein).

IV. Pharmaceutical Preparations

The lipid-nucleic acid compositions prepared by the above methods can be administered either alone or in mixture with a physiologically-acceptable carrier (such as physiological saline or phosphate buffer) selected in accordance with the route of administration and standard pharmaceutical practice.

Pharmaceutical compositions comprising the lipid-nucleic acid compositions of the invention are prepared according to standard techniques and further comprise a pharmaceutically acceptable carrier. Generally, normal saline will be employed as the pharmaceutically acceptable carrier. Other suitable carriers include, e.g., water, buffered water, 0.9% saline, 0.3% glycine, and the like, including glycoproteins for enhanced stability, such as albumin, lipoprotein, globulin, etc. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline. The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid-nucleic acid complexes in the pharmaceutical formulations can vary widely, i.e., from less than about 0.01%, usually at or at least about 0.05–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, the lipid-therapeutic agent (nucleic acid) compositions of the invention include polyethylene glycol (PEG)-modified phospholipids, PEG-ceramide, or ganglioside $G_{M1}$-modified lipids or other lipids effective to prevent or limit aggregation. Addition of such components does not merely prevent complex aggregation, however, it may also provides a means for increasing circulation lifetime and increasing the delivery of the lipid-nucleic acid composition to the target tissues.

The present invention also provides lipid-nucleic acid compositions in kit form. The kit will typically be comprised of a container which is compartmentalized for holding the various elements of the kit. The kit will contain the compositions of the present inventions, preferably in dehydrated or concentrated form, with instructions for their rehydration or dilution and administration. In still other embodiments, the lipid-encapsulated-therapeutic agent (nucleic acid) particles will have a targeting moiety attached to the surface of the lipid particle. Methods of attaching targeting moieties (e.g., antibodies, proteins, small molecule mimetics, vitamins, oligosaccharides and hyaluronic acid) to lipids (such as those used in the present compositions) are known to those of skill in the art.

Dosage for the lipid-nucleic acid compositions will depend on the ratio of nucleic acid to lipid and the administrating physician's opinion based on age, weight, and condition of the patient.

V. Methods of Introducing Lipid-Encapsulated Therapeutic Agents into Cells

The lipid-therapeutic agent compositions of the invention can be used for introduction of those therapeutic agents into cells. In the case of nucleic acid-containing compositions, the composition of the invention are useful for the introduction of nucleic acids, preferably plasmids, antisense and ribozymes into cells. Accordingly, the present invention also provides methods for introducing a therapeutic agent such as a nucleic acid into a cell. The methods are carried out in vitro or in vivo by first forming the compositions as described above, then contacting the compositions with the target cells for a period of time sufficient for transfection to occur.

The compositions of the present invention can be adsorbed to almost any cell type. Once adsorbed, the complexes can either be endocytosed by a portion of the cells, exchange lipids with cell membranes, or fuse with the cells. Transfer or incorporation of the nucleic acid portion of the complex can take place via any one of these pathways. In particular, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between about 1 $\mu$mol and about 10 mmol. Treatment of the cells with the lipid-nucleic acid compositions will generally be carried out at physiological temperatures (about 37° C.) for periods of time of from about 1 to 6 hours, preferably of from about 2 to 4 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of preferred embodiments, a lipid-nucleic acid particle suspension is added to 60–80% confluent plated cells having a cell density of from about $10^3$ to about $10^5$ cells/mL, more preferably about $2 \times 10^4$ cells/mL. The concentration of the suspension added to the cells is preferably of from about 0.01 to 0.2 $\mu$g/mL, more preferably about 0.1 $\mu$g/mL.

Typical applications include using well known transfection procedures to provide intracellular delivery of DNA or MRNA sequences which code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630–643 (1989), and for cystic fibrosis, see Goodfellow, *Nature* 341:102–103 (1989)). Other uses for the compositions of the present invention include introduction of antisense oligonucleotides in cells (see, Bennett, et al., *Mol. Pharm.* 41:1023–1033 (1992)).

Alternatively, the compositions of the present invention can also be used for the transfection of cells in vivo, using methods which are known to those of skill in the art. In particular, Zhu, et al., *Science* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278–281 (1989), incorporated herein by reference, describes the in vivo transfection of lungs of mice with a functioning prokaryotic gene encoding the intracellular enzyme, chloramphenicol acetyltransferase (CAT). Thus, the compositions of the invention can be used in the treatment of infectious diseases.

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512–527 (1983); Mannino, et al., *Biotechniques* 6:682–690 (1988); Nicolau, et al., *Crit. Rev. Ther. Drug Carrier Syst.* 6:239–271 (1989), and Behr, *Acc. Chem. Res.* 26:274–278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs (see, Brigham, et al., *Am. J. Sci.* 298(4):278–281 (1989)) or by direct injection at the site of disease (Culver, HUMAN GENE THERAPY, MaryAnn Liebert, Inc., Publishers, New York. pp.70–71 (1994)).

The methods of the present invention may be practiced in a variety of hosts. Preferred hosts include mammalian species, such as humans, non-human primates, dogs, cats, cattle, horses, sheep, and the like.

VI. Examples
Materials and Methods
Lipids

Distearoylphosphatidylcholine (DSPC), sphingomyelin (SM), and palmitoyloleoylphosphatidylcholine (POPC) were purchased from Northern Lipids (Vancouver, Canada). 1,2-dioleoyloxy-3-dimethylammoniumpropane (DODAP or AL-1) was synthesized by Dr. Steven Ansell (Inex Pharmaceuticals) or, alternatively, was purchased from Avanti Polar Lipids. Cholesterol was purchased from Sigma Chemical Company (St. Louis, Mo., USA). PEG-ceramides were synthesized by Dr. Zhao Wang at Inex Pharmaceuticals, Corp. using procedures described in PCT WO 96/40964, incorporated herein by reference. [$^3$H] or [$^{14}$C]-CHE was purchased from NEN (Boston, Mass., USA). All lipids were >99% pure.

Buffers and Solvents

Ethanol (95%), methanol, chloroform, citric acid, HEPES and NaCl were all purchased from commercial suppliers.

Synthesis and Purification of Phosphorothioate Antisense

PS 3082, a 20 mer phosphorothioate antisense oligodeoxynucleotide, was synthesized, purified and donated by ISIS Pharmaceuticals (Carlsbad, Calif., USA). The sequence for this oligo is: TGCATCCCCCAGGCCAC-CAT. (Seq ID No 1). The details of the synthesis and purification can be found elsewhere (see, Stepkowski, et al., J. Immunol. 153:5336–5346 (1994)).

Preparation of Liposomal Antisense

Lipid stock solutions were prepared in 95% ethanol at 20 mg/mL (PEG-Ceramides were prepared at 50 mg/mL). DSPC, CHOL, DODAP, PEG-CerC14 (25:45:20:10, molar ratio), 13 μmol total lipid, were added to a 13×100 mm test tube containing trace amounts of [$^{14}$C]-cholesterylhexadecylether. The final volume of the lipid mixture was 0.4 mL. In some experiments, SM or POPC was substituted for DSPC. A 20 mer antisense oligodeoxynucleotide, PS 3082 (2 mg), and trace amounts of [$^3$H]-PS 3082 were dissolved in 0.6 mL of 300 mM citric acid, pH 3.8 in a separate 13×100 mm test tube. The antisense solution was warmed to 65° C. and the lipids (in ethanol) were slowly added, mixing constantly. The resulting volume of the mixture was 1.0 mL and contained 13 μmol total lipid, 2 mg of antisense oligodeoxynucleotide, and 38% ethanol, vol/vol. The antisense-lipid mixture was subjected to 5 cycles of freezing (liquid nitrogen) and thawing (65 ° C.), and subsequently was passed 10X through three stacked 100 nm filters (Poretics) using a pressurized extruder apparatus with a thermobarrel attachment (Lipex Biomembranes). The temperature and pressure during extrusion were 65 ° C. and 300–400 psi (nitrogen), respectively. The extruded preparation was diluted with 1.0 mL of 300 mM citric acid, pH 3.8, reducing the ethanol content to 20%. The preparation was immediately applied to a gel filtration column. Alternatively, the extruded sample was dialyzed (12 000–14 000 MW cutoff; SpectraPor) against several liters of 300 mM citrate buffer, pH 3.8 for 3–4 hours to remove the excess ethanol. The sample was subsequently dialyzed against HBS, pH 7.5, for 12–18 hours to neutralize the DODAP and release any antisense that was associated with the surface of the vesicles. The free antisense was removed from the encapsulated liposomal antisense by gel exclusion chromatography as described below.

Gel Filtration Chromatography

A 20×2.5 cm glass column containing Biogel A15m, 100–200 mesh, was equilibrated in HEPES-buffered saline (HBS; 20 mM HEPES, 145 mM NaCl, pH 7.5). The 2.0 mL liposomal antisense preparation was applied to the column and allowed to drain into the gel bed under gravity. The column was eluted with HBS at a flow rate of 50 mL/hr. Column fractions (1.0 mL) were collected and analyzed for radioactivity using standard liquid scintillation counting techniques. The fractions were pooled based on the levels of [$^{14}$C]-CHE present in the fraction. The size distribution of the pooled liposomal antisense was determined using a NICOMP Model 370 Sub-micron particle sizer and was typically 110±30 nm.

Ion Exchange Chromatography

As an alternative to gel filtration chromatography, samples were sometimes dialyzed first in 300 mM citrate, pH 3.80, for 2–3 hours to remove residual ethanol, followed by at least a 12 hour dialysis in HBS, to exchange the external citrate for HBS and remove residual ethanol. The sample was applied to a 1.5×8 cm DEAE-Sepharose® column equilibrated in HBS. Free oligonucleotide binds to the DEAE with very high affinity. The peak containing the lipid was pooled, concentrated, and analyzed for antisense content, as described below.

Assessment of Antisense Encapsulation

Antisense encapsulation was typically assessed by dual label ([$^3$H]-antisense and [$^{14}$C]-lipid) liquid scintillation counting after gel filtration chromatography to separate the free and encapsulated antisense. Antisense encapsulation was evaluated by summing the total [$^3$H]-antisense radioactivity associated with the lipid peak and dividing by the total [$^3$H]-antisense radioactivity. Alternatively, the [$^3$H]/[$^{14}$C] ratio was determined before and after (i.e., in the pooled lipid peak) gel filtration chromatography. Antisense encapsulation was also assessed by measuring the absorbance of the sample at 260 nm, preceded by a Bligh and Dyer extraction of the antisense from the lipid, as described below.

Extraction of the Antisense

The antisense was extracted from the lipid according to the procedure outlined by Bligh and Dyer (Bligh, et al., Can. J. Biochem. Physiol. 37:911–917 (1959)). Briefly, up to 250 μL of aqueous sample was added to a 13×100 mm glass test tube, followed by the addition of 750 μL of chloroform-:methanol (1:2.1, vol/vol), 250 μL of chloroform, and 250 μL of distilled water. The sample was mixed after each addition. The sample was centrifuged for 10 min. at 3000 rpm, resulting in a clear two-phase separation. The aqueous phase (top) was removed into a new 13×100 mm test tube. An aliquot (500 μL) of this phase was diluted with 500 μL of distilled water, mixed, and the absorbance at 260 nm was assessed using a spectrophotometer. In some instances, the organic phase (bottom) was washed with 250 μL of methanol, centrifuged for 10 min. at 3000 rpm, and the upper phase removed and discarded. This was repeated 3 times. The washed organic phase was assessed for phospholipid content according to the method of Fiske and Subbarrow (Fiske, et al., J. Biol. Chem. 66:375–400 (1925)).

Oligreen Assay

A fluorescent dye binding assay for quantifying single stranded oligonucleotide in aqueous solutions was established using a Biolumin™ 960 fluorescent plate reader (Molecular Dynamics, Sunnyvale, Calif., USA). Briefly, aliquots of encapsulated oligonucleotide were diluted in HEPES buffered saline (HBS; 20 mM HEPES, 145 mM NaCl, pH 7.5). A 10 μL aliquot of the diluted sample was added to 100 μL of a 1:200 dilution of Oligreen™ reagent, both with and without 0.1% of Triton X-100 detergent. An oligo standard curve was prepared with and without 0.1% Triton X-100 for quantification of encapsulated oligo. Fluorescence of the OLIGREEN™-antisense complex was measured using excitation and emission wavelengths of 485 nm and 520 nm, respectively. Surface associated antisense was determined by comparing the fluorescence measurements in the absence and presence of detergent.

Ear Inflammation Model and Efficacy Studies

Sensitization and Elicitation of Contact Sensitivity

Mice were sensitized by applying 25 μL of 0.5% 2,4-dinitro-1-fluorobenzene (DNFB) in acetone:olive oil (4:1) to the shaved abdominal wall for two consecutive days. Four days after the second application, mice were challenged on the dorsal surface of the left ear with 10 μL of 0.2% DNFB in acetone:olive oil (4:1). Mice received no treatment on the contralateral (right) ear. In some cases, control mice received 10 μL of vehicle on the dorsal surface of the left ear.

Evaluation of Ear Swelling

Ear thickness was measured immediately prior to ear challenge, and at various time intervals after DNFB challenge, using an engineer's micrometer (Mitutoyo, Tokyo, Japan). Increases in ear thickness measurements were determined by subtracting the pre-challenge from post-challenge measurements.

The progression of ear inflammation over a 3 day period for ICR (outbred) mice is indicated in FIGS. 12 and 13. Erythema was evident almost immediately after ear challenge and gradually declined in intensity over the remainder of the study. ICR mice exhibited peak ear thickness at 24 hours after the induction of ear inflammation. Maximal ear thickness measurements were found to be $170 \times 10^{-4}$ inches, corresponding to a 70% increase in ear thickness. Although ear swelling gradually declines at 48 and 72 hours after inflammation initiation, ear measurements still have not returned to baseline thickness levels ($90-100 \times 10^{-4}$ inches).

The mouse in vivo experimental systems in this specification were selected in part because of their high degree of correlation to human disease conditions. The mouse ear inflammation model, which can be treated using methods and compositions of the invention, is well known to be an excellent model for human allergic contact dermatitis and other disease conditions. The control therapeutic used in this model is a corticosteroid which demonstrates efficacy both in the mouse model and in related human disease conditions.

The mouse B16 tumor model, a fast growing melanoma, which can be treated using methods and compositions of the invention, is a standard, widely used experimental system. This tumor model can be successfully treated using vinca alkaloids, such as vincristine or vinblastine, which are known to be efficacious against human tumors as well.

Treatments which demonstrate utility in the mouse models of this invention are excellent candidates for testing against human disease conditions, at similar dosages and administration modalities.

EXAMPLE 1

This example illustrates the effects of ethanol on the encapsulation of antisense.

A 20 mer of [$^3$H]-phosphorothioate antisense oligodeoxynucleotide (in 300 mM citrate buffer, pH 3.80) was mixed with an ethanol solution of lipid (DSPC:CHOL:DODAP:PEG-CerC14; 25:45:20:10, molar ratio) at final concentrations of 2 mg/mL and 9.9 mg/mL, respectively. The final ethanol concentration in the preparations was varied between 0 and 60%, vol/vol. The samples were extruded ten times through three 100 nm filters as described in "Materials and Methods". The samples were dialyzed for 2–3 hours in 300 mM citrate buffer, pH 3.80, to remove a majority of the excess ethanol. The samples were switched to HEPES-buffered saline (HBS), pH 7.50, and dialyzed for a minimum of 12 hours to replace the external citrate buffer with HBS. This renders the majority of DODAP in the outer bilayer neutral, and will release any surface bound antisense. Non-encapsulated antisense was then removed from the liposomal antisense by DEAE-sepharose chromatography as described in "Material and Methods". Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity.

In another experiment, the formulations were prepared as described. After extrusion, the filters were analyzed for [$^3$H]-antisense and [$^{14}$C]-lipid radioactivity by standard scintillation counting techniques. Results were expressed as a percent of the total initial radioactivity.

Figure 3:
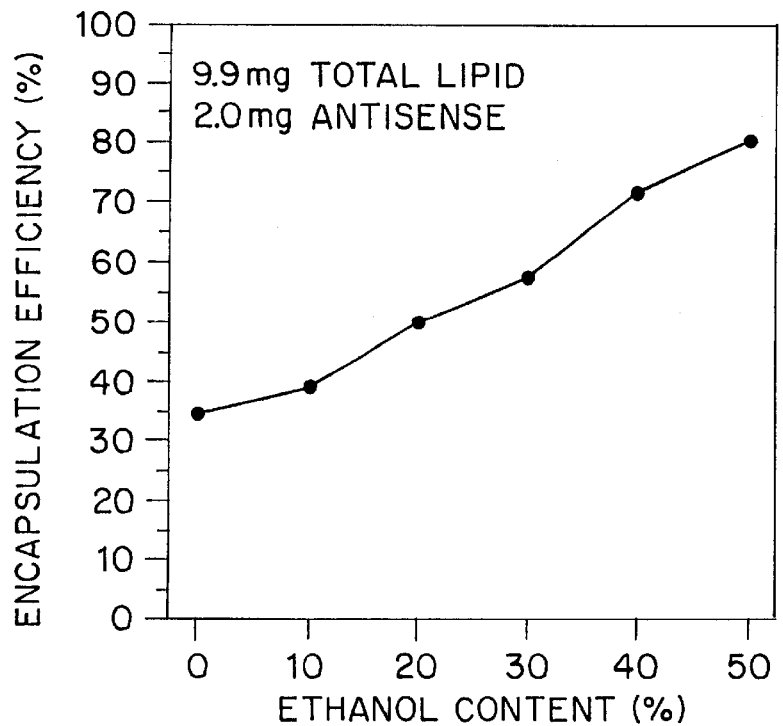
FIG. 3 illustrates the influence of ethanol on the encapsulation of antisense oligodeoxynucleotides. The liposomal antisense compositions were prepared as described in the Examples, with the final concentrations of antisense and lipids being 2 mg/mL and 9.9 mg/mL, respectively. The final ethanol concentration in the preparations was varied between 0 and 60%, vol/vol. Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity.
Figure 4:
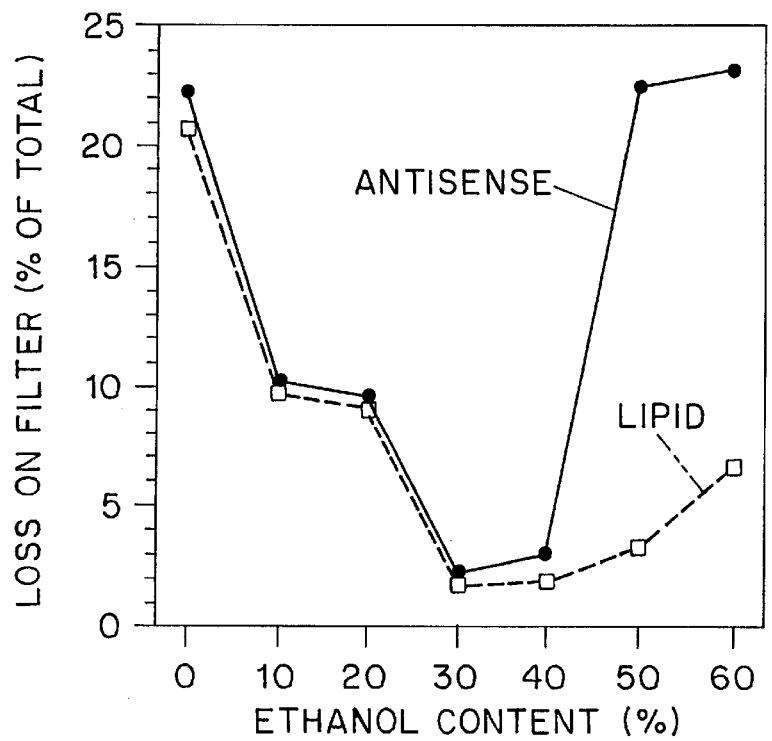
FIG. 4 illustrates the influence of ethanol on lipid and antisense loss during extrusion. The liposomal antisense compositions were prepared as described for FIG. 3. The samples were extruded ten times through three 100 nm filters as described in "Materials and Methods". After extrusion, the filters were analyzed for [$^3$H]-antisense and [$^{14}$C]-lipid radioactivity by standard scintillation counting techniques. Results were expressed as a percent of the total initial radioactivity.

FIG. 3 demonstrates the effects of ethanol on the encapsulation of antisense at pH 3.8. The encapsulation efficiency of phosphorothioate antisense increases in a near linear manner up to a final ethanol concentration of 50%, vol/vol. At an ethanol content greater than 50%, a large amount of aggregation/precipitation is observed. The effect of ethanol on vesicle formation can be further observed by monitoring both lipid and antisense loss on the filters during extrusion (FIG. 4). At low ethanol contents, extrusion is slow and the proportion of lipid and antisense loss is the same, suggesting that the losses are due to the formation of large complexes which get trapped on the filter. At ethanol contents of 30 and 40%, extrusion is very quick and losses of both lipid and antisense are minimal. As the ethanol content is increased above 40%, the loss of antisense becomes disproportionally high relative to the lipid. This can be attributed to the insolubility of DNA in high concentrations of alcohol. Furthermore, in the presence of ethanol, PEG is required to prevent aggregation and fusion of the vesicles (results not shown).

EXAMPLE 2

This example illustrates the effects of DODAP on the encapsulation of antisense, and further illustrates the effect of initial antisense concentration on the compositions.

Figure 5:
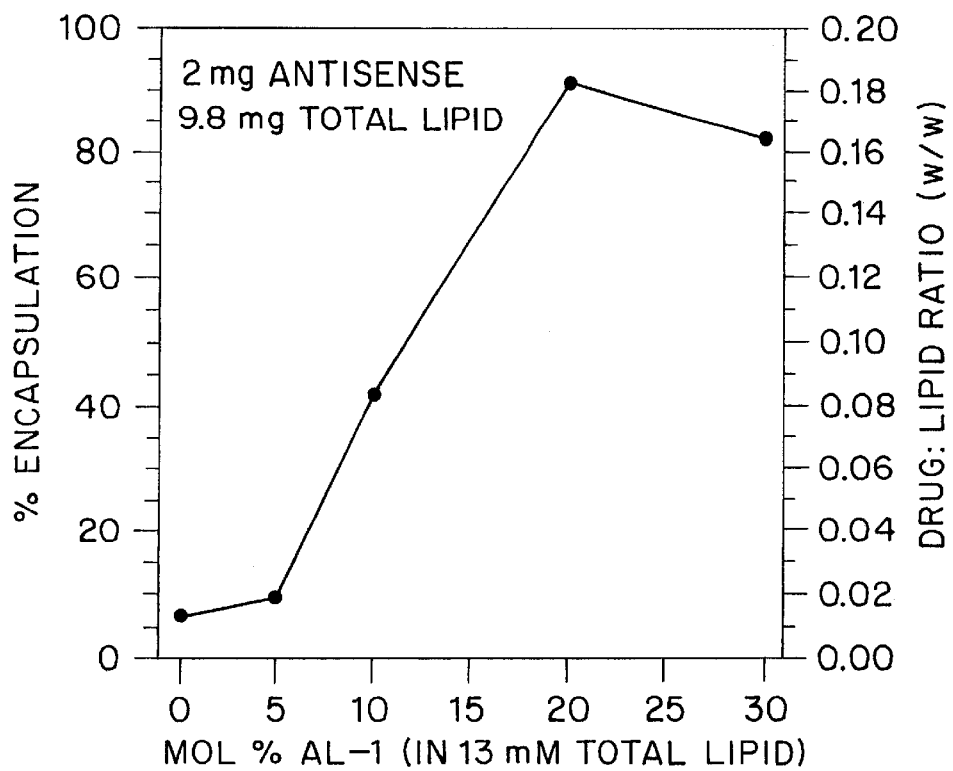
FIG. 5 illustrates the influence of DODAP content on the encapsulation of antisense oligodeoxynucleotides. A 0.6 mL aliquot of a [$^3$H]-phosphorothioate antisense oligodeoxynucleotide (in 300 mM citrate buffer, pH 3.80) was mixed with 0.4 mL of a 95% ethanol solution of lipid (DSPC:CHOL:DODAP:PEG-CerC14; 100-(55+X):45:X:10, molar ratio) at final concentrations of 2 mg/mL and 9.9 mg/mL, respectively. The molar ratio of DODAP was varied between 0 and 30%. The molar ratio of DSPC was adjusted to compensate for the changes in DODAP content. Encapsulation was assessed either by analyzing the pre-column and post-column ratios of [$^3$H]-antisense and [$^{14}$C]-lipid or by determining the total pre-colunn and post-column [$^3$H]-antisense and [$^{14}$C]-lipid radioactivity.
Figure 6:
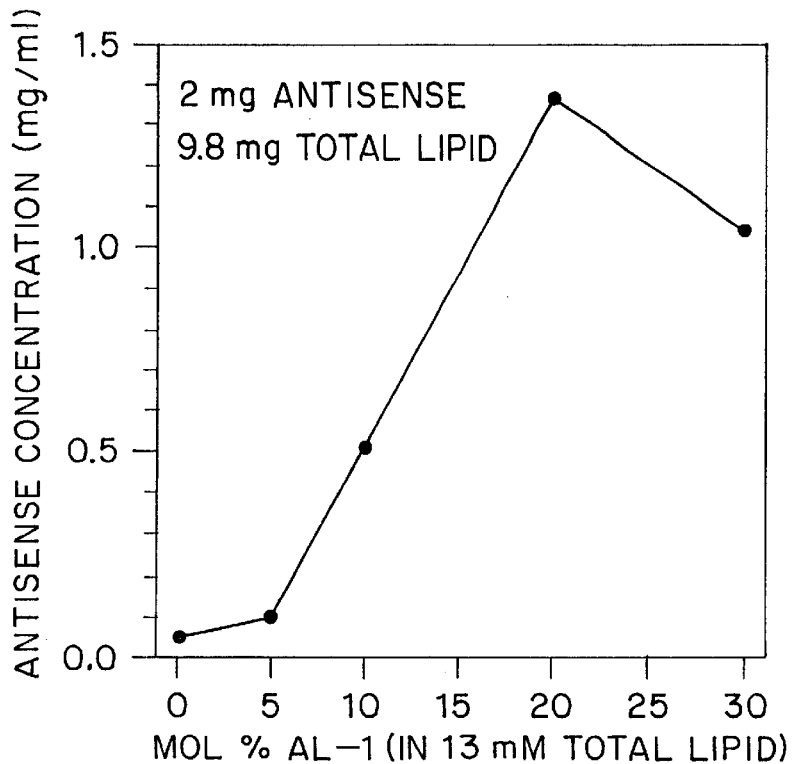
FIG. 6 illustrates the influence of DODAP content on the encapsulation of antisense oligodeoxynucleotides. Samples were identical to those prepared in FIG. 5. In this instance, the amount of antisense associated with the lipid was assessed by a solvent extraction procedure as described in "Material and Methods". Antisense was extracted into a methanol:water aqueous phase, while the lipid was soluble in the organic (chloroform) phase. The aqueous phase was preserved and antisense concentration was determined by measuring the absorbance at 260 nm. This confirmed that the antisense was associated with the lipid vesicles, and that the [$^3$H]-label on the antisense had not exchanged to the lipid.

Having demonstrated that ethanol can greatly facilitate the preparation of lipid vesicles containing entrapped antisense, the next step was to examine the influence of DODAP (AL-1) content on the encapsulation of antisense (FIG. 5). Accordingly, a 0.6 mL aliquot of a [$^3$H]-phosphorothioate antisense oligodeoxynucleotide (in 300 mM citrate buffer, pH 3.80) was mixed with 0.4 mL of a 95% ethanol solution of lipid (DSPC:CHOL:DODAP:PEG-CerC14; 100-(55+X):45:X:10, molar ratio) at final concentrations of 2 mg/mL and 9.9 mg/mL, respectively. The molar ratio of DODAP was varied between 0 and 30%. The molar ratio of DSPC was adjusted to compensate for the changes in DODAP content. The samples were extruded ten times through three 100 nm filters as described in "Materials and Methods", and were dialyzed for 2–3 hours in 300 mM citrate buffer, pH 3.80, to remove a majority of the excess ethanol. The samples were switched to HEPES-buffered saline (HBS), pH 7.50, and dialyzed for a minimum of 12 hours to replace the external citrate buffer with HBS. Non-encapsulated antisense was then removed from the liposomal antisense by DEAE-sepharose chromatography as described in "Material and Methods". Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity. As seen in FIG. 5, antisense encapsulation increased significantly between 5–20% DODAP. At DODAP contents greater than 20–25%, extrusion of the vesicles became more difficult suggesting the formation of complexes. At DODAP concentration of 40 and 50%, extrusion of the lipid/antisense mixture took hours compared to minutes for a lipid composition containing 20% DODAP. To verify that the antisense was indeed associated with the lipid and that the observed encapsulation was not due to exchange of the [$^3$H]-label from the antisense onto the lipid, the antisense was extracted from the lipid using a Bligh and Dyer extraction. Using this technique, the antisense, which is soluble in the aqueous phase, was separated from the lipid (soluble in the organic phase) and quantified by measuring the absorbance at 260 nm (FIG. 6). While this method can underestimate the antisense concentration, the technique substantiated that the observed association of antisense with the lipid was not an artifact.

In yet another experiment, varying concentrations of a 20 mer of [$^3$H]-phosphorothioate antisense oligodeoxynucleotide (in 300 mM citrate buffer, pH 3.80) were mixed with an ethanol solution of lipid (DSPC:CHOL:DODAP:PEG-CerC14; 25:45:20:10, molar ratio), 9.9 mg/mL (final concentration). The samples were extruded and dialyzed twice as described above. Non-encapsulated antisense was then removed from the liposomal antisense by DEAE-sepharose chromatography as described in "Material and Methods". Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity. EPC:CH liposomes containing encapsulated antisense are included for comparison.

Figure 8:
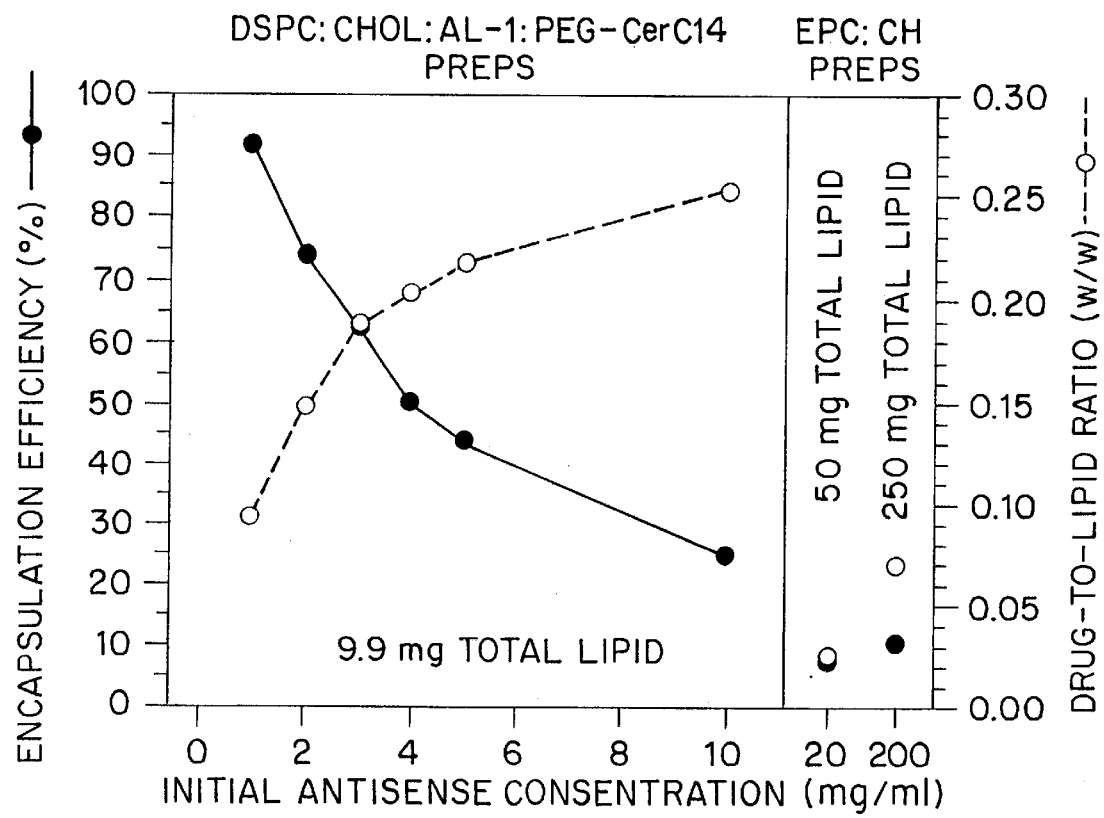
FIG. 8 illustrates the influence of the initial antisense concentration on antisense loading in DODAP vesicles. Varying final concentrations of a 20mer of [$^3$H]-phosphorothioate antisense oligodeoxynucleotide (in 300 mM citrate buffer, pH 3.80) were mixed with an ethanol solution of lipid (DSPC:CHOL:DODAP:PEG-CerC14; 25:45:20:10, molar ratio), 9.9 mg/mL (final concentration). Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity.

Optimization of the drug:lipid ratio was accomplished by increasing the initial antisense concentration that was mixed with 9.8 mg total lipid (DSPC:CHOL:DODAP:PEG-CerC14; 25:45:20:10) (FIG. 8). Drug:lipid ratios of up to 0.25, w/w, were obtained using 10 mg/mL of antisense in the preparation. However, the increased drug:lipid ratio was accompanied by a decrease in encapsulation efficiency, therefore a compromise must be made between optimizing the drug:lipid ratio and encapsulation efficiency. In comparison, antisense encapsulated by hydration of a dry lipid film (i.e. EPC:CHOL) in the absence of cationic lipid typically yields low encapsulation efficiencies (<12–15%) and drug:lipid ratios (<0.1, w/w). Consequently, significant quantities of antisense are wasted during the encapsulation procedure.

EXAMPLE 3

This example illustrates the properties of the liposomal antisense formulations provided in the Materials and Methods above.

The size distribution of a liposomal preparation of antisense was determined by quasi-elastic light scattering (QELS) immediately after removal of the free antisense (A), and after storage of the preparation for 2 months at 4° C. (B), using a Nicomp Model 370 sub-micron particle sizer. A 0.6 mL aliquot of a [$^3$H]-phosphorothioate antisense oligodeoxynucleotide (in 300 mM citrate buffer, pH 3.80) was mixed with 0.4 mL of a 95% ethanol solution of lipid (DSPC:CHOL:DODAP:PEG-CerC14; 25:45:20:10, molar ratio) at final concentrations of 2 mg/mL and 9.9 mg/mL, respectively. The sample was extruded ten times through three 100 nm filters as described in "Materials and Methods", and dialyzed for 2–3 hours in 300 mM citrate buffer, pH 3.80, to remove a majority of the excess ethanol. The sample was switched to HEPES-buffered saline (HBS), pH 7.50, and dialyzed for a minimum of 12 hours to replace the external citrate buffer with HBS. Non-encapsulated antisense was then removed from the liposomal antisense by DEAE-sepharose chromatography as described in "Material and Methods".

The size distribution and storage stability of antisense preparations described herein is demonstrated in FIG. 7. The size distribution of a standard DSPC:CHOL:DODAP:PEG-CerC14 (25:45:20:10) preparation containing a 2 mg/mL initial antisense concentration was analyzed immediately after column chromatography to remove any free antisense. A very homogenous distribution is observed after preparation (119±32 nm). This size distribution remained stable for at least 2 months after storage at 4° C. (119±32 nm).

EXAMPLE 4

This example illustrates the clearance pharmacokinetics, biodistribution and biological activity of an encapsulated murine ICAM-1 phosphorothioate antisense oligodeoxynucleotide.

4.1 Plasma Clearance

Encapsulated liposomal antisense was prepared using the ethanol-citrate procedure as described in "Material and Methods". Initial lipid and antisense concentrations were 9.9 and 2 mg/mL, respectively. Liposomal formulations were composed of X:CHOL:DODAP:PEG-CerC14 (25:45:20:10), where X represents either distearoylphosphatidylcholine (DSPC), sphingomyelin (SM), or palmitoyloleoylphosphatidylcholine (POPC). The formulations contained a lipid label ([$^{14}$C]-cholesterylhexadecylether) and [$^3$H]-antisense and were injected (200 µL) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques.

The plasma clearance of three formulations, DSPC:CHOL:DODAP:PEG-CerC14, SM:CHOL:DODAP:PEG-CerC14, and POPC:CHOL:DODAP:PEG-CerC14, of encapsulated antisense were examined in inflamed ICR mice (FIG. 9). The circulation time was longest for the DSPC version of the formulation.

4.2 Organ Accumulation

Liposomal antisense compositions were prepared and administered to mice as outlined in the preceding section. Mice were terminated by cervical dislocation and the organs were recovered and processed as described in "Materials and Methods". Lipid and antisense recoveries were determined by standard scintillation counting techniques.

Organ accumulation of the various formulations was typical of previously described liposome clearance patterns, with the RES organs, principally the liver and spleen, being responsible for the majority of clearance (FIG. 10). One interesting observation is that the liver and spleen clearance account for only 40–45% of the total clearance of the "DSPC" formulation, suggesting that a significant population of vesicles is accumulating in another organ system or is being excreted.

4.3 Stability

Liposomal antisense compositions were prepared and administered to mice as outlined in the preceding section. Blood was recovered by cardiac puncture on anesthetized mice. Lipid and antisense recoveries were determined by standard scintillation counting techniques. Release rates were determined by measuring the [3H]/[14C] ratio over time.

The stability of the formulations was also assessed by measuring the ratio of antisense and lipid recovery in the blood at various times (FIG. 11). A ratio of 1.0 suggests that the antisense and the lipid are staying together in the circulation. The "DSPC" formulation showed little deviation from a ratio of 1.0 over 24 h, suggesting that it is very stable in the circulation. The "POPC" formulation dropped to a ratio of 0.6 after 2 h, while the ratio for the "SM" formulation decreased more slowly, reaching 0.6 after 12 h in the circulation. These results indicate that it may be possible to deliberately alter the antisense release rates by modifying the lipid composition.

4.4 PEG-Acyl Influence on Circulation Half-life of Single Dose of Thioate Antisense Encapsulated lipid-encapsulated antisense was prepared using the ethanol-citrate procedure as described in "Material and Methods". Initial lipid and antisense concentrations were 9.9 and 2 mg/mL, respectively. Liposomal formulations were composed of DSPC:CHOL:DODAP:PEG-CerC14 or C20 (25:45:20:10). The formulation contained a lipid label ([$^{14}$C]-cholesterylhexadecylether) and [$^3$H]-antisense and were injected (200 $\mu$L) intravenously via the lateral tail vein of female (20–25 g) ICR mice at a lipid dose of 120 mg/kg. Blood was recovered by cardiac puncture on anesthetized mice. Lipid and antisense recoveries were determined by standard scintillation counting techniques.

The influence of PEG-acyl chain length on clearance rates of a DSPC:CHOL:DODAP:PEG-Cer formulation was investigated using PEG-CerC14 and PEG-CerC20 (FIG. 12). The inclusion of PEG-CerC20 in the formulation resulted in enhanced circulation times over the PEG-CerC14. This corresponds to in vitro data suggesting that the C14 version of the PEG is exchanged much more rapidly out of the vesicle than the C20 version.

4.5 In vivo Efficacy of Single Dose of Lipid Encapsulated ICAM-1 (Phosphorothioate) Antisense The efficacy of PS- 3082 encapsulated in various lipid formulations containing DODAP was tested in an ear inflammation model using ICR mice.

Inflamed mice were treated at the time of ear challenge with a 30 mg/kg i.v. dose of either HBS (no oligo), EPC:CHOL liposomes with entrapped PS-3082 (identified as AS 1000), POPC:CHOL:DODAP:PEG-CerC14 with entrapped PS-3082 (identified as AS 4100), or DSPC:CHOL:DODAP:PEG-CerC14 with entrapped PS-3082 (identified as AS 4200). Ear swelling was measured at 24 hours after initiating inflammation using an engineer's micrometer.

Ear swelling measurements were made 24 hours after initiating inflammation in mice treated i.v. at the time of ear challenge with either HBS (control), PS-3082 encapsulated in EPC:CHOL vesicles (30 mg/kg dose of oligo), PS-3082 encapsulated in POPC:CHOL:DODAP:PEG-CerC14 vesicles (30 mg/kg dose of oligo), or PS-3082 encapsulated in DSPC:CHOL:DODAP:PEG-CerC14 vesicles (30 mg/kg dose of oligo) (FIG. 13). The "DSPC" formulation resulted in the greatest efficacy, exhibiting only 10% increase in ear swelling over pre-challenge values. A similar trend was observed for cellular infiltration into the "challenged" ear versus the non-treated ear (FIG. 14).

In another evaluation, mice received 10 $\mu$Ci of [$^3$H]-methylthymidine, i.p., 24 hours before initiating inflammation. Inflamed mice were treated at the time of ear challenge with a 30 mg/kg i.v. dose of either HBS (no oligo), EPC:CHOL liposomes with entrapped PS- 3082 (identified as AS 1000), POPC:CHOL:DODAP:PEG-CerC14 with entrapped PS- 3082 (identified as AS 4100), or DSPC:CHOL:DODAP:PEG-CerC14 with entrapped PS-3082 (identified as AS 4200). Cell infiltration was monitored by measuring the radioactivity in the "challenged ear" versus the non-treated ear. Results are expressed as the ratio of radioactivity in the left (challenged ear) versus right ear.

4.6 In vivo Efficacy of Single Dose of Lipid Encapsulated ICAM-1 (Phosphodiester) Antisense This experiment demonstrates the in vivo efficacy of a phosphodiester antisense oligodeoxynucleotide encapsulated in lipid particles according to the invention. In specific, the phosphodiester was targeted to the ICAM- 1 gene in an ear inflammation model.

| Group | Test Sample/Drug | Dose | Time Point |
|---|---|---|---|
| 1 | control inflammation - HBS | 200 $\mu$l | 24 hr |
| 2 | corticosteroid | 200 $\mu$l | 24 hr |
| 3 | empty vesicles | 200 $\mu$l | 24 hr |
| 4 | PS-3082 | 200 $\mu$l | 24 hr |
| 5 | PO-3082 | 200 $\mu$l | 24 hr |

Antisense Sample Preparation: Antisense was encapsulated using the standard methods of Examples 5–9, using the phosphodiester modification. The phosphodiester formulation used 10–50 mM citrate (preferably 20 mM citrate), pH 4.0 instead of 300 mM citrate, pH 4.0 preferred for phosphorothioates. Empty vesicles consisted of lipid components only. Corticosteroid (either Halobetasol propionate 0.05% by weight (Westwood Squibb, Montreal) or Dexamethasone (50 ug dissolved in 4:1 acetone:olive oil)) was applied topically in a thin film to cover the surface of the ear 15 minutes after ear challenge.

Inflammation and Dosing: Mouse ear inflammation was induced using DNFB as described above in Materials and Methods. Female ICR mice (6–8 weeks old) received intravenous tail vein injections of antisense (200 $\mu$l). Antisense doses for the phosphorothioate and phosphodiester antisense were adjusted to be 20–30 mg/kg. 6 mice were tested with each formulation. Administration occurred 15 min. after the application of 0.2% DNFB to the mouse ear. Ear measurements were made on anaesthetized mice 24 hours after treatment (unless shown otherwise) and prior to termination. Mice are terminated by cervical dislocation and the ears are removed around the pinna. Ears are then weighted, digested (Solvable) and analyzed for radioactivity by liquid scintillation counting. Ears were analyzed for 1) Ear edema—based on the increase in ear thickness due to ear swelling. Calculated by subtracting pre-ear thickness values from post-ear thickness values FIG. 21. 2) Cell infiltration—based on radioactivity accumulated in the inflamed (right) ear vs. the control (left) ear FIG. 22; and 3) Ear weights—left ear versus right ear (measurement of edema) FIG. 23.

Results: The controls consisting of buffer alone (HBS) or Empty Vesicles alone demonstrated no efficacy. Topical corticosteroid demonstrates its known excellent efficacity by reducing inflammation to below pre-challenge levels. Both the phosphorothioate and phosphodiester antisense show excellent efficacy through a systemic delivery administration, reducing the degree of inflammation by around 70% and 85%, respectively. Thus, it is possible to administer the compositions of the invention at a site where the disease site is distal to the site of the injection.

4.7 In vivo Efficacy of US3 Antisense (Tumor Window Model)

In this example, the anti-tumor activity of lipid encapsulated US3, an antisense oligonucleotide directed at the erb-B-2 gene, has been demonstrated in an in vivo human breast tumor model.

The human breast carcinoma line MDA-MB-453 was implanted in a mouse tumor window model according to the method of Wu, N. Z., Da, D., Rudoll, T. L., Needham, D., Whorton, R. & Dewhirst, M. W. 1993. Increased microvascular permeability contributes to preferential accumulation of Stealth liposomes in tumor tissue. Cancer Research 53: 3765–3770; and Dewhirst, M. W., Tso, C. Y., Oliver, R., Gustafson, C. S., Secomb, T. W. & Gross, J. F. 1989. Morpholigic and hemodynamic comparison of tumor and healing normal tissue microvasculature. Int. J. Radiat. Oncol. Biol. Phys. 17: 91–99. See also Dewhirst, M W., and Needham, D. 1995. Extravasation of Stealth Liposomes into Tumors: Direct Measurement of Accumulation and Vascular Permeability using a Skin Flap Window Chamber. In Stealth Liposomes (Eds. Lasic, D. and Martin, F.) CRC Press.

The lipid-antisense formulation consists of disteroylphosphatidylcholine (DSPC, 25 mol %), cholesterol (Chol, 45 mol %), dioleoylphosphatidyldiaminopropane, (DODAP, or AL1, 20 mol %) and PEG-ceramide (C14 chain length, 10 mol %). For some experiments detailed below, proportions and constituents were altered, but the method of preparation remained the same. Lipids were dissolved in ethanol at 20 mg/ml (PEG-ceramide at 50 mg/ml). Routinely, 1 to 2 $\mu$Ci $^{14}$C-cholesterylhexadecylether was added as a lipid radiolabel. Lipids were mixed in the correct proportions in ethanol to a final concentration of 10 mg in 400 $\mu$l. The lipid mixture was then added dropwise to phosphorothioated antisense (US3: anti-human erb-B-2 GGT GCT CAC TGC GGC (SEQ ID. No 3) dissolved in 300 mM citrate buffer pH 4.0 (600 $\mu$l to make a final volume of 1 ml). The antisense was used at a variety of concentrations, but the optimum concentration for maximum encapsulation efficiency and drug:lipid ratio was determined to be 0.5 mg/ml final. During the addition, the solution becomes opaque. The DODAP is positively charged at pH 4.0 (pKa=6.53) and so attracts the negatively charged DNA molecules. The mixture was subjected to five cycles of freezing in liquid $N_2$ and thawing at 65° C. followed by extrusion through 100 nm filters ten times at 65 ° C.

After extrusion, two methods can be used for removal of the external antisense. Firstly, the liposomes are diluted 2:1 with citrate (to reduce ethanol content to 20%) then applied to a Bio-Gel A18M 100–200 mesh column equilibrated with HBS. The column profiles shown in this report were generated in this manner. Alternatively, the liposomes are dialysed 2 h against citrate to remove ethanol, the overnight against HBS to increase the external pH. The resulting mixture is then applied to a DEAE cation exchange column to remove external oligo. This method was the routine method used for sample preparation for in vivo studies. Antisense concentrations were routinely determined by A260 measurements. Lipid concentrations were determined by scintillation counting after spiking initial mixture with a known concentration of $^3$H or $^{14}$C cholesterylhexadecyl ether, or by HPLC. Encapsulation efficiency was determined by division of the final drug to lipid ratio by the initial drug to lipid ratio.

In vivo efficacy evaluation: When the tumor in the window has reached a diameter of 2–3 mm, treatment with free or TCS-encapsulated US3 oligonucleotide is initiated. Treatment consists of a 200 ul intravenous administration (tail vein) of either free US3 or TCS-encapsulated US3 on a 3 administrations/week schedule and an antisense dose of 10 mg/kg/administration. Tumor size is monitored 3 times per week by microscopy.

Results: The TCS-encapsulated US3 oligonucleotide was very effective at preventing the growth, or causing extensive size reduction, of the MDA-MB-453 human breast carcinoma in the window model. In contrast, unencapsulated oligonucleotide was ineffective at inhibiting tumor growth.

4.8 In vivo Clearance of Various Formulations Using Alternative Amino Lipids: DODAP or DODMA Antisense particle formulations were prepared according to Example 2, with the following modifications: In assay#1 and #2, 25% AL-1 (hydrochloride salt of DODAP) and 25% free base DODAP were employed, respectively, with a concomitant reduction in the amount of DSPC. Assay#3, 4 and 5 employed 30%, 25% and 20% DODMA (free base (prepared at Inex Pharmaceuticals Corp., Burnaby BC)), respectively, again with a concomitant reduction of DSPC.

Both the encapsulation efficiency and in vivo clearance of the formulations were studied. There was no significant difference between the encapsulation or clearance of the free base or HCl salt of DODAP. Decreasing DODMA concentration (30, 25, 20%) severely decreased the encapsulation efficiency of PS-2302 (91%, 43%, 35%) and likewise the Drug/Lipid ratio of the resulting formulation.

In the clearance study outlined in FIG. 16, DODMA formulations demonstrated slightly higher rates of clearance than 25% DODAP or AL-1, although all formulations appear to be retained in the circulation to a degree which is suitable for human therapeutics.

4.9 PEG-acyl Influence on Clearance Rate of Repeat Doses of Encapsulated EGF-R Phosphorothioate Antisense Lipid-encapsulated antisense was prepared using the ethanol-citrate procedure as described above, with changes to molar ratios of components as indicated. Initial lipid and antisense concentrations were about 9.9 and 2 mg/mL, respectively. DODAP containing formulations had drug:lipid ratios of 0.15 (+/−) 0.05. Passive encapsulation systems had drug:lipid ratios of 0.03. Nine different liposomal formulations were prepared, using standard techniques, in the following molar ratios:

| Formulation | DSPC (mol %) | Chol (mol %) | DODAP (mol %) | Steric Barrier Derivatized Lipid (name: mol %) | Antisense (EGF-R 2 mg/ml) |
|---|---|---|---|---|---|
| 1 | 55 | 45 | Nil | Nil | Empty |
| 2 | 50 | 45 | Nil | ATTA8-DSPE: 5 | Empty |
| 3 | 50 | 45 | Nil | ATTA8-DSPE: 5 | AS |
| 4 | 20 | 45 | 30 | ATTA8-DSPE: 5 | AS |
| 5 | 20 | 45 | 30 | PEG-DSPE: 5 | AS |
| 6 | 25 | 45 | 25 | PEG-CerC14: 5 | Empty |
| 7 | 25 | 45 | 25 | PEG-CerC14: 5 | AS |
| 8 | 25 | 45 | 25 | PEG-CerC20: 5 | Empty |
| 9 | 25 | 45 | 25 | PEG-CerC20: 5 | AS |

Antisense ("AS") used was fully phosphorothioated EGFR (anti-human Epidermal Growth Factor Receptor) CCG TGG TCA TGC TCC (SEQ ID. No 10) (prepared by Hybridon, Inc.) PEG-CerC14 is PEG(mw2000)-Ceramide with 14 carbon acyl chain. PEG-CerC20 is PEG(mw2000)-Ceramide with 20 carbon acyl chain. PEG-DSPE is PEG(mw2000)-1,2-distearoyl-sn-glycero-3-phosphoethanolamine ATTA8-DSPE is N-(ω-N'-acetoxy-octa(14'amino-3',6',9',12'-tetraoxatetradecanoyl))- 1,2-distearoyl-sn-glycero-3- phosphoethanolamine (molec weight about 2660). Synthesis of ATTA8-DSPE is fully disclosed in U.S. Provisional Pat. Application Ser. No. 60/073,852, filed Dec. 23, 1997 and U.S. Provisional Pat. Application filed Feb. 2, 1998 both assigned to the assignee of the instant invention and incorporated herein by reference.

Each formulation contained a lipid label ([$^{14}$C]-cholesterylhexadecylether) and [$^{3}$H]-antisense, as described in Example 4.4, above. All samples were prepared in 300 mM citrate pH 4.0 containing 40% ethanol and extruded 10× through 100 nm filters. Formulations contained phosphorothioate antisense and lipid or empty lipid alone. Samples were dialyzed in HBS (20 mM Hepes, 145 mM NaCl, pH 7.45) to remove ethanol and citrate. Sample lipid concentrations were adjusted such that the injected lipid dose will be 1.8 μmol/mouse/week (5–10 mg AS per kg mouse/week). Samples were filtered (0.22 μm) prior to injection.

In this experiment female (20–25g) ICR mice (6–8 weeks old) were divided into 9 groups of 6, plus other control groups. Each group received four injections of the same formulation. All injections were 200 μL intravenous (via the lateral tail vein) at a lipid dose of 120 mg/kg. Mice were dosed every week for 3 weeks (4 injections). At 4 weeks, certain groups (treated with lipid and antisense) were given an injection of empty lipid carriers of varying composition to evaluate whether there is rapid clearance of the carrier in the absence of antisense. Blood (25 μl, pipettor) was collected 1 h post-injection each week for 3 weeks by tail nicks. Mice were weighed each week to estimate blood volume (8.0 ml whole blood/100 g body weight). Blood was placed in a glass scintillation vial containing 200 μl of 5% EDTA. Solvable (500 μl) was added and the blood was digested for 3 h at 65° C. Samples were decolorized by the addition of 100 μl 70% hydrogen peroxide. Samples were analyzed for radioactivity by liquid scintillation counting. At the end of 4 weeks, mice were terminated by $CO_2$ inhalation or cervical dislocation preceded by general anesthesia.

The results of this experiment are shown in FIG. 17. For all formulations not containing antisense ("empty liposomes") repeat dosages demonstrated circulation times reasonably consistent with the first dosage. However, when antisense is used in the formulation, it was surprisingly found that the acyl chain length of the lipid derivatized to the steric barrier (i.e. ATTA or PEG) moiety demonstrates a profound effect on clearance rates. Repeat dosages of PEG-CerC20, PEG-DSPE and ATTA8-DSPE formulations are rapidly cleared from the circulation compared to the first dosage, whereas the PEG-CerC14 formulation is reasonably consistent with the first dosage.

Similar results are demonstrated in FIG. 18. The formulations were identical to those of FIG. 17, with the additional formulation of empty vesicles using the same lipids as formulations 4 and 5.

Without intending to be bound by any particular theory of action, it is suggested by these results that lipids like the PEG-CerC14 lipid, a lipid which exchanges out of the liposome membrane with a T1/2 on the order of minutes (i.e. 1–60 mins) in blood provides a tremendous benefit over lipids like PEG-CerC20, PEG-DSPE and ATTA8-DSPE which do not exchange out, where repeat dosing of a lipid-formulated compound, such as a therapeutic compound or diagnostic compound, is required. The mammalian blood clearance response may not recognize these as foreign antigens if the derivatized lipid is removed expeditiously from the liposome surface when in circulation. However, when the derivatized-lipid remains with the formulation for extended periods, a clearance response is invoked, which causes rapid clearance upon repeat dosing. This data suggests that any lipid derivatized with a steric barrier molecule that exchanges out of the liposome membrane faster than PEG-CerC20, PEG-DSPE or ATTA8-DSPE will be superior for use in repeat dosing. For example ATTA8-DMPE, or PEG-CerC8 to C18 all being exchangeable, will have improved circulation characteristics upon repeat administration.

Taken together, it will be evident to one skilled in the art, that on the basis of these teachings, any diagnostic or therapeutic agent that may be delivered in a lipid formulation comprising a steric-barrier derivatized lipid, such as a PEG-lipid or ATTA-lipid, should be tested with both a long and short acyl-chain anchors, in order to determine which formulation is best for repeat dosings.

Further, without intending to be bound by any theory of action, the invention herein may prove to be particularly useful when the bioactive agent being delivered is a non-cytotoxic agent. Cytotoxic agents kill those cells which clear long circulating (i.e. PEG-DSPE) liposomes. This ensures that repeat dosings will not be rapidly cleared, because the cells responsible (usually macrophages) do not survive. In these situations, the acyl-chain length may not be significant. However, where the bioactive agent is non-cytotoxic, such as in the case of antisense drugs (regardless of chemistry or target), plasmids, proteins, etc., and many conventional drugs, the invention will be useful for repeat dosing.

4.10 In vivo Efficacy of Repeat Doses of Encapsulated Phosphorothioate c-myc Antisense in an Oncology Model In vivo efficacy of repeat injections of using formulations of the invention are shown in a mouse tumor system in FIG. 19. This experiment demonstrated efficacy of the antisense formulated according to the invention in a human oncology model, and showed the importance of PEG-acyl chain length on the efficacy of repeat dosings.

Lipid-antisense particle formulation: Formulations were prepared as described in these Examples.

| Formulation | DSPC (mol %) | Chol (mol %) | DODAP (mol %) | Steric Barrier Derivatized Lipid (name: mol %) | Antisense (c-myc 2 mg/ml) |
|---|---|---|---|---|---|
| HBS Buffer | | | | | Empty |
| AS4200 (c-myc) | 25 | 45 | 25 | PEG-CerC14: 5 | LR-3280 |
| AS4204 (c-myc) | 25 | 45 | 25 | PEG-CerC20: 5 | LR-3280 |
| AS4204 (c-myc SCR) | 25 | 45 | 25 | PEG-CerC20: 5 | c-myc SCR |
| AS4204 (PS-2302) | 25 | 45 | 25 | PEG-CerC20: 5 | PS-2302 |
| A54204 (PS-3082) | 25 | 45 | 25 | PEG-CerC20: 5 | PS-3208 |
| c-myc | | | | | LR-3280 |
| c-myc SCR | | | | | c-myc SCR |
| PS-2302 | | | | | PS-2302 |
| PS-3082 | | | | | PS-3082 |
| AS4200 (no antisense) | 25 | 45 | 25 | PEG-CerC14: 5 | Empty |
| AS4204 (no antisense) | 25 | 45 | 25 | PEG-CerC20: 5 | Empty |

-continued

| Formulation | DSPC (mol %) | Chol (mol %) | DODAP (mol %) | Steric Barrier Derivatized Lipid (name: mol %) | Antisense (c-myc 2 mg/ml) |
|---|---|---|---|---|---|

Antisense used were:

| LR-3280: | human c-myc gene (phosphorothioate) AAC GTT GAG GGG CAT | (SEQ ID. No 4) |
|---|---|---|
| c-myc SCR: | GAA CGG AGA CGG TTT | (SEQ ID. No 17) |
| PS-2302 | human ICAM-1 (phosphorothioate) GCCCAAGCTGGCATCCGTCA | (SEQ ID. No 2) |
| PS-3082 | murine ICAM-1 (Intracellular Adhesion Molecule-1) (phosphorothioate) TGCATCCCCCAGGCCACCAT | (SEQ ID. No 1) |

Formulations were diluted in filtered HBS, pH 7.6 to achieve required antisense dose (i.e. lipid dose decreases as well). Samples were filtered (0.22 μm) prior to injection. External buffer was HBS (20 mM Hepes, 145 mM NaCl, pH 7.6). Free antisense was dissolved in HBS and adjusted to the required dose by A260 (Extinction coefficients: active and control c-myc=30.6, PS-2302=32.8, PS-3082=33.6).

Tumour Inoculum: B16/BL6 murine melanoma cells were maintained in culture in MEM media supplemented with 10% FBS. On day 0 of the study, $3 \times 10^5$ cells were injected sub-cutaneously (s.c.) into the dorsal flank (injection volume: 50 μl) of female C57BL/6 mice (20–23 g). Typically, 15% extra mice will be injected so non-spheroidal tumours or mice in which no tumours are observed can be excluded from the study. Tumours were allowed to grow for a period of 5–7 days until tumors reached 50–100 mm³ prior to initiating treatments with test samples/controls.

Treatment: On the day of first treatment mice with acceptable tumours were randomly grouped with 5 animals per group. Treatment began when tumours were 50–100 mm³. Mice were dosed every other day for a total of 7 doses. Administrations were via intravenous tail vein injections (200 μl). Initial drug:lipid ratio of formulation was 0.20 (w/w) and the final drug:lipid ratio (0.14) was held constant; consequently, the lipid concentration varied as samples were diluted to the desired antisense concentration. The antisense dose was 10 mg/kg.

Endpoints: Primary tumour volume was measured using calipers. Length (mm) and width (mm) measurements were made every other day (on non-injection days) for the duration of the study. Tumour height measurements (mm) were made when feasible. Tumour volumes were calculated using the following formulas:

Tumour Volume $(mm^3) = (L \times W^2)/2$   #1

Tumour Volume $(mm^3) = (L \times W \times H) \times \pi/6$   #2

Mice were euthanized when tumour volumes reach 10% of body weight or on the first signs of ulceration. Mouse weights were recorded every day during the dosing portion of the study. On termination, all tumours were excised, weighed, observed by FACS analysis or by Northern/Western analysis. Mice were euthanized by $CO_2$ inhalation or cervical dislocation preceded by general anesthesia.

Results: FIG. 9 shows weights of tumors excised and weighed at day 18 for all groups treated with antisense at 10 mg/kg/dose compared with empty lipid controls. Tumour sizes for the AS4200(c-myc) group exhibited the best efficacy and were very consistent with only small ranges in tumour volumes observed (285–451 mm³). The group treated with free c-myc also resulted in smaller tumours but exhibited more variability in tumour volume (156–838 mm³). The encapsulated c-myc controls (c-myc SCR/PS-2302/PS-3082), AS4204(c-myc), empty lipid carriers, and free antisense controls, however, showed no inhibitory effect on tumor volumes over the 18 days when compared to HBS controls.

c-myc expression in tumor tissue was also evaluated by FACS. A correlation between tumour size and c-myc protein expression was detected (data not shown).

To determine the importance of the stability of the PEG-polymers, PEG-acyl chain length was evaluated using formulations containing PEG-CerC14 and PEG-CerC20. Interestingly, the formulation containing the PEG-CerC20 (AS4204) showed no apparent efficacy at any of the doses studied. The PEG-CerC14 formulation (AS4200) showed a dose response. The difference observed between the PEG-CerC14 and PEG-CerC20 formulations may reflect the rapid clearance phenomenon that has been observed in other models.

To establish the tolerability of free and encapsulated antisense, mouse weights were measured on a daily basis during the treatment phase of the study. No significant changes in mouse weights for either free or encapsulated formulations were apparent over the course of the dosing phase or throughout the study.

EXAMPLE 5

This example illustrates a high efficiency formulation according to Example 2, but instead of phosphorothioate antisense, employing 1) a phosphodiester antisense compound having exclusively phosphodiester internucleotide linkages (PO-2302 anti-human ICAM-1 GCCCAAGCTG-GCATCCGTCA (SEQ ID. No 1)) prepared by Inex Pharmaceuticals (USA), Inc., Hayward Calif.) or 2) ribozyme molecule to VEGF-R-1 (human Vascular Endothelial Growth Factor Receptor 1) comprising a modified RNA sequence of GAG UUG CUG AUG AGG CCG AAA GGC CGA AAG UCU G (SEQ ID. No 16).

A 15 mer of [³H]-phosphodiester antisense oligodeoxynucleotide (PO-2302) in citrate buffer, pH 3.80 (experiments ranged from 10–1000 mM citrate) was mixed with an ethanol solution of lipid (DSPC:CHOL:DODAP:PEG-CerC14; 25:45:20:10, molar ratio) at final concentrations of 2 mg/mL and 9.9 mg/mL, respectively. The final ethanol concentration in the 1 ml preparation was 38% vol/vol. The sample was extruded ten times through three 100 nm filters as described in "Materials and Methods". The sample was dialyzed for 2–3 hours in citrate buffer, pH 3.80 (same molarity as experiment), to remove a majority of the excess ethanol. The samples were switched to HEPES-buffered saline (HBS), pH 7.50, and dialyzed for a minimum of 12 hours to replace the external citrate buffer with HBS. Non-encapsulated antisense was removed either by this regular dialysis, tangential flow dialysis, or chromatography. Encapsulation was assessed either by analyzing the pre-column and post-column ratios of [³H]-antisense and [¹⁴C]-lipid or by determining the total pre-column and post-column [³H]-antisense and [¹⁴C]-lipid radioactivity.

FIG. 15 illustrates results. Encapsulation efficiency was over 50% across the 10–50 mM citrate range, and all final (administration ready) drug:lipid ratios were greater than 10% by weight. Parallel experiments varying citrate concentration were conducted with phosphorothioate antisense PS-2302. Results are also above 50% encapsulation, and in fact show a higher encapsulation efficiency than phosphodiesters, particularly at higher citrate concentrations.

This experiment was repeated using 20 mM citrate instead of 300 mM citrate to encapsulate the ribozyme molecule to VEGF-R-1 (human Vascular Endothelial Growth Factor Receptor 1) GAG UUG CUG AUG AGG CCG AAA GGC CGA AAG UCU G (SEQ ID. No 16). FIG. 20 shows the encapsulation efficiency of the ribozyme at was over 50%, approximately the same as the phosphodiester.

EXAMPLE 6

This example illustrates a high efficiency formulation as in Example 5, but replacing DODAP with an alternative protonatable lipid. Typically, the preparation for the alternative will be X:DSPC:CHOL:PEG-CerC14 at 20:25:45:10 molar ratio where X can be DODAC, OA, DODMA or any other lipid suitable for the invention.

Materials: distearoylphosphatidylcholine, DSPC; cholesterol, CHOL (both from Northern Lipids, Vancouver, BC); N,N-dioleyl-N,N-dimethylammonium chloride, DODAC; Oleylamine, OA (prepared by Steve Ansell, Inex); N-(1-(2,3-Dioleoyloxy) propyl)-N,N,-dimethyl ammonium chloride, DODMA(Avanti Polar Lipids, Alabaster AB, chloride salt prepared by Steve Ansell, INEX); poly(ethylene glycol)2000 coupled to a ceramide derivative with 14 carbon acyl chains, PEG-CerC14 (Zhou Wang, INEX Pharmaceuticals); 13×100 mm glass tube; filter sterilized 300 mM citrate buffer, pH 3.9–4.0 (use a 0.2 $\mu$m filter). Fully thioated c-myc antisense (INEX (USA), Hayward Calif.), Anhydrous Ethanol (Commercial Alcohols, Toronto, On), Citric acid, Monobasic Sodium phosphate, Dibasic Sodium phosphate, Sodium hydroxide, HEPES (BDH, Mississauga On). Deionized water, Chloroform, Methanol, Oligreen™ oligonucleotide reagent (Molecular Probes, Eugene Oreg.), Sodium chloride, Triton X-100, alcohol dehydrogenase reagent kit, (Sigma Chemical Co., St Louis Mo.), Lipid stock solutions were made in 100% ethanol with the working concentrations of the lipids which is as follows:

DSPC, 20 mg/ml; CHOL, 20 mg/ml (not very soluble above this concentration); DODMA, 20 mg/ml; PEG-CerC14; 50 mg/ml.

To prepare stock solutions of antisense, the antisense molecules were dissolved in the filtered 300 mM citrate buffer at a concentration of 3.33 mg/ml. Lipids were mixed in the desired proportions in a 13×100 mm glass tube to achieve a final volume of 0.4 ml of lipids using 100% ethanol as listed in table 1, below:

TABLE 1

Proportional mixture of lipids in a 13 × 100 mm glass test tube.

| Lipid | Mol % | M. Wt. | mg | $\mu$mol | Stock (mg/ml) | Vol of Stock ($\mu$l) |
|---|---|---|---|---|---|---|
| DODMA | 20 | 652.6 | 1.69 | 2.60 | 20 | 84.5 |
| DSPC | 25 | 790 | 2.57 | 3.25 | 20 | 115 |
| CHOL | 45 | 386.7 | 2.26 | 5.85 | 20 | 113.1 |
| PEG-CerC14 | 10 | 2600 | 3.38 | 1.30 | 50 | 67.6 |
|  | 100 |  | 9.9 | 13.00 |  | 380.2 |

In a separate 13×100 mm glass tube, 0.6 ml of antisense at 3.33 mg/ml was added. The pH of this solution should be 3.9–4.0. (NOTE: the antisense concentration is NOT determined by weight but rather by measuring absorbance at 260 nm). The lipid mixture solution was warmed to 65° C. for about 2 minutes. The antisense tube was vortexed and during this time, using a Pasteur pipette, the lipids (in ethanol) were added slowly in a dropwise manner. The mixture will get "cloudy" and some bubbles may be observed due to the ethanol, but no aggregates should be present. The resulting volume of the antisense-lipid mixture was 1.0 ml with a 10 mg (13 umol) total lipid at 13 $\mu$mols, 2 mg of antisense, and 38% ethanol, vol/vol. It can be expected that the pH to rise to about 4.4.

The antisense-lipid mixture was subjected to 5 (five) cycles of freezing in liquid nitrogen and thawing at 65° C. in a waterbath. After each thaw, the mixture was vortexed briefly. Subsequently, the mixture was passed 10 times through three stacked 100 nm polytcarbonate filters (Poretics) or extruded using a pressurized extruder apparatus with a thermobarrel attachment (Lipex Biomembranes). The temperature and nitrogen pressure during extrusion were 65° C. and no more than 200 psi to 300 psi, respectively. Each pass should take no more than 2 minutes and is vortexed after each pass.

After extrusion, the mixture was dialyzed in a dialysis tubing (3500 Mwt cutoff; SpectraPor) for 1 hour in 300 mM citrate at pH 3.9–4.0, removing the ethanol. The mixture was transferred into 5 L of HBS buffer at pH 7.5 and allowed to further dialyze to a minimum of 12 hours, to neutralize the DODMA and release any surface bound antisense associated with the vesicles. Alternatively, tangential flow dialysis, ion exchange-chromatography or gel filtration chromatography can be used to process the extruded antisense-lipid mixture to an administration ready preparation.

EXAMPLE 7

This example illustrates a high efficiency formulation as in Example 5, but replacing DSPC with SM to generate a preparation of DODAP:SM:CHOL:PEG-CerC14 at 20:25:45:10 molar ratio. Antisense is processed with the formulation for a standard 1.0 ml volume, which can be scaled up proportionately as required.

Materials: Sphingomyelin SM; cholesterol, CHOL; dimethylaminopropane, DODAP; polyethylene glycol coupled to a ceramide derivative with 14 carbon acyl chains, PEG-CerC14; 13×100 mm glass tube; filter sterilized 300 mM citrate buffer, pH 3.9–4.0 (use a 0.2 $\mu$m filter).

Lipid stock solutions were made in 100% ethanol with the working concentrations of the lipids which is as follows:

SM, 20 mg/ml; CHOL, 20 mg/ml (not very soluble above this concentration); DODAP, 20 mg/ml; PEG-CerC14; 50 mg/ml.

To prepare stock solutions of antisense, the antisense molecules were dissolved in the filtered 300 mM citrate buffer at a concentration of 3.33 mg/ml. Lipids were mixed in the desired proportions in a 13×100 mm glass tube to achieve a final volume of 0.4 ml of lipids using 100% ethanol as listed in Table 2, below:

TABLE 2

Proportional mixture of lipids in a 13 × 100 mm glass test tube.

| Lipid | Mol % | M. Wt. | mg | $\mu$mol | Stock (mg/ml) | Vol of Stock ($\mu$l) |
|---|---|---|---|---|---|---|
| DODAP | 20 | 684.5 | 1.78 | 2.60 | 20 | 89.0 |
| SM | 25 | 703 | 2.30 | 3.27 | 20 | 115 |
| CHOL | 45 | 386.7 | 2.26 | 5.85 | 20 | 113.1 |
| PEG-CerC14 | 10 | 2600 | 3.38 | 1.30 | 50 | 67.6 |
|  | 100 |  | 9.72 | 13.02 |  | 384.7 |

In a separate 13×100 mm glass tube, 0.6 ml of antisense at 3.33 mg/ml was added. The pH of this solution should be 3.9–4.0. (NOTE: the antisense concentration is NOT determined by weight but rather by measuring absorbance at 260 nm). The lipid mixture solution was warmed to 65° C. for about 2 minutes. The antisense tube was vortexed and during this time, using a Pasteur pipette, the lipids (in ethanol) were added slowly in a dropwise manner. The mixture will get "cloudy" and some bubbles may be observed due to the ethanol, but no aggregates should be present. The resulting volume of the antisense-lipid mixture was 1.0 ml with a 10 mg (13 umol) total lipid at 13 μmols, 2 mg of antisense, and 38% ethanol, vol/vol. It can be expected that the pH to rise to about 4.4.

The antisense-lipid mixture was subjected to 5 (five) cycles of freezing in liquid nitrogen and thawing at 65° C. in a waterbath. After each thaw, the mixture was vortexed briefly. Subsequently, the mixture was passed 10 times through three stacked 100 nm polytcarbonate filters (Poretics) or extruded using a pressurized extruder apparatus with a thermobarrel attachment (Lipex Biomembranes). The temperature and nitrogen pressure during extrusion were 65° C. and no more than 200 psi to 300 psi, respectively. Each pass should take no more than 2 minutes and is vortexed after each pass.

After extrusion, the mixture was dialyzed in a dialysis tubing (3500 Mwt cutoff; SpectraPor) for 1 hour in 300 mM citrate at pH 3.9–4.0, removing the ethanol. The mixture was transferred into 5 L of HBS buffer at pH 7.5 and allowed to further dialyze to a minimum of 12 hours, to neutralize the DODAP and release any surface bound antisense associated with the vesicles. Alternatively, tangential flow dialysis, ion exchange-chromatography or gel filtration chromatography can be used to process the extruded antisense-lipid mixture to an administration ready preparation.

EXAMPLE 8

This example illustrates a high efficiency formulation as in Example 5, but replacing PEG-CerC14 with ATTA8-DSPE to prepare DODAP:DSPC:CHOL:ATTA8-DSPE at 40:10:45:5 molar ratio of antisense formulation.

Materials: distearoylphosphatidylcholine, DSPC; cholesterol, CHOL; dimethylaminopropane, DODAP; N-(ω-N'-acetoxy-octa(14'amino-3', 6', 9', 12'-tetraoxatetradecanoyl))-1,2-distearoyl-sn-glycero-3-phosphoethanolamine, ATTA8-DSPE; 13×100 mm glass tube; filter sterilized 300 mM citrate buffer, pH 3.9–4.0 (use a 0.2 μm filter).

Lipid stock solutions were made in 100% ethanol with the working concentrations of the lipids which is as follows:

DSPC, 20 mg/ml; CHOL, 20 mg/m/l (not very soluble above this concentration); DODAP, 20 mg/ml; ATTA8-DSPE; 50 mg/ml.

To prepare stock solutions of antisense, the antisense molecules were dissolved in the filtered 300 mM citrate buffer at a concentration of 3.33 mg/ml. Lipids were mixed in the desired proportions in a 13×100 mm glass tube to achieve a final volume of 0.4 ml of lipids using 100% ethanol as listed in Table 3, below:

TABLE 3

Proportional mixture of lipids in a 13 × 100 mm glass test tube.

| Lipid | Mol % | M. Wt. | mg | μmol | Stock (mg/ml) | Vol of Stock (μl) |
|---|---|---|---|---|---|---|
| DODAP | 40 | 684.5 | 4.16 | 6.08 | 20 | 208 |
| DSPC | 10 | 790 | 1.2 | 1.52 | 20 | 60 |
| CHOL | 45 | 386.7 | 2.6 | 6.72 | 20 | 130 |
| ATTA8-DSPE | 5 | 2638 | 2.0 | 0.76 | 50 | 40 |
| | 100 | | 10.26 | 15.1 | | 438 |

In a separate 13×100 mm glass tube, 0.6 ml of antisense at 3.33 mg/ml was added. The pH of this solution should be 3.9–4.0. (NOTE: the antisense concentration is NOT determined by weight but rather by measuring the absorbance at 260 nm). The lipid mixture solution was warmed 65° C. for about 2 minutes. The antisense tube was vortexed and during this time, using a Pasteur pipette, the lipids (in ethanol) were added slowly in a dropwise manner. The mixture will get "cloudy" and some bubbles may be observed due to the ethanol, but no aggregates should be present. The resulting volume of the antisense-lipid mixture was 1.0 ml with a 10 mg (13 umol) total lipid at 13 μmols, 2 mg of antisense, and 38% ethanol, vol/vol. It can be expected that the pH to rise to about 4.4.

The antisense-lipid mixture was subjected to 5 (five) cycles of freezing in liquid nitrogen and thawing at 65° C. in a waterbath. After each thaw, the mixture was vortexed briefly. Subsequently, the mixture was passed 10 times through three stacked 100 nm polytcarbonate filters (Poretics) or extruded using a pressurized extruder apparatus with a thermobarrel attachment (Lipex Biomembranes). The temperature and nitrogen pressure during extrusion were 65° C. and no more than 200 psi to 300 psi, respectively. Each pass should take no more than 2 minutes and is vortexed after each pass.

After extrusion, the mixture was dialyzed in a dialysis tubing (3500 Mwt cutoff; SpectraPor) for 1 hour in 300 mM citrate at pH 3.9–4.0, removing the ethanol. The mixture was transferred into 5 L of HBS buffer at pH 7.5 and allowed to further dialyze to a minimum of 12 hours, to neutralize the DODAP and release any surface bound antisense associated with the vesicles. Alternatively, tangential flow dialysis, ion exchange-chromatography or gel filtration chromatography can be used to process the extruded antisense-lipid mixture to an administration ready preparation.

EXAMPLE 9

This example illustrates use of tangential flow dialysis to clean up a large scale (>50 ml) preparation of extruded antisense-lipid mixture to obtain an administration ready preparation. Tangential Flow Diafiltration has been shown to be useful in four functions in the formulation process 1) buffer exchange, 2) removal of ethanol, 3) removal of unencapsulated antisense and 4) concentration of the formulation. Using TF it is demonstrated that it is possible to efficiently exchange these components using only 10–15 sample volumes with a single buffer system at a very significant reduction in the process time.

Materials for Tangential Flow Dialysis: Microcross Sampler™ Tangential Flow column (Microgon, Laguna Hills, Calif.) Masterflex™ console drive and Easyload™ Pump head (Cole-Palmer, Vernon Hills Ill.), Extruder (Lipex Biomembranes, Vancouver BC), Polycarbonate membranes, 100 μm, (AMD Manufacturing, Mississauga On).

Antisense (c-myc) is prepared by dissolving in 300 mM Na Citrate buffer to a final concentration of 4.17 mg/ml for c-myc as verified by absorbance at 260 nm. The antisense stock solution is typically warmed to 65° C. for 2 minutes to dissolve and to remove secondary structure. AS4200 consists of DODAP:DSPC:CHOL:PEG-CER-14 at the percent mol ratio of 25:20:45:10 and the lipids are aliquoted from stock solutions to a total concentration of 10 mg/0.400 ml in anhydrous ethanol. In this study 50–60 ml scale formulations were produced. Thus 20–24 ml of the ethanolic lipid solution is added dropwise, at room temperature, using a peristaltic pump at 1 ml/nin into 30–36 ml of the AS solution which is stirring in a 100 ml round bottom flask with a 2 cm magnet stir bar (Stirrer setting 2–3). After mixing, the lipid/antisense suspension was pipetted into a 100 ml extruder prepared with 2–3, 100 µm polycarbonate membranes and pre-equilibrated at 65° C. The suspension was extruded using ten passes at ~300 psi. After extrusion the formulation was processed using tangential flow diafiltration.

Tangential Flow Ultrafiltration. A 230 $cm^2$ Microcross tangential flow cartridge (50 kDa cut off) was attached to a Masterflex peristaltic pump, sample reservoir and buffer reservoir using Tygon tubing. The tubing length was adjusted so that the total circuit of tubing, pump and TF cartridge had a total dead volume of 30 ml. To this system a 60 ml sample reservoir was attached. The sample was loaded into the tubing and reservoir by running the peristaltic pump at a low speed. After loading, the system was closed and the pump speed gradually increased to the pump maximum (approx. 100 ml/min) until the initial TF cartridge inlet pressure was 12–15 psi and the outlet pressure was 8–11 psi. When the system pressure stabilized, both the filtrate outlet and the buffer reservoir were opened. Opening these valves allowed filtrate to flow out of the cartridge at ~10–15 ml/min while wash buffer (i.e. PBS, pH 7.5) was being collected. For a 50–60 ml formulation 700–900 ml of buffer was used to "wash" the sample. Fractions (10 ml) of the filtrate were collected for analysis of ethanol removal, pH, and antisense. After diafiltration was completed the wash buffer reservoir was closed and with the pump continuing to run, filtrate was allowed to flow, concentrating the sample, typically reducing the preparation volume to the tubing dead volume (30–35 ml). The sample was collected from the system and the tubing and column were washed with 15 ml wash buffer to remove any remaining formulation.

Antisense Quantification. Antisense concentration was normally determined by measuring absorbance at 260 nm as outlined in the current protocol. Briefly, antisense stock solutions were quantified by diluting 1:500 in MilliQ water and measuring absorbance. TF filtrate fractions were diluted 1:10 in MilliQ water and absorbance was measured. Antisense in suspension with lipids was measured by adding 10 µl of the suspension to 250 µl MilliQ water. A monophase was created by adding 750 µl $CHCl_3$/MeOH (2.1:1) and 100 µl MeOH. Immediately after vortexing the mixture the absorbance was measured at 260 nm. In each case the extinction coefficient for the given antisense was multiplied by the dilution factor to determine the antisense concentration.

Lipid Quantification. As outlined in the current protocol, 50 µl aliquots of the lipid/antisense suspension was diluted with 100 µl MilliQ water and submitted for analysis by HPLC. The percent encapsulation efficiency of the formulation is determined by dividing the Drug/Lipid ratio of the finished product by the initial Drug/Lipid ratio formed when the lipid and antisense stock solutions are mixed.

Ethanol Assay. Ethanol in the TF filtrate was determined using an alcohol dehydrogenase reagent kit supplied by Sigma Chemical Co.

DEAE Sephadex chromatography. A suspension of the processed formulation was loaded onto a 1×10 cm column of DEAE sephadex equilibrated in 20 mM PBS, pH 7.5. After eluting through the column the formulation was collected into a sterile falcon tube. The volume, antisense and lipid concentration were measured to determine recovery.

Particle Size. The particle size of the formulation was measured by QELS using a Nicomp Particle sizer, (Nicomp, Santa Barbara, Calif.) and particle sizes are reported in the particle mode with volume weighing.

| | Results of Large Scale Preparations: | | | | | | |
|---|---|---|---|---|---|---|---|
| Assay | Initial Lipid Content (mg/ml) | Initial Antisense Content (mg/ml) | Final Lipid Content (mg/ml) | Final Antisense Content (mg/ml) | Initial Drug:Lipid | Final Drug:Lipid | Encaps. Effic. |
| A | 10.581 | 1.936 | 14.604 | 1.681 | 0.183 | 0.115 | 63% |
| B | 8.727 | 2.284 | 7.926 | 1.008 | 0.262 | 0.127 | 48% |
| C | 11.06 | 2.97 | 2.69 | 0.556 | 0.286 | 0.207 | 77% |

EXAMPLE 10

Phosphodiester and phosphorothioate antisense oligonucleotides encapsulated according to the methods in Example 2 and 5–9 were examined for their relative susceptibility to nuclease digestion by serum or S1 nuclease. Protection of the phosphodiester-linked oligonucleotide was significantly higher in serum when encapsulated as opposed to the free, raising the $T_{1/2}$ of degradation from 10 mins to at least 8 h. Free phosphorothioate oligodeoxynucleotide showed significant breakdown in serum within 30 minutes, however encapsulated phosphorothioate oligodeoxynucleotide did not show any sign of degradation even after 24 h incubation in serum. In vivo data agrees with these findings, showing no sign of degradation of the encapsulated phosphorothioate antisense until 8 h.

As a positive control, the free phosphodiester and phosphorothioate antisense were subjected to very potent levels of S1 nuclease (100U/50 µg) (1U of S1 nuclease will digest 1 ug DNA per minute at 37° C.). The enzyme completely digested the free phosphodiester and phosphorothioate within seconds after its addition. The encapsulated phosphodiester under the same conditions was over 90% intact at 24 h, and the encapsulated phosphorothioate was fully intact at 24 h.

The experiments were conducted as described in the specification, or modified as follows.

S1 Nuclease Digestion. 50 µg aliquots containing free, encapsulated, or encapsulated +0.5% Triton X100 were aliquoted into 1.5 ml eppendorf tubes. To the tubes were added 10 µl 10×S1 nuclease buffer, dH2O (to make final volume 100 µl), and, just prior to digestion, 100U of S1 nuclease to each eppendorf tube. The tubes were sealed with parafilm and incubated at 55° C. A sample of the free, encapsulated, or encapsulated +0.5% Triton X100 not digested by nuclease (standard) was frozen in liquid nitrogen in an eppendorf tube and stored at −20° C. At each desired time point, an aliquot of each sample was collected, added to GDP buffer containing proteinase K (133 µg/ml) and immediately frozen in liquid nitrogen in order to stop the reaction. Once all of the time points were collected, the samples were incubated at 55° C. in a waterbath to activate proteinase K enabling it to denature any remaining S1 nuclease. Proteinase K digested samples were applied to polyacrylamide gels, described below, to assess levels of S1 nuclease degradation Normal Murine/Human Serum Digestion. 50 µg of the free, encapsulated, or encapsulated +0.5% Triton X100 was aliquoted into 1.5 ml eppendorf tubes. To the tubes we added 45 µl normal murine/human serum, dH2O (to make final volume 50 µl), to each eppendorf tube. The tubes were sealed with parafilm and incubated at 37° C. A sample of the free, encapsulated, or encapsulated +0.5% Triton X100 not digested by nuclease (standard) was frozen in liquid nitrogen in an eppendorf tube and stored at −20° C. Aliquots were taken at various time points, added to GDP buffer containing proteinase K (133 µg/ml) and immediately frozen in liquid nitrogen to stop the reaction. Once all of the time points were collected, the samples were incubated at 55*C. in a waterbath to activate proteinase K enabling it to denature any remaining exonuclease. Proteinase K digested samples were applied to polyacrylamide gels to assess levels of exonuclease degradation Micrococcal Nuclease. An alternative standard nuclease assay not employed in the present experiment is the assay disclosed by Rahman et al. U.S. Pat. No. 5,665,710, wherein nucleic acid/lipid particles are incubated for 30 mins at 37° C. in presence of an excess of micrococcal nuclease in 1 mM CaCl$_2$.

Polyacrylamide Gel Electrophoresis (PAGE). Prepared 14 cm×16 cm×7.5 mm polyacrylamide (15% or 20%) gels in 7M urea and TBE. Approximately 300 ng of sample (at each time point) and standard were aliquoted into eppendorf tubes. An equivalent volume of 2× loading buffer was added to each sample. The samples were then heated in a waterbath to 90° C. for 3 min to reduce secondary structures and then applied to the gel. The loaded gel was electrophoresed at 600V for 10 min (to sharpen the band) and then at 300V for the duration of the gel. The gel was incubated in 1×SyberGreen I stain in TBE for a minimum of 15 min and then photographed while illuminated under UV light (3.5 sec exposure, 4.5 aperture).

VII. Conclusion

As discussed above, the present invention provides methods of preparing lipid-encapsulated therapeutic agent (nucleic acid) compositions in which the therapeutic agent (nucleic acid) portion is encapsulated in large unilamellar vesicles at a very high efficiency. Additionally, the invention provides compositions prepared by the method, as well as methods of introducing therapeutic agents (nucleic acids) into cells. The compositions are surprisingly efficient in transfecting cells, both in vivo and in vitro.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A composition comprising lipid-therapeutic agent particles comprising a lipid portion and a charged therapeutic agent, said charged therapeutic agent being encapsulated in said lipid portion, wherein said lipid portion comprises a first lipid component, a second lipid component, a third lipid component, and a fourth lipid component, said first lipid component being selected from among lipids containing a protonatable or deprotonatable group that has a pKa such that the lipid is in a charged form at a first pH and a neutral form at a second pH, wherein the pKa of the first lipid component is in the range of from 4 to 11, and said first lipid component being further selected such that the charged form is cationic when the therapeutic agent is anionic and anionic when the therapeutic agent is cationic, said second lipid component being selected from among lipids that prevent particle aggregation during lipid-therapeutic agent particle formation and which exchange out of the lipid particle at a rate greater than PEG-CerC20, said third lipid component being a neutral lipid selected from the group consisting of DSPC, POPC, DOPE, and SM, and said fourth lipid component being Chol.

2. The composition according to claim 1, wherein at least some of the protonatable or deprotonatable groups are disposed on the exterior surface, of the particles and at least some of these groups have been neutralized.

3. The composition according to claim 2, wherein the therapeutic agent is anionic.

4. The composition according to claim 3, wherein the therapeutic agent is a polyanionic nucleic acid.

5. The composition according to claim 4, wherein the polyanionic nucleic acid is an antisense nucleic acid.

6. The composition according to claim 4, wherein at least 50% of the polyanionic nucleic acid in the composition is encapsulated within the particle.

7. The composition of claim 4, wherein at least 90% of the polyanionic nucleic acid in the composition is encapsulated within the particle.

8. The composition of claim 4, wherein the polyanionic nucleic acid has exclusively phosphodiester linkages.

9. The composition of according to claim 3, wherein the first lipid component is an amino lipid.

10. The composition of claim 9, wherein the second lipid component is a polyethylene glycol-modified or polyamide oligomer-modified lipid.

11. The composition of claim 3, wherein the second lipid component is a polyethylene glycol-modified or polyamide oligomer-modified lipid.

12. A composition comprising lipid-therapeutic agent particles comprising a lipid portion and a charged therapeutic agent, said charged therapeutic agent being encapsulated in said lipid portion, wherein said lipid portion comprises a first lipid component, a second lipid component, a third lipid component and a fourth lipid component, said first lipid component being selected from among lipids containing a protonatable group that has a pKa such that the lipid is in a charged form at a first pH and a neutral form at a second pH, and said second lipid component being selected from among lipids that prevent particle aggregation during lipid-nucleic acid particle formation, said third lipid component being a neutral lipid selected from the group consisting of DSPC, POPC, DOPE, and SM, and said fourth lipid component being Chol, said particles having a nucleic acid/lipid ratio of at least 10% by weight and a size of from about 70 to about 200 nm, wherein said therapeutic agent is a polyanionic nucleic acid, said nucleic acid having exclusively phophodiester linkages, and wherein at least some of said protonatable groups are disposed on the exterior surface of the particles and at least some of these groups have been neutralized.

13. The composition according to claim 12, wherein the nucleic acid is an antisense nucleic acid.

14. The composition of according to claim 12, wherein the first lipid component is an amino lipid.

15. The composition of claim 14, wherein the second lipid component is a polyethylene glycol-modified lipid.

16. The composition of claim 12, wherein the second lipid component is a polyethylene glycol-modified lipid.

17. The composition of claim 12, wherein the first lipid component is an amino lipid, and the second component is PEG-modified or polyamide oligomer-modified lipid, and wherein said lipids are present at molar percents of about 25–45% neutral lipid, about 35–55% cholesterol, about 10–40% amino lipid and about 0.5–15% PEG-modified or Polyamide oligomer-modified lipid.

18. The composition of claim 12, wherein said lipid portion comprises DODAP as the first lipid component, DSPC as the neutral lipid, and PEG-CerC14 as the second lipid component.

19. The composition of claim 18, wherein the lipid components are present in molar percents of about 25–45% DSPC, about 35–55% Chol, about 10–40% DODAP and about 0.5–15% PEG-CerC14.

20. The composition of claim 12, wherein said lipid portion comprises DODAP, POPC, Chol and PEG-CerC14.

21. The composition of claim 12, wherein said lipid comprises of DODAP, SM, Chol and PEG-CerC14.

22. The composition according to claim 12, wherein at least 50% of the nucleic acid in the composition is encapsulated within the particle.

23. The composition of claim 12, wherein at least 90% of the nucleic acid in the composition is encapsulated within the particle.

24. The composition of claim 12, wherein said nucleic acid is a ribozyme.

25. The composition of claim 14, wherein the second lipid component is a polyethylene glycol-modified or polyamide oligomer-modified lipid.

26. The composition of claim 12, wherein the second lipid component is a polyethylene glycol-modified or polyamide oligomer-modified lipid.

27. A method for preparation of a composition comprising lipid-encapsulated therapeutic agent particles, said method comprising the steps of:

(a) preparing a mixture of lipids comprising a first lipid component, a second lipid component, a third lipid component, and a fourth lipid component, and combining the mixture of lipids with a buffered aqueous solution of a charged therapeutic agent to form an intermediate mixture containing lipid-encapsulated therapeutic agent particles having exterior surface charges, wherein said first lipid component is selected from among lipids containing a protonatable or deprotonatable group that has a pKa such that the lipid is in a charged form at a first pH and a neutral form at a second pH, wherein the pKa of the first lipid component is in the range of from 4 to 11, said buffered solution having a pH such that the first lipid component is in its charged form when in the buffered solution, said first lipid component being further selected such that the charged form is cationic when the charged therapeutic agent is anionic in the buffered solution, and anionic when the charged therapeutic agent is cationic in the buffered solution, and said second lipid component being selected from among lipids that prevent particle aggregation during lipid-therapeutic agent particle formation, said third lipid component being a neutral lipid selected from the group consisting of DSPC, POPC, DOPE, and SM, and said fourth lipid component being Chol, and (b) changing the pH of the intermediate mixture to neutralize at least some of the exterior surface charges on said lipid-encapsulated therapeutic agent particles to provide at least partially-surface neutralized lipid-encapsulated therapeutic agent particles.

28. The method of claim 27, wherein said composition consists essentially of lipid-nucleic acid particles, said particles having a size of from 70 nm to about 200 nm.

29. The method of claim 27, wherein said mixture of lipids in step (a) is a mixture of lipids in alcohol.

30. The method of claim 27, wherein the first lipid component is an amino lipid.

31. The method of claim 27, wherein the second lipid component is a polyethylene glycol-modified or polyamide oligomer-modified lipid.

32. The method of claim 31, wherein the second lipid component is a PEG-Ceramide.

33. The method of claim 31, wherein the first lipid component is an amino lipid.

34. The method of claim 27, wherein said lipid mixture comprises an amino lipid having a pKa of from about 5 to about 11 as the first lipid component, and a PEG-modified or Polyamide oligomer-modified lipid as the second component.

35. The method of claim 34, wherein said lipid mixture comprises in molar percents about 25–45% neutral lipid, about 35–55% Chol, about 10–40% amino lipid and about 0.5–15% PEG-Ceramide as the modified lipid.

36. The method of claim 27, wherein said mixture of lipids comprises DODAP as the first lipid component, DSPC as the neutral lipid, and PEG-CerC14 as the second lipid component.

37. The method of claim 36, wherein said lipids are present in molar percents of about 25–45% DSPC, about 35–55% Chol, about 10–40% DODAP and about 0.5–15% PEG-CerC14.

38. The method of claim 27, wherein said mixture of lipids comprises DODAP as the first lipid component, POPC as the neutral lipid, and PEG-CerC14 as the second lipid component.

39. The method of claim 27, wherein said mixture of lipids comprises DODAP as the first lipid component, SM as the neutral lipid, and PEG-CerC14 as the second lipid component.

40. The method of claim 27, wherein the pH is changed in step (b) to physiological pH.

41. The method of claim 27, wherein the step of changing the pH is performed using tangential flow dialysis.

42. A pharmaceutical composition comprising lipid-encapsulated therapeutic agent particles prepared according to claim 27 and a pharmaceutically acceptable carrier.

43. The method of claim 27, wherein the therapeutic agent is a polyanionic nucleic acid.

44. A pharmaceutical composition comprising lipid-encapsulated therapeutic agent particles comprising a polyanionic nucleic acid as therapeutic agent prepared according to claim 43 and a pharmaceutically acceptable carrier.

45. The pharmaceutical composition according to claim 44, wherein the polyanionic nucleic acid is an antisense nucleic acid.

46. A method for preparation of a composition comprising lipid encapsulated therapeutic agent particles, said method comprising the steps of:
(a) preparing a mixture of lipids comprising an amino lipid, a neutral lipid, a sterol, and a PEG-modified or polyamide oligomer-modified lipid, and combining the mixture of lipids with a buffered aqueous solution of a charged therapeutic agent to form an intermediate mixture containing lipid-encapsulated therapeutic agent particles having exterior surface charges, wherein the amino lipid is selected from among lipids containing a protonatable or deprotonatable group that has a pKa such that the amino lipid is in a charged form at a first pH and a neutral form at a second pH, and said buffered solution having a pH such that the amino lipid is in its charged form when in the buffered solution, said amino lipid being further selected such that the charged form is cationic, said PEG-modified or polyamide oligomer-modified lipid being selected from among lipids that prevent particle aggregation during lipid-nucleic acid particle formation, said neutral lipid being selected from the group consisting of DSPC, POPC, DOPE, and SM, and said sterol being Chol, and said therapeutic agent being a polyanionic nucleic acid, and
(b) changing the pH of the intermediate mixture to neutralize at least some of the exterior surface charges on said lipid-encapsulated therapeutic agent particles to provide at least partially-surface neutralized lipid-encapsulated therapeutic agent particles.

47. The method of claim 46, wherein said composition consists essentially of lipid-nucleic acid particles, said particles having a size of from 70 nm to about 200 nm.

48. The method of claim 46, wherein said mixture of lipids in step (a) is a mixture of lipids in alcohol.

49. The method of claim 46, wherein the second lipid component is a PEG-Ceramide.

50. The method of claim 46, wherein said lipids are-present in molar percents of about 25–45% neutral lipid, 35–55% Chol, 10–40% amino lipid and 0.5–15% PEG-modified or polyamide oligomer-modified lipid.

51. The method of claim 46, wherein said mixture of lipids comprises DODAP as the amino lipid, DSPC as the neutral lipid, and PEG-CerC14 as the PEG-modified lipid.

52. The method of claim 51, wherein said lipids are present in molar percents of about 25–45% DSPC, about 35–55% Chol, about 10–40% DODAP and about 0.5–15% PEG-CerC14.

53. The method of claim 46, wherein said mixture of lipids comprises DODAP as the amino lipid, POPC as the neutral lipid, and PEG-CerC14 as the PEG-modified lipid.

54. The method of claim 46, wherein said mixture of lipids comprises DODAP as the amino lipid, SM as the neutral lipid, and PEG-CerC14 as the PEG-modified lipid.

55. The method of claim 46, wherein said polyanionic nucleic acid is an antisense nucleic acid.

56. The method of claim 55, wherein said antisense nucleic acid contains linkages selected from the group consisting of phosphodiester, phosphorothioate, phosphorodithioate, boranophosphate, phosphoroselenate and amidate linkages.

57. The method of claim 46, wherein said polyanionic nucleic acid contains exclusively phosphodiester linkages.

58. The method of claim 57, wherein said polyanionic nucleic acid is an antisense nucleic acid.

59. The method of claim 57, wherein the buffered solution comprises 10 to 50 mM citrate or phosphate buffer.

60. The method of claim 46, wherein the polyanionic nucleic acid contains at least some phosphorothioate or phosphorodithioate linkages.

61. The method of claim 60, wherein the buffered solution comprises 10 to 300 mM citrate or phosphate buffer.

62. The method of claim 46, wherein said polyanionic nucleic acid is a ribozyme.

63. A method for introducing a polyanionic nucleic acid into a cell, comprising contacting a cell with a composition containing the polyanionic nucleic acid for a period of time sufficient to introduce the polyanionic nucleic acid into said cell, wherein the composition comprises lipid-encapsulated therapeutic agent particles containing the polyanionic nucleic acid and said composition is prepared according to the method of claim 46.

64. A method for the treatment or prevention of a disease characterized by aberrant expression of a gene in a mammalian subject comprising,
preparing a lipid-encapsulated therapeutic agent particle, wherein the therapeutic agent is a polyanionic nucleic acid, according to the method of claim 46, wherein the polyanionic nucleic acid hybridizes specifically with the aberrantly expressed gene; and
administering a therapeutically effective or prophylactic amount of the particle to the mammalian subject, whereby expression of the aberrantly expressed gene is reduced.

65. The method of claim 64, wherein the gene is selected from among ICAM-1, c-myc, c-myb, ras, raf, erb-B-2, PKC-alpha, IGF-1R, EGFR, VEGF and VEGF-R-1.

66. The method of claim 64, wherein the disease is a tumor.

67. The method of claim 64, wherein the disease is characterized by inflammation.

68. The method of claim 64, wherein the disease is an infectious disease.

69. The method of claim 64, wherein the therapeutically effective amount of the particle is administered to the mammalian subject by intravenous injection.

70. The method of claim 69, wherein the therapeutically effective amount of the particle is administered to the mammalian subject by intravenous injection at an injection site, and wherein the disease is localized at a disease site distal to the injection site.

71. The method of claim 64, wherein the polyanionic nucleic acid comprises exclusively phosphodiester linkages.

72. A method of preventing expression of a disease-associated gene in a mammalian cell comprising, preparing a lipid-encapsulated therapeutic agent particle, wherein the therapeutic agent is an antisense polyanionic nucleic acid, according to the method of claim 55; and exposing the mammalian cell to the lipid-encapsulated therapeutic agent particle for a period of time sufficient for the therapeutic agent to enter the cell;

wherein the therapeutic agent has a sequence complementary to the disease-associated gene and reduces the production of the gene product of the disease-associated gene in the cell.

* * * * *